US012686868B2

United States Patent
(12) United States Patent
Goldman et al.

(10) Patent No.: US 12,686,868 B2
(45) Date of Patent: Jul. 21, 2026

(54) METHODS AND COMPOSITIONS FOR REJUVENATING CNS GLIAL POPULATIONS BY SUPPRESION OF TRANSCRIPTION FACTORS

(71) Applicant: UNIVERSITY OF ROCHESTER, Rochester, NY (US)

(72) Inventors: Steven A. Goldman, Webster, NY (US); John N. Mariani, Rochester, NY (US); Abdellatif Benraiss, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 18/047,749

(22) Filed: Oct. 19, 2022

(65) Prior Publication Data

US 2023/0133695 A1 May 4, 2023

Related U.S. Application Data

(60) Provisional application No. 63/350,041, filed on Jun. 8, 2022, provisional application No. 63/350,042, filed (Continued)

(51) Int. Cl.
*C12N 15/113* (2010.01)
*A61K 38/17* (2006.01)
(Continued)

(52) U.S. Cl.
CPC ........ *C12N 15/113* (2013.01); *A61K 38/1709* (2013.01); *A61K 38/45* (2013.01); (Continued)

(58) Field of Classification Search
CPC .............. C12N 15/113; C12N 2310/11; C12N 2310/141; C12N 5/0622; C12N 2501/60; A61K 48/0058; A61P 25/00
See application file for complete search history.

(56) References Cited

U.S. PATENT DOCUMENTS

| | | | |
|---|---|---|---|
| 275,794 | A | 4/1883 | Ward |
| 5,872,005 | A | 2/1999 | Wang et al. |

(Continued)

FOREIGN PATENT DOCUMENTS

| | | | |
|---|---|---|---|
| WO | WO-2018146010 | | 8/2018 |
| WO | 2019246262 | A2 | 12/2019 |

(Continued)

OTHER PUBLICATIONS

Watts JK, Corey DR. Silencing disease genes in the laboratory and the clinic. J Pathol.; 226(2):365-379 (Year: 2012).*

(Continued)

*Primary Examiner* — Catherine Konopka
*Assistant Examiner* — Shabana S Meyering
(74) *Attorney, Agent, or Firm* — Fox Rothschild LLP

(57) ABSTRACT

Methods of inducing rejuvenation in a population of adult glial progenitor cells, and methods of treating a subject having a myelin deficiency are disclosed in this patent application. The method of inducing rejuvenation in a population of adult glial progenitor cells may comprise administering, to the population of adult glial progenitor cells, an effective amount of an agent that suppresses one or more transcription factors selected from the group consisting of (i) zinc finger protein 274 (ZNF274), (ii) Myc-associated factor X (MAX), (iii) E2F transcription factor 6 (E2F6), (iv) zinc finger protein Aiolos (IKZF3), and (v) signal transducer and activator of transcription 3 (STAT3).

12 Claims, 31 Drawing Sheets
(25 of 31 Drawing Sheet(s) Filed in Color)
Specification includes a Sequence Listing.

Related U.S. Application Data on Jun. 8, 2022, provisional application No. 63/350,039, filed on Jun. 8, 2022, provisional application No. 63/257,827, filed on Oct. 20, 2021.

(51) Int. Cl.

| | |
|---|---|
| ***A61K 38/45*** | (2006.01) |
| ***A61K 38/50*** | (2006.01) |
| ***A61K 48/00*** | (2006.01) |
| ***A61P 25/00*** | (2006.01) |
| ***A61P 25/28*** | (2006.01) |
| ***C12N 5/079*** | (2010.01) |
| ***C12N 9/10*** | (2006.01) |
| ***C12N 9/80*** | (2006.01) |
| ***C12N 15/86*** | (2006.01) |

(52) U.S. Cl.

CPC .......... *A61K 38/50* (2013.01); *A61K 48/0058* (2013.01); *A61K 48/0066* (2013.01); *A61P 25/00* (2018.01); *A61P 25/28* (2018.01); *C12N 5/0622* (2013.01); *C12N 9/1007* (2013.01); *C12N 9/80* (2013.01); *C12N 15/86* (2013.01); *C12Y 305/01098* (2013.01); *C12N 2310/141* (2013.01); *C12N 2320/35* (2013.01); *C12N 2740/15032* (2013.01); *C12N 2740/15043* (2013.01)

(56) References Cited

U.S. PATENT DOCUMENTS

| | | | |
|---|---|---|---|
| 6,479,626 B1 | 11/2002 | Kim et al. | |
| 6,534,261 B1 | 3/2003 | Cox, III et al. | |
| 6,607,882 B1 | 8/2003 | Cox et al. | |
| 6,746,838 B1 | 6/2004 | Choo et al. | |
| 6,794,136 B1 | 9/2004 | Eisenberg et al. | |
| 6,824,978 B1 | 11/2004 | Cox et al. | |
| 6,866,997 B1 | 3/2005 | Cambridge et al. | |
| 6,903,185 B2 | 6/2005 | Kim et al. | |
| 6,933,113 B2 | 8/2005 | Case et al. | |
| 6,979,539 B2 | 12/2005 | Cox et al. | |
| 7,013,219 B2 | 3/2006 | Case et al. | |
| 7,030,215 B2 | 4/2006 | Liu et al. | |
| 7,220,719 B2 | 5/2007 | Case et al. | |
| 7,241,573 B2 | 7/2007 | Choo et al. | |
| 7,241,574 B2 | 7/2007 | Choo et al. | |
| 7,485,291 B2 | 2/2009 | Fang et al. | |
| 7,585,849 B2 | 9/2009 | Liu et al. | |
| 7,595,376 B2 | 9/2009 | Kim et al. | |
| 7,745,592 B2 | 6/2010 | Massie et al. | |
| 8,440,431 B2 | 5/2013 | Voytas et al. | |
| 8,440,432 B2 | 5/2013 | Voytas et al. | |
| 8,450,471 B2 | 5/2013 | Voytas et al. | |
| 8,586,363 B2 | 11/2013 | Voytas et al. | |
| 8,697,853 B2 | 4/2014 | Voytas et al. | |
| 8,728,759 B2 | 5/2014 | Xu et al. | |
| 2003/0223972 A1 | 12/2003 | Goldman et al. | |
| 2004/0029269 A1 | 2/2004 | Goldman et al. | |
| 2015/0362508 A1 | 12/2015 | Buckner | |
| 2020/0087622 A1 | 3/2020 | Nair et al. | |
| 2023/0133695 A1* | 5/2023 | Goldman ............... | C12N 15/86 514/44 A |
| 2023/0212568 A1 | 7/2023 | Goldman et al. | |
| 2023/0241118 A1* | 8/2023 | Goldman ................ | A61P 25/00 424/93.21 |
| 2024/0167034 A1* | 5/2024 | Goldman ....... | C12Y 305/01098 |
| 2024/0254466 A1* | 8/2024 | Fernandes ................ | C12N 9/22 |

FOREIGN PATENT DOCUMENTS

| | | |
|---|---|---|
| WO | 2020167822 | 8/2020 |
| WO | 2021159059 A1 | 8/2021 |

OTHER PUBLICATIONS

Sánchez-González, R., Salvador, N. & López-Mascaraque, L. Unraveling the adult cell progeny of early postnatal progenitor cells. Sci Rep 10, 19058 (Year: 2020).*
Zhang et al., Hdac3 Interaction with p300 Histone Acetyltransferase Regulates the Oligodendrocyte and Astrocyte Lineage Fate Switch, Developmental Cell, vol. 36, Issue 3, pp. 316-330 (Year: 2016).*
Tiane et al., From OPC to Oligodendrocyte: An Epigenetic Journey. Cells. Oct. 11, 2019;8(10):1236) (Year: 2019).*
Chen H et al., Characterization of glial-restricted precursors from rhesus monkey embryonic stem cells (ESC). Transl Neurosci. Nov. 27, 2015;6(1):244-251 (Year: 2015).*
Trimarchi, J. M., Fairchild, B., Verona, R., Moberg, K., Andon, N., & Lees, J. A. (Year: 1998).*
Hidesato Ogawa et al.A Complex with Chromatin Modifiers That Occupies E2F- and Myc-Responsive Genes in GO Cells. Science 296,1132-1136 (Year: 2002).*
Alerie G. de la Fuente et al., Changes in the Oligodendrocyte Progenitor Cell Proteome with Ageing, Molecular & Cellular Proteomics, vol. 19, Issue 8, pp. 1281-1302 (Year: 2020).*
Neumann et al., Metformin Restores CNS Remyelination Capacity by Rejuvenating Aged Stem Cells. Cell stem cell, 25(4), 473-485 .e8 (Year: 2019).*
J.M. Ruckh, J et al., Rejuvenation of regeneration in the aging central nervous system, Cell Stem Cell, 10, pp. 96-103 (Year: 2012).*
Chamberlain KA, Nanescu SE, Psachoulia K, Huang JK. Oligodendrocyte regeneration: Its significance in myelin replacement and neuroprotection in multiple sclerosis. Neuropharmacology. Nov. 2016;110(Pt B):633-643. (Year: 2016).*
NCBI [retrieved on Jun. 27, 2024]. Retrieved from the Internet: <URL: https://www.ncbi.nlm.nih.gov/gene/4288#summary> (Year: 2024).*
Credo Ref (Credo Ref, 2017 [retrieved on Jun. 27, 2024]. Retrieved from the Internet: <URL: https://search.credoreference.com/articles/Qm9va0FydGljbGU6NDY1NzgyOQ==?q=induce>) (Year: 2017).*
Kritsilis M. et al., Int J Mol Sci. Sep. 27, 2018;19(10):2937. doi: 10.3390/ijms19102937 (Year: 2018).*
Kim Y. et al., pp. 622-634, vol. 12, Issue 4, Aug. 2013 (Year: 2013).*
Sengupta, S. (2016). Available from ProQuest Dissertations & Theses Global. (1845009166). Retrieved from <https://www.proquest.com/dissertations-theses/function-stat3-smg1-maintaining-glioblastoma-stem/docview/1845009166/se-2> (Year: 2016).*
Tian (Zhonghua Mazuixue Zazhi , 2006, vol. 26(3), p. 265-268), English abstract. (Year: 2006).*
Swarts & Jinek, Mol Cell. Feb. 7, 2019; 73(3): 589-600.e4. (Year: 2019).*
Savage, Biochemistry 2019, 58, 1024-1025 (Year: 2019).*
Gao et al. 2016 Nature Methods. 13(12) 1043-1051 (Year: 2016).*
Kurosinski P, Götz J. Glial Cells Under Physiologic and Pathologic Conditions. Arch Neurol. 2002;59(10): 1524-1528. (Year: 2002).*
Wenfeng (Nao Yu Shenjing Jibing Zazhi (2021), 29(5), 36-41, Chinese) (Year: 2021).*
English translation of Wenfeng (Nao Yu Shenjing Jibing Zazhi (2021), 29(5), 36-41, Chinese) (Year: 2021).*
Jinek M. et al., Science. Aug. 17, 2012; 337(6096): 816-821) (Year: 2012).*
Genbank, *Homo sapiens* E2F6 mRNA, NM_001278277.2, revision Jun. 29, 2021, retrieved Aug. 28, 2025, 7pgs (Year: 2021).*
Papadopoulos et al., Front. Cell. Neurosci., Jun. 29, 2020, Sec. Cellular Neuropathology, vol. 14—2020 (Year: 2020).*
Lin et al., PLOS ONE, Mar. 2013 | vol. 8 | Issue 3 | e56379 (Year: 2013).*
Neumann Bjom et al. “Myc determines the functional age state of oligodendrocyte progenitor cells”, Nature Aging, vol. 1 No. 9 Sep. 14, 2021 pp. 826-837.
Mariani, John et al. “Age Associated Induction of Senescent Transcriptional Programs in Human Glial Progenitor Cells”, SSRN Electronic Journal, Sep. 25, 2021, pp. 1-51.

(56) References Cited

OTHER PUBLICATIONS

International Search Report and Written Opinion, issued in International Patent Application No. PCT/US2022/047079, mail date, Feb. 20, 2023.

International Search Report and Written Opinion, issued in International Patent Application No. PCT/US2022/047083, mail date Mar. 15, 2023.

International Search Report and Written Opinion, issued in International Patent Application No. PCT/US2022/047085, mail date Feb. 23, 2023.

Neumann Bjorn et al. "Metformin Restores CNS Remyelination Capacity by Rejuvenating Aged Stem Cells", Cell Stem Cell, Cell Press, vol. 25, No. 4 Oct. 3, 2019.

Abstract 1288: Blocking Tumor Associated Immune Suppression with BAY-218, a Novel, Selective Aryl Hydrocarbon Receptor (AhR) Inhibitor, Proceedings of the American Association for Cancer 25 Research Annual Meeting 2019.

Ahlin et al., "High Expression of Cyclin D1 is Associated to High Proliferation Rate and Increased Risk of Mortality in Women With ER-positive but not in ER-negative Breast Cancers," Breast Cancer Res. Treat 164:667-678 (2017).

Aibar et al., "SCENIC: Single-cell Regulatory Network Inference and Clustering," Nat. Methods 14:1083-1088 (2017).

Aird, K.M., et al., (2013). Suppression of nucleotide metabolism underlies the establishment and maintenance of oncogene-induced senescence. Cell Rep 3, 1252-1265).

Alerasool et al., "An Efficient KRAB Domain for CRISPRI Applications in Human Cells," Nature Methods 17:1093-1096 (2020).

Bastian et al., "Gephi: An Open Source Software for Exploring and Manipulating Networks," (2009).

Beurdeley et al., "Compact Designer TALENs for Efficient Genome Engineering," Nat. Commun. 4:1762 (2013).

Blackwood and Eisenman, "Max: A Helix-loop-helix Zipper Protein That Forms a Sequence-specific DNA-binding Complex With Myc," Science 251:1211-1217 (1991).

Boitano et al., "Aryl Hydrocarbon Receptor Antagonists Promote the Expansion of Human Hematopoietic Stem Cells," Science 329(5997):1345-1348 (2010).

Borgdorff et al., Multiple microRNAs rescue from Ras-induced senescence by inhibiting p21(Waf1/Cip1). Oncogene 29, 2262-2271).

Bouard et al., "Viral Vectors: From Virology to Transgene Expression," Br. J. Pharmacol. 157(2):153-165 (2009).

Bouhrara et al., "Evidence of Demyelination in Mild Cognitive Impairment and Dementia Using a Direct and Specific Magnetic Resonance Imaging Measure of Myelin Content," Alzheimers Dement. 14:998-1004 (2018).

Bretones et al., "Myc and Cell Cycle Control," Biochim. Biophys Acta 1849:506-516 (2015).

Brezgin et al., "Dead Cas Systems: Types, Principles, and Applications." Int. J. Mol. Sci. 20(23):6041 (2019).

Budde, H. Schmitt, S., Fitzner, D., Opitz, L., Salinas-Riester, G., and Simons, M. (2010). Control of oligodendroglial cell number by the mIR-17-92 cluster. Development 137. 2127).

Bulcha et al., "Viral Vector Platforms within the Gene Therapy Landscape," Nature 6:53 (2021).

Buning et al, "Recent Developments in Adeno-associated Virus Vector Technology," J. Gene Med. 10:717-733 (2008).

Bunt et al., "Regulation of Cell Cycle Genes and Induction of Senescence by Overexpression of OTX2 in Medulloblastoma Cell Lines," Mol. Cancer Res. 8:1344-1357 (2010).

Butler et al., "Integrating Single-cell Transcriptomic Data Across Different Conditions, Technologies, and Species," Nat Biotechnol 36:411-420 (2018).

Campesato et al., "Blockade of the AHR Restricts a Treg-Macrophage Suppressive Axis Induced by L-5 Kynurenine," Nature Comm. 11:4011 (2020).

Campos-Viguri, G.E. et al., (2020). MiR-23b-3p reduces the proliferation, migration and invasion of cervical cancer cell lines via the reduction of c-Met expression. Sci Rep 10, 3256).

Carvalho and Irizarry, "A Framework for Oligonucleotide Microarray Preprocessing," Bioinformatics 26:2363-2367 (2010).

Castell et al., "A Selective High Affinity MYC-Binding Compound Inhibits MYC:MAX Interaction and MYC-Dependent Tumor Cell Proliferation," Sci. Rep. 8:10064 (2018).

Chambers et al., "Highly Efficient Neural Conversion of Human ES and IPS Cells by Dual Inhibition of SMAD Signaling," Nat Biotechnol 27:275-280 (2009).

Chambers et al., Nature biotechnology, 27, 275-280, 2009.

Chari et al., "Decline in Rate of Colonization of Oligodendrocyte Progenitor Cell (OPC)-depleted Tissue by Adult OPCs with Age," J. Neuropathol. Exp. Neurol. 62:908-916 (2003).

Chavez et al., "Highly Efficient Cas9-Mediated Transcriptional Programming," Nat. Methods, 12:326 (2015).

Chen et al., "fastp: An Ultra-fast All-in-one FASTQ Preprocessor," Bioinformatics 34:1884-1890 (2018).

Chen, J. et al., (2016), Pathologically decreased expression of miR-193a contributes to metastasis by targeting WT1-E-cadherin axis in non-small cell lung cancers. J Exp Clin Cancer Res 35, 173).

Cheng et al., "Multiplexed Activators of Endogenous Genes by CRISPR-on, an RNA-Guided Transcriptional Activator System," Cell Res. 23:1163 (2013).

Cho et al., "POZ/BTB and AT-hook-containing Zinc Finger Protein 1 (PATZ1) Inhibits Endothelial Cell Senescence Through a p53 Dependent Pathway," Cell Death Differ 19:703-712 (2012).

Csardi G.N., Tamas "The Igraph Software Package for Complex Network Research," InterJournal Complex Systems 1695 (2006).

De La Fuente et al., "Changes in the Oligodendrocyte Progenitor Cell Proteome with Ageing," Mol. Cell Proteomics 19:1281-1302 (2020).

De Medina et al., "Synthesis and Biological Properties of New Stilbene Derivatives of Resveratrol as New Selective Aryl Hydrocarbon Modulators," J. Med. Chem. 48:287-291 (2005).

Deneen et al., "The Transcription Factor NFIA the Onset of Gliogenesis in the Developing Spinal Cord," Neuron 52:953-968 (2006).

Diepenbruck et al., "Tead2 Expression Levels Control the Subcellular Distribution of Yap and Taz, Zyxin Expression and Epithelial-mesenchymal Transition," Journal of Cell Science 127:1523-1536 (2014).

Dietrich et al., "Characterization of A2B5+ Glial Precursor Cells From Cryopreserved Human Fetal Brain Progenitor Cells," Glia 40:65-77 (2002).

Diril, M.K. et al., (2012). Cyclin-dependent kinase 1 (Cdk1) is essential for cell division and suppression of DNA re-replication but not for liver regeneration. Proc Natl Acad Sci U S A 109, 3826-3831).

Dobin et al., "STAR: Ultrafast Universal RNA-seq Aligner," Bioinformatics 29:15-21 (2013).

Du et al. (2014b). miR-17 extends mouse lifespan by inhibiting senescence signaling mediated by MKP7. Cell Death Dis 5, e1355).

Du W. et al., (2014a). By Targeting Stat3 microRNA-17-5p Promotes Cardiomyocyte Apoptosis in Response to Ischemia Followed by Reperfusion. Cellular Physiology and Biochemistry 34, 956-965).

Dugas et al., (2010). Dicer1 and miR-219 are required for normal oligodendrocyle differentiation and myelination. Neuron 65, 597-611).

Duke et al., "An Improved CRISPR/dCas9 Interference Tool for Neuronal Gene Suppression," Frontiers in Genome Editing 2:9 (2020).

Eckers, A. et al., (2016). The aryl hydrocarbon receptors promotes aging phenotypes across species. Sci Rep 6, 19618).

Erickson et al., "Brain-derived Neurotrophic Factor is Associated with Age-related Decline in Hippocampal Volume," J. Neurosci. 30:5368-5375 (2010).

Fan et al., "EZH2-dependent Suppression of a Cellular Senescene Phenotype in Melanoma Cells by Inhibition of p21/CDKN1A Expression," Mol. Cancer Res. 9:418-429 (2011).

Ferrand et al., "Screening of a Kinase Library Reveals Novel Pro-senescence Kinases and Their Common NF-xB.-dependent Transcriptional Program," Aging (Albany NY) 7:986-1003 (2015).

(56) References Cited

OTHER PUBLICATIONS

Finaket al., "MAST:A Flexible Statistical Framework for Assessing Transcriptional Changes and Characterizing Heterogeneity in Single-cell RNA Sequencing Data," Genome Biology 16:278 (2015).
Freund et al., "Lamin B1 Loss is a Senescence-associated Biomarker," Mol. Biol. Cell 23:2066-2075 (2012).
Frietze et al. "ZNF274 Recruits the Histone Methyltransferase SETDB1 to the 3' Ends of ZNF Genes," PLoS One 5: e15082 (2010).
Fuh et al., "LLL-3 Inhibits STAT3 Activity, Suppresses Glioblastoma Cell Growth and Prolongs Survival in a Mouse Glioblastoma Model," Br. J. Cancer 100(1):106-112 (2009).
Fuyuno et al., "Perillaldehyde Inhibits AHR Signaling and Activates NRF2 Antioxidant Pathway in Human Keratinocytes," Oxid. Med. Cell Longev. 2018:9524657 (2018).
Gaj et al., "Targeted Gene Knockout by Direct Delivery of Zinc-Finger Nuclease Proteins," Nat. Methods 9(8):805-807 (2012).
Gao and Raff, "Cell Size Control and a Cell-intrinsic Maturation Program in Proliferating Oligodendrocyte Precursor Cells," J. Cell Biol. 138:1367-1377 (1997).
Gilbert et al., "CRISPR-Mediated Modular RNA-Guided Regulation of Transcription in Eukaryotes," Cell 154:442-451 (2013).
Gingrich and Roder, "Inducible Gene Expression in the Nervous System of Transgenic Mice," Annu. Rev. Neurosci. 21:377-406 (1998).
Harris et al., "Coordinated Changes in Cellular Behavior Ensure the Lifelong Maintenance of the Hippocampal Stem Cell Population," Cell Stem Cell (2021).
Huang et al., "Origins and Proliferative States of Human Oligodendrocyte Precursor Cells." Cell 182:594-608 e511 (2020).
Hubbard et al., "Napabucasin: An Update on the First-in-Class Cancer Stemness Inhibitor," Drugs 77(10):1091-1103 (2017).
Inque et al., "Disruption of the ARF Transcriptional Activator DMP1 Facilitates Cell Immortalization, Ras Transformation, and Tumorigenesis," Genes Dev 14:1797-1809 (2000).
Kallunki et al., "How to Choose the Right Inducible Gene Expression System for Mammalian Studies?" Cells 8(6):796 (2019).
Koh et al., "Use of a Stringent Dimerizer-Regulated Gene Expression System for Controlled BMP2 Delivery," Mol. Ther. 14(5):P684-691 (2006).
Konermann et al., "Genom Scale Transcriptional Activation by an Engineered CRISPR-Cas9 Complex," Nature 517(7536):583-588 (2015).
Krause et al., "Delivery of Antigens by Viral Vectors for Vaccination," Ther. Deliv. 2(1):51-70 (2011).
Kulkarni et al., "The Current Landscape of Nucleic Acid Therapeutics," Nature Nanotechnology 16:630-643 (2021).
Laherty et al., "Histone Deacetylases Associated With the mSin3 Corepressor Mediate Mad Transcriptional Repression," Cell 89:349-356 (1997).
McManus & Sharp, "Gene Silencing in Mammals by Small Interfering RNAs," Nat. Rev. Genet. 3(10):737-747 (2002).
McMurray, "A New Small-Molecule Stat3 Inhibitor," Chem. Biol. 13(11):1123-1124 (2006).
Morita et al., "Targeted DNA Demethylation in vivo using dCas9-Peptide Repeat and scFv-TET1 Catalytic Domain Fusions," Nat. Biotechnol. 34:1060-1065 (2016).
Moyon et al., "TET1-mediated DNA Hydroxymethylation Regulates Adult Remyelination in Mice," Nature Communications 12:3359-3359 (2021).
Nakamura et al., "Evi9 Encodes a Novel Zinc Finger Protein that Physically Interacts with BCL6, a known Human B-Cell Proto-Oncogene Product," Mol Cell Biol 20:3178-3186 (2000).
Neumann et al., "Metformin Restores CNS Remyelination Capacity by Rejuvenating Aged Stem Cells," Cell Stem Cell 25:473-485 e478 (2019).
Neumann et al., "Myc Determines the Functional Age State of Oligodendrocyte Progenitor Cells," Nature Aging 1:826-837 (2021).
Liu et al., "Editing DNA Methylation in the Mammalian Genome," Cell 167:233-247 (2016).
Liu et al., "Engineering Cell Signaling Using Tunable CRISPR-Cpf1-Based Transcription Factors," Nat. Commun. 8:2095 (2017).
Liu et al., "SOCS3 Promotes Inflammation and Apoptosis via Inhibiting JAK2/STAT3 Signaling Pathway in 3T3-L1 Adipocyte," Immunobiology 220(8):947-953 (2015).
Love et al., "Moderated Estimation of Fold Change and Dispersion on for RNA-q Data With DESeq2," Genome Biology 15:560 (2014).
Luc et al., "Bcl11a Deficiency Leads to Hematopoietic Stem Cell Defects with an Aging-like Phenotype," Cell Rep. 16:3181-3194 (2016).
Lukjanenko et al., "Loss of Fibronectin From the Aged Stem Cell Niche Affects the Regenerative Capacity of Skeletal Muscle in Mice," Nat Med 22:897-905 (2016).
Ma et al., "Ikaros and Aiolos Inhibit Pre-B-cell Proliferation by Directly Suppressing c-Myc Expression," Mol Cell Biol 30:4149-4158 (2010b).
Lam et al., "sIRNA Versus miRNA as Therapeuics for Gene Silencing," Mol. Ther, Nucleic Acids 4(9):e262 (2015).
Lee et al., "Phenolic Compounds Isolated from Psoralea corylifolia Inhibit IL-6-Induced STAT3 Activation," Planta. Med. 78(9):903-906 (2012).
Lenth., "Least-Squares Means: The R Package Ismeans," Journal of Statistical Software, Foundation for Open Access Statistics 69(i01) (2016).
Li & Dewey, "RSEM: Accurate Transcript Quantification From RNA-Seq Data With or Without a Reference Genome," BMC Bioinformatics 12:323 (2011).
Li et al., "A potent Cas9-Derived Gene Activator for Plant and Mammalian Cells," Nat. Plants. 3:930-936 (2017).
Li et al., "Suppression of Cancer Relapse and Metastasis by Inhibiting Cancer Stemness," PNAS 112(6):1839-1844 (2015).
Liu et al., "CD44 Expression Identifies Astrocyte-Restricted Precursor Cells," Dev. Biol. 276(1):31-46 (2004).
Nunes et al., "Identification and Isolation of Multipotential Neural Progenitor Cells From the Subcortical White Matter of the Adult Human Brain.," Nat Med. 9(4):439-47 (2003).
Ogawa et al., "A Complex with Chromatin Modifiers that Occupies E2F- and Myc-Responsive Genes in G0 Cells," Science 296:1132-1136 (2002).
Orlova et al., "Direct Targeting Options for STAT3 and STAT5 in Cancer," Cancers 11(12):1930 (2019).
Pajak M., "miRNAtap: MIRNAtap microRNA Targets—Aggregated Predictions," Package Version 1.22.0 (2020).
Perlman et al., "Developmental Trajectory of Oligodendrocyte Progenitor Cells in the Human Brain Revealed by Single Cell RNA Sequencing," Glia 68:1291-1303 (2020).
Qi et al., "Repurposing CRISPR as an RNA-Guided Platform for Sequence-Specific Control of Gene Expression," Cell 152(5):1173-1183 (2013).
Reichardt et al., "Statistical Mechanics of Community Detection," Phys. Rev. E Stat. Nonlin. Soft Matter Phys. 74:016110 (2006).
Ritchie et al.,"Limma Powers Differential Expression Analyses for RNA-Sequencing and Microarray Studies," Nucleic Acids Res 43:e47 (2015).
Roberts et al., "Advances in Oligonucleotide Drug Delivery," Nature Reviews Drug Discovery 19:673-694 (2020).
Scharenberg et al., "Genome Engineering with TAL-Effector Nucleases and Alternative Modular Nuclease Technologies," Curr. Gene Ther. 13(4):291-303 (2013).
Segel et al., "Niche Stiffness Underlies the Ageing of Central Nervous System Progenitor Cells," Nature 573:130-134 (2019).
Shannon P., "Cyloscape: A Software Environment for Integrated Models of Biomolecular Interaction Network," Genome Res 13:2498-2504 (2003).
Sim et al., "Fate Determination of Adult Human Glial Progenitor Cells," Neuron Glia Biol 5:45-65 (2009).
Smithet al., "Identification of a High-Affinity Ligand that Exhibits Complete Aryl Hydrocarbon Receptor Antagonism," J. Pharmacol. Exp. Ther. 338(1):318-327 (2011).
Soneson et al., "Differential Analyses for RNA-seq: Transcript-Level Estimates Improve Gene-Level Inferences," F1000Research 4:1521 (2015).

(56) References Cited

OTHER PUBLICATIONS

Song et al., "A Low-Molecular-Weight Compound Discovered through Virtual Database Screening Inhibits Stat3 Function in Breast Cancer Cells," PNAS 102(13):4700-4705 (2005).

Spitzer et al., "Oligodendrocyte Progenitor Calls Become Regionally Diverse and Heterogeneous with Age," Neuron 101:469-471 e456 (2019).

Sun et al., "Development of Drug-20 Inducible CRISPR-Cas9 Systems for Large-Scale Functional Screening," BMC Genomics 20:225 (2019).

Tak et al., "Inducible and Multiplex Gene Regulation Using CRISPR-Cpf1-Based Transcription Factors," Nat. Methods 14:1163-1166 (2017).

Temple & Raff, "Clonal Analysis of Oligodendrocyte Development in Culture: Evidence for a Developmental Clock that Counts Cell Divisions," Cell 44:773-779 (1986).

Tierney et al., "HO-3867, a STAT3 Inhibitor Induces Apoptosis by Inactivation of STAT3 Activity in BRCA1-Mutated Ovarian Cancer Cells," Cancer Biol. Ther, 13(9):766-775 (2012).

Tong et al., "TransmiR v2.0: An Updated Transcription Factor-microRNA Regulation Database," Nucleic Acids Res 47:D253-0258 (2019).

Ura et al., "Devel ments in Viral Vector-Based Vaccines," Vaccines 2: 624-641 (2014).

Urnov et al., "Genome Editing with Engineered Zinc Finger Nucleases," Nat. Rev. Genet. 11(9):636-646 (2010).

Wang et al., "Human iPSC-Derived Oligodendrocyte Progenitor Cells Can Myelinate and Rescue a Mouse Model of Congenital Hypomyelination," Cell Stem Cell 12:252-264 (2013).

Wang et al., "Improved Low Molecular Weight Myc-Max inhibitors," Mol. Cancer Ther. 6(9):2399-2408 (2007).

Wang et al., Cell Stem Cell 12, 252-264, 2013.

Windrem et al. J. Neurosci 34, 16153-16161 (2014).

Windrem et al., "Fetal and Adult Human Oligodendrocyte Progenitor Cell Isolates Myelinate the Congenitally Dysmyelinated Brain," Nat. Med. 10:93-97 (2004).

Windrem et al., "Human iPSC Glial Mouse Chimeras Reveal Glial Contributions to Schizophrenia," Cell Stem Cell 21:196-208.e196 (2017).

Wolswijk & Noble, "Identification of an Adult-Specific Glial Progenitor Cell," Development 105:387-400 (1989).

Wotton et al., "RUNX1 Transformation of Primary Embryonic Fibroblasts is Revealed in the Absence of p53," Oncogene 23:5478-5486 (2004).

Wren et al., "In Vitro Analysis of the Origin and Maintenance of O-2Aadult Progenitor Cells," J. Cell Biol. 116,:167-176 (1992).

Wu et al., "Negative Regulators of STAT Signaling Pathway in Cancers," Cancer Manag. Res. 11:4957-4969 (2019).

Xie et al., "YAP/TEAD-Mediated Transcription Controls Cellular Senescence," Cancer Res 73:3615-3624 (2013).

Xu et al., "A CRISPR-Based Approach for Targeted DNA Demethylation," Cell Discov. 2:16009 (2016).

Xu et al., "Population Pharmacokinetic Analysis of Danvatirsen Supporting Flat Dosing Switch," J. Pharmacokinet. Pharmacodyn. 46(1):65-74 (2019).

Yang et al., "The Aryl Hydrocarbon Receptor Constitutively Represses C-Myc Transcription in Human Mammary Tumor Cells," Oncogene 24:7869-7881 (2005).

Yattah et al., "Dynamic Lamin B1-Gene Association During Oligodendrocyte Progenitor Differentiation," Neurochem Res 45:606-619 (2020).

Yeo et al., "An Enhanced CRISPR Repressor for Targeted Mammalian Gene Regulation," 15(8):611-616 (2018).

Lin R. et al., PLoS One. 2013;8(3): e56379. doi: 10.1371/journal.pone.0056379. Epub Mar. 5, 2013 (Year: 2013).

Filippi et al., Nat Rev Dis Primers. Nov. 8, 2018;4(1):43. doi: 10.1038/s41572-018-0041-4 (Year: 2018).

Zhou et al., Cell, vol. 181, Issue 3, 2020, pp. 590-603.e16, ISSN 0092-8674 (Year: 2020).

Friesenhahn (Laurie Beth Friesenhahn, 'E2F6 in Axial Skeletal Development and Gliosis'. In [online]: MIT Libraries, 2008 [retrieved on Mar. 2, 2025]. 186 pages. Retrieved from the Internet: <URL: hdl. handle. net/1721.1 /45802>) (Year: 2008).

Heinen et al., Histone Methyltransferase Enhancer of Zeste Homolog 2 Regulates Schwann Cell Differentiation, 2012, GLIA, vol. 60, p. 1696-1708 (Year: 2012).

Windrem et al., Human Glial Progenitor Cells Effectively Remyelinate the Demyelinated Adult Brain, 2020, Cell Reports, vol. 31, p. 1-23 (Year: 2020).

Liu et al., A molecular insight of Hes5-dependent inhibition of myelin gene expression: old partners and new players, 2006, the EM BO Journal, vol. 25, p. 4833-4842 (Year: 2006).

Merten et al., Viral Vectors for Gene Therapy, 2011, Springer, Chapters 7-9, p. 157-210 (Year: 2011).

Sher et al., "Ezh2 Expression in Astrocytes Induces Their Dedifferentiation Toward Neural Stem Cells", 2011, Cellular Reprogramming, vol. 13, p. 1-6 (Year: 2011).

Suh, "MicroRNA controls of Cellular Senescence", BMB Rep. 2018; 51(10): 493-499. (Year: 2018).

Hubler et al. Nature. Aug. 2018; 560(7718): 372-376 (Year: 2018).

Fernandez et al. Medicine—Programa de Formacion MedicaContinuada Acreditado vol. 11, Issue 77,Apr. 2015 , pp. 4601-4609 English Abstract only (Year: 2015).

Bennett, F., Annu Rev Med., Jan. 27, 2019:70:307-321. (Year: 2019).

Kallunki T, Barisic M, Jaatela M, Liu B. How to Choose the Right Inducible Gene Expression System for Mammalian Studies? Cells. Jul. 30, 2019;8(8):796. doi: 10.3390/cells8080796. PMID: 31366153; PMCID: PMC6721553.

Liu, W. et al., "Mechanism of miR-561 on the differentiation and proliferation of neural stem cells by regulating E2F6 protein expression," Journal of Brain and Neurological Diseases (2021); 29(5): pp. 298-303.

Heng Du et al., Transcription factors Bel11a and Bel11b are required for the production and differentiation of cortica projection neurons, Dec. 29, 2021, Cerebral Cortex, vol. 32, p. 3611-3632 (Year: 2021).

Andrea Grostol Dietz et al., Glial cells in schizophrenia: A unified hypothesis, Mar. 2020, Lancet Psychiatry, vol. 7, p. 272-281 (Year: 2020)

Abdulazeez et al., The rs61742690 (S783N) single nucleotide polymorphism is a suitable target for disrupting BCL11A-mediated foetal-to-adult globin switching, Feb. 2019, PLoS One, vol. 14 (Year: 2019).

Dias et al., BCL11A Haploinsufsufficiency Causes an Intellectual Disability Syndrome and Dysregulates Transcription, Aug. 2016, American Journal of Human Genetics, vol. 99 (Year: 2016).

Adlakha et al., "Brain microRNAs and insights into biological functions and therapeutic potential of brain enriched miRNA-128", Molecular Cancer (2014); 13(33): pp. 1-11.

Brown TA, Genomes, 2nd edition, Chapter 1 (2002).

Jovicic et al., "Comprehensive Expression Analysis of Neural Cell-Type-Specific miRNAs Identify New Determinants of the Specification and Maintenance of Neuronal Phenotypes", The Journal of Neuroscience (2013); 33(12): pp. 5127-5137.

Lin (Progress in MS Research Conference, Melbourne, Australia, 2011 Conference Abstracts. Multiple Sclerosis Journal. P-20, p. 701-702, 2012;18(5):697-703) (Year: 2011).

Rebe et al., JAK-STAT 2:1, e23010; Jan./Feb./Mar. 2013 (Year: 2013).

Swarts & Jinek, Mol Cell. Feb. 7, 2019; 73(3): 589-600.e4.

Sun et al., STAT3 represents a molecular switch possibly inducing astroglial instead of oligodendroglial differentiation of oligodendroglial progenitor cells in Theiler's murine encephalomyelitis, Neuropathology and Applied Neurobiology, vol. 41, p. 347, 2014 (Year: 2014).

Tingting et al., Targeted inhibition of STAT3 in neural stem cells promotes neuronal differentiation and functional recovery in rats with spinal cord injury, Experimental and Therapeutic Medicine, vol. 22, p. 1, Feb. 2021 (Year: 2021).

Eitan et al., Astra-logics with microRNAs, The EMBO Journal, vol. 34, pp. 1143-1144, 2015 (Year: 2015).

(56) References Cited

OTHER PUBLICATIONS

Pons-Espinal et al., Synergic Functions of miRNAs Determine Neuronal Fate of Adult Neural Stem Cells, Stem Cell Reports, vol. 8, p. 1048, Apr. 2017 (Year: 2017).
Office Action issued on Sep. 30, 2024 for U.S. Appl. No. 18/467,442 (23 pages).
Goldman SA, Kuypers NJ. How to make an oligodendrocyte. Development. Dec. 1, 2015;142(23):3983-95.
Grieger JC, Samulski RJ. Adeno-associated virus as a gene therapy vector: vector development, production and clinical applications. Adv Biochem Eng Biotechnol. 2005;99:119-45.
Han, X., Yang, R., Yang, H. et al. miR-4651 inhibits cell proliferation of gingival mesenchymal stem cells by inhibiting HMGA2 under nifedipine treatment. *Int J Oral Sci* 12, 10 (2020).
Hernandez-Segura A, de Jong TV, Melov S, Guryev V, Campisi J, Demaria M. Unmasking Transcriptional Heterogeneity in Senescent Cells. Curr Biol. Sep. 11, 2017;27(17):2652-2660.e4.
Hilton IB, D'Ippolito AM, Vockley CM, Thakore PI, Crawford GE, Reddy TE, Gersbach CA. Epigenome editing by a CRISPR-Cas9-based acetyltransferase activates genes from promoters and enhancers. Nat Biotechnol. May 2015;33(5):510-7.
Hollander et al., (1999). Genomic instability in Gadd45a-deficient mice. Nature genetics, vol. 23, Oct. 1999.
Hu et al, „ Immunization Delivered by Lentiviral Vectors for Cancer and Infection, Immunological Reviews, vol. 239, Issue 1 pp. 45-61.
Huang M, et al., A small-molecule c-Myc inhibitor, 10058-F4, induces cell-cycle arrest, apoptosis, and myeloid differentiation of human acute myeloid leukemia, Experimental Hematology, vol. 34, Issue 11, 2006, pp. 1480-1489, ISSN 0301-472X.
Kilbey A, Blyth K, Wotton S, Terry A, Jenkins A, Bell M, Hanlon L, Cameron ER, Neil JC. Runx2 disruption promotes immortalization and confers resistance to oncogene-induced senescence in primary murine fibroblasts. Cancer Res. Dec. 1, 2007;67(23):11263-71.
Kim SH, Henry EC, Kim DK, Kim YH, Shin KJ, Han MS, Lee TG, Kang JK, Gasiewicz TA, Ryu SH, Suh PG. Novel compound 2-methyl-2H-pyrazole-3-carboxylic acid (2-methyl-4-o-tolylazo-phenyl)-amide (CH-223191) prevents 2,3,7,8-TCDD-induced toxicity by antagonizing the aryl hydrocarbon receptor. Mol Pharmacol. Jun. 2006;69(6):1871-8.
Kim BC, Lee HC, Lee JJ, Choi CM, Kim DK, Lee JC, Ko YG, Lee JS. Wig1 prevents cellular senescence by regulating p21 mRNA decay through control of RISC recruitment. EMBO J. Nov. 14, 2012;31(22):4289-303. doi:10.1038/emboj.2012.286.
Kojima H, Inoue T, Kunimoto H, Nakajima K. IL-6-STAT3 signaling and premature senescence. JAKSTAT. Oct. 1, 2013;2(4):e25763.
Kunii A, Hara Y, Takenaga M, Hattori N, Fukazawa T, Ushijima T, Yamamoto T, Sakuma T. Three-Component Repurposed Technology for Enhanced Expression: Highly Accumulable Transcriptional Activators via Branched Tag Arrays. CRISPR J. Oct. 2018;1(5):337-347.
Laible G, Wolf A, Dorn R, Reuter G, Nislow C, Lebersorger A, Popkin D, Pillus L, Jenuwein T. Mammalian homologues of the Polycomb-group gene Enhancer of zeste mediate gene silencing in *Drosophila heterochromatin* and at *S. cerevisiae* telomeres. EMBO J. Jun. 2 1997;16(11):3219-32.
Lau, P., Verrier, J. D., Nielsen, J. A., Johnson, K. R., Notterpek, L., & Hudson, L. D. (2008). Identification of dynamically regulated microRNA and mRNA networks in developing oligodend rocytes. *Journal of Neuroscience*, 28(45), 11720-11730.
Lee JS, Zhang Z. O-linked N-acetylglucosa mine transferase (OGT) interacts with the histone chaperone HIRA complex and regulates nucleosome assembly and cellular senescence. Proc Natl Acad Sci U S A. Jun. 7, 2016;113(23):E3213-20.
Li et al., Overexpression of miR-584-5p inhibits proliferation and induces apoptosis by targeting WW domain-containing E3 ubiquitin protein ligase1 in gastric cancer. *J Exp Clin Cancer Res*, 36, 59 (2017).
Liu Y, Zhi Y, Song H, Zong M, Yi J, Mao G, Chen L, Huang G. S1PR1 promotes proliferation and inhibits apoptosis of esophageal squamous cell carcinoma through activating STATS pathway. J Exp Clin Cancer Res. Aug. 22, 2019;38(1):369.
Ma L, Young J, Prabhala H, Pan E, Mestdagn P, Mutn D, Teruya-Feldstein J, Reinhardt F, Onder1T,Valastyan S, Westermann F, Speleman F, Vandesompele J, Weinberg RA. miR-9, a MYC/MYCN-activated microRNA, regulates E-cadherin and cancer metastasis. Nat Cell Biol. Mar. 2010;12(3):247-56.
Mason, D., Jackson, T. & Lin, A. Molecular signature of oncogenic res-induced senescence. *Oncogene* 23, 9238-9246 (2004).
Pleiotrophin Suppression of Receptor Protein Tyrosine Phosphatase-β/ζ Maintains the Self-Renewal Competence of Fetal Human Oligodendrocyte Progenitor Cells, Crystal R. McClain, Fraser J. Sim, Steven A. Goldman, Journal of Neuroscience Oct. 24, 2012, 32(43) 15066-15075.
Murakami-Tonami, Y., Ikeda, H., Yamagishi, R. et al. SGO1 is involved in the DNA damage response in MYCN-amplified neuroblastoma cells. *Sci Rep* 6, 31615 (2016).
Nishiyama A, Lin XH, Giese N, Heldin CH, Stallcup WB. Co-localization of NG2 aroteoglycan and PDGF alpha-receptor on O2A progenitor cells in the developing rat brain. J Neurosci Res. Feb. 1, 1996;43(3):299-314.
Osipovitch M, Asenjo Martinez A, Mariani J., Human ESC-Derived Chimeric Mouse Models of Huntington's Disease Reveal Cell-Intrinsic Defects in Glial Progenitor Cell Differentiation, Cell Stem Cell, 2018; 24, 107-122.e7
Piper, Peter W., Gary W. Jones, David H. Bringloe, Nicholas Harris, Morag J MacLean and Mehdi Mollapour. The shortened replicative life span of prohibitin mutants of yeast appears to be due to defective mitochondrial segregation in old mother cells. Aging Cell, vol. 1, Issue 2, pp. 149-157.
Poudel SB, 80 H-S, Sim H-J, et al. Osteoblastic Wntless deletion dmerenuauy regulates the fate and functions of bone marrow-derived stem cells in relation to age. Stem Cells. 2021;39:103-114.
Rohrberg J, Van de Mark D, Amouzgar M, Lee JV, Taiteb M, Corella A, Kllmc S, Nilliams J, Jokisch ML, Camarda R, Balakrishnan S, Shankar R, Zhou A, Chang AN, Chen B, Rugo HS, Dumont S, Goga A. MYC Dysregulates Mitosis, Revealing Cancer Vulnerabilities. Cell Rep. Mar. 10, 2020;30(10):3368-3382.e7.
Shen S, Guo X, Yan H, Lu Y, Ji X, Li L, Liang T, Zhou D, Feng XH, Zhao JC, Yu J, Gong XG, Zhang L, Zhao B. A miR-130a-YAP positive feedback loop promotes organ size and tumorigenesis. Cell Res. Sep. 2015;25(9):997-1012.
Dae-Seop Shin, Hye-Nan Kim, Ki Deok Shin, Young Ju Yoon, Seung-Jun Kim, uong Cho Han, Byoung-Mog Kwon; Cryptotanshinone Inhibits Constitutive Signal Transducer and Activator of Transcription 3 Function through Blocking the Dimerization in DU145 Prostate Cancer Cells. *Cancer Res* Jan. 1, 2009; 69 (1): 193-202.
Siddiquee K, Zhang S, Guida WC, Blaskovich MA, Greedy B, Lawrence HR, Yip ML, Jove R, McLaughlin MM, Lawrence NJ, Sebti SM, Turkson J. Selective chemical probe inhibitor of Stat3, identified through structure-based virtual screening, induces antitumor activity. Proc Natl Acad Sci U S A. May 1, 2007;104(18):7391-6.
Sim, F., McClain, C., Schanz, S. et al. CD140a identifies a population of highly myelinogenic, migration-competent and efficiently engrafting human oligodendrocyte progenitor cells. *Nat Biotechnol* 29, 934-941 (2011).
Sim, F. et al., Complementary Patterns of Gene Expression by Human Oligodendrocyte Progenitors and their Environment Predict Determinants of Progenitor Maintenance and Differention, Annals of Neurology, vol. 59, issue 5 pp. 763-779.
Song F, Yang Y, Liu J. MicroRNA-548ac induces apoptosis in laryngeal squamous cell carcinoma cells by targeting transmembrane protein 158. Oncol Lett. Oct. 2020;20(4):69.
Sundar IK, Rashid K, Gerloff J, Rangel-Moreno J, Li D, Rahman I. Genetic ablation of histone deacetylase 2 leads to lung cellular senescence and lymphoid follicle formation in COPD/emphysema. FASEB J. Sep. 2018;32(9):4955-4971.
Dean G. Tang, Yasuhito M. Tokumoto, Martin C. Raff; Long-Term Culture of Purified Postnatal Oligodendrocyte Precursor Cells: Evidence for an Intrinsic Maturation Program That Plays out over Months. *J Cell Biol* Mar. 6, 2000; 148(5): 971-984.

(56) References Cited

OTHER PUBLICATIONS

Wang M, Wang X, Liu W. MicroRNA-130a-3p promotes the proliferation and inhibits he apoptosis of cervical cancer cells via negative regulation of RUNX3. Mol Med Rep. Oct. 2020;22(4):2990-3000.

Wang Y, Chen J, Wang X, Wang K. miR-140-3p inhibits bladder cancer cell proliferation and invasion by targeting FOXQ1. Aging (Albany NY). Oct. 24, 2020;12(20):20366-20379. doi: 10.18632/aging.103828.

Windrem MS, Schanz SJ, Guo M, Tian GF, Washco V, Stanwood N, Rasband M, Roy NS, Nedergaard M, Havton LA, Wang S, Goldman SA. Neonatal chimerization with human glial progenitor cells can both remyelinate and rescue the otherwise lethally hypomyelinated shiverer mouse. Cell Stem Cell. Jun. 5, 2008;2(6):553-65.

Yu et al., HMGA2 regulates the in vitro aging and proliferation of human umbilical Blood-Derived Stromal Cells Through the mTOR/p70SBK Signaling Pathway, Stem Cell Research, vol. 10, Issue 2,2013,pp. 156-165.

* cited by examiner

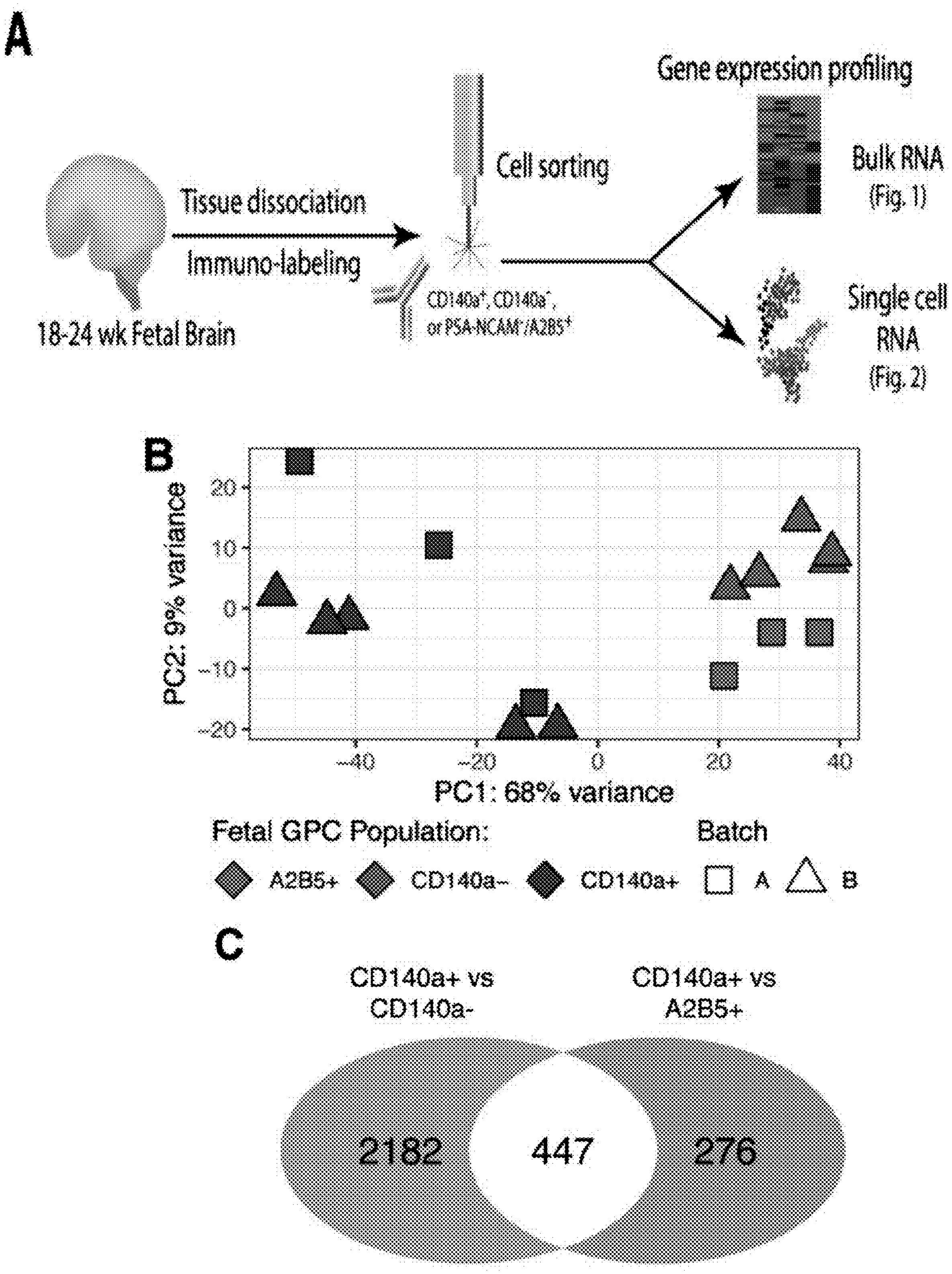
FIG. 1A, 1B, and 1C

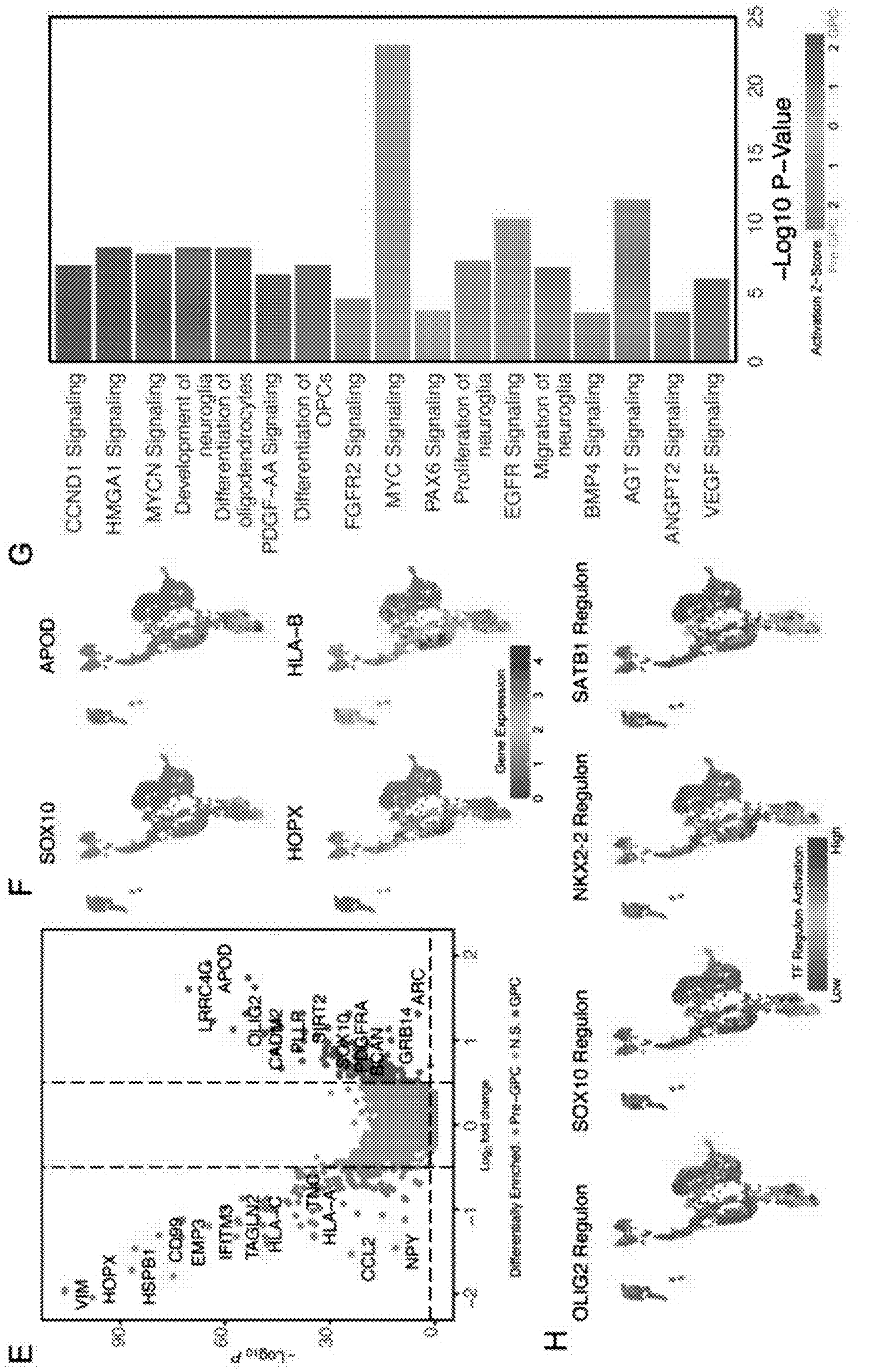
FIG. 2E, 2F, 2G, and 2H

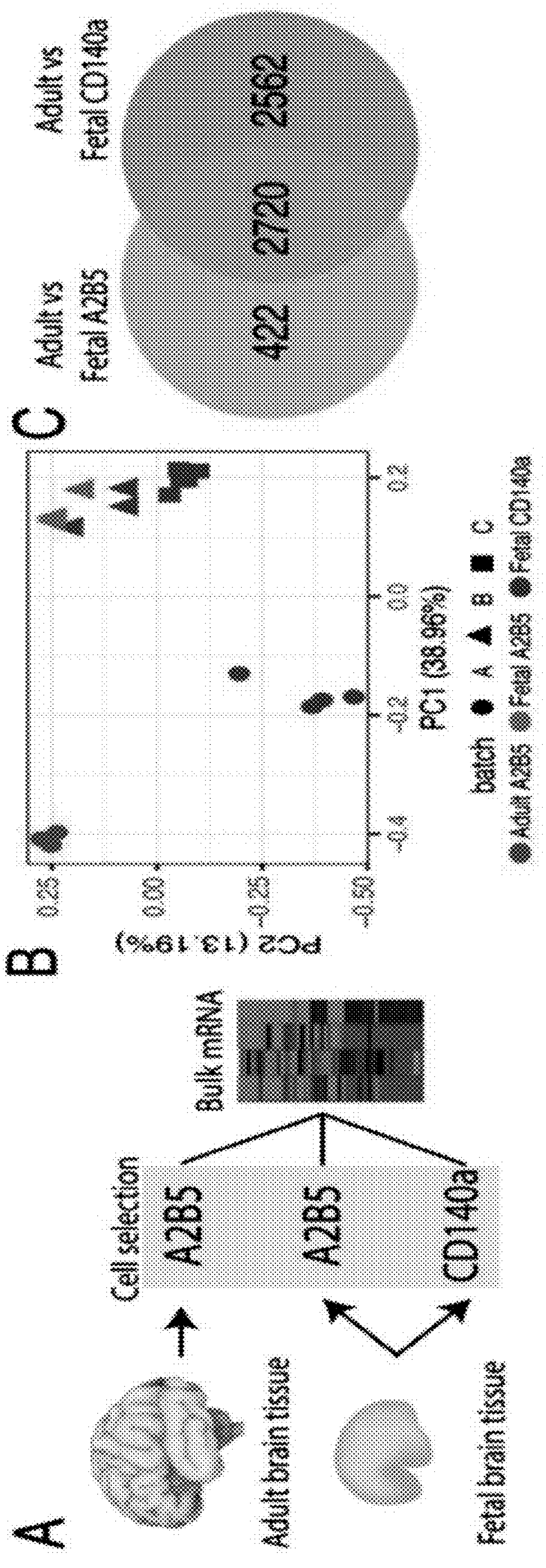
FIG. 3A, 3B, and 3C

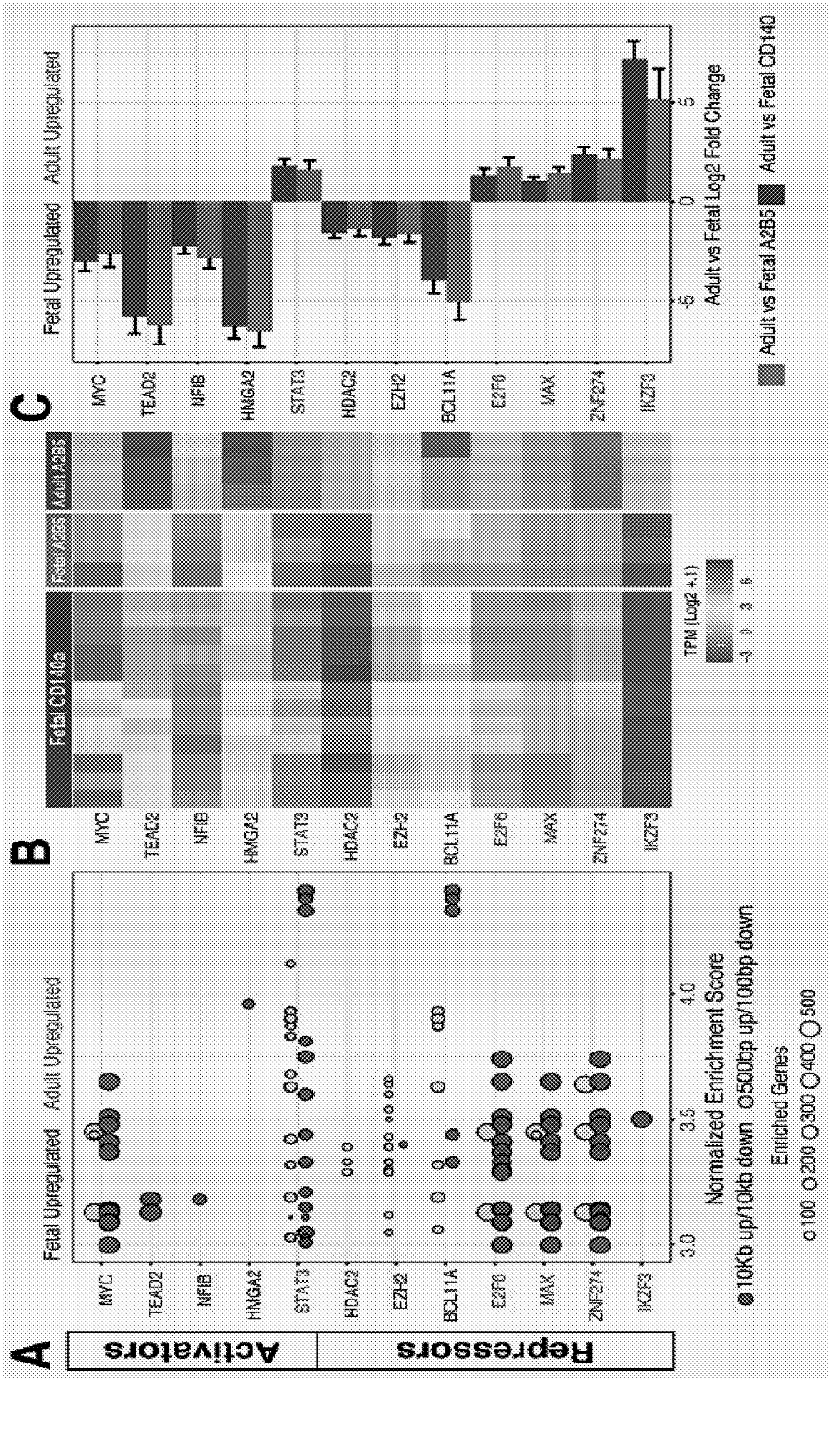
FIG. 4A, 4B, and 4C

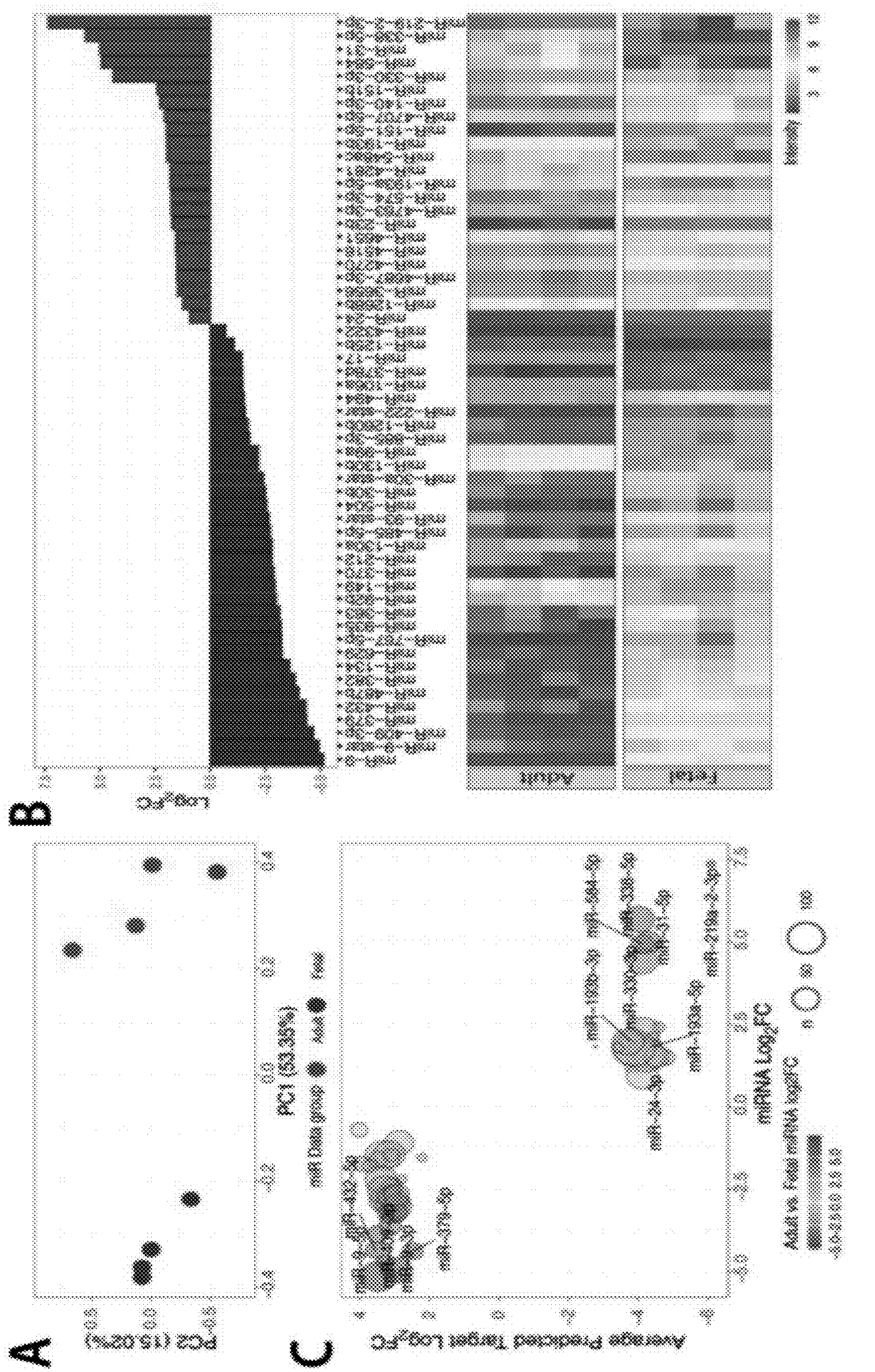
FIG. 6A, 6B, and 6C

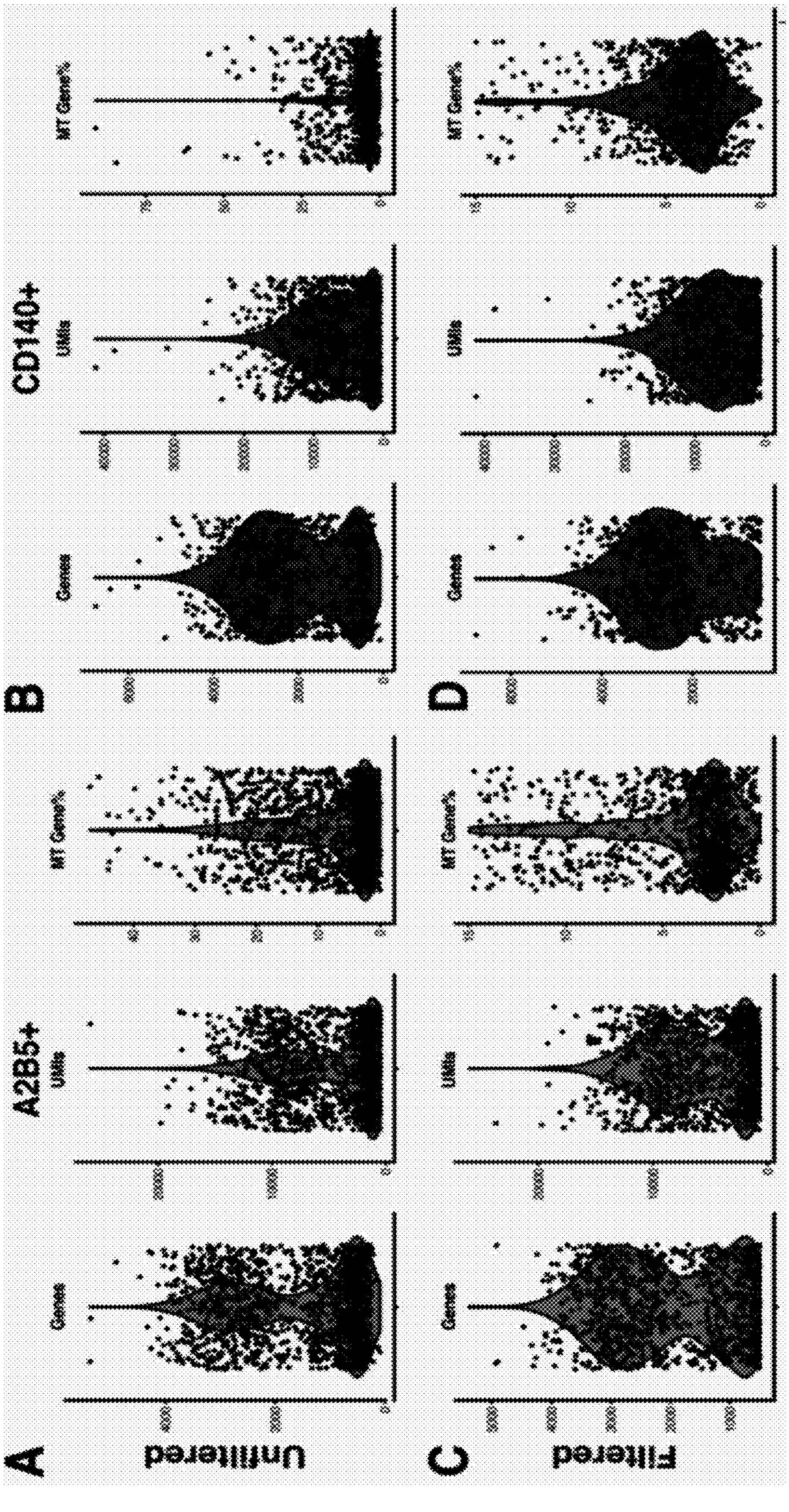
FIG. 8A, 8B, 8C, and 8D

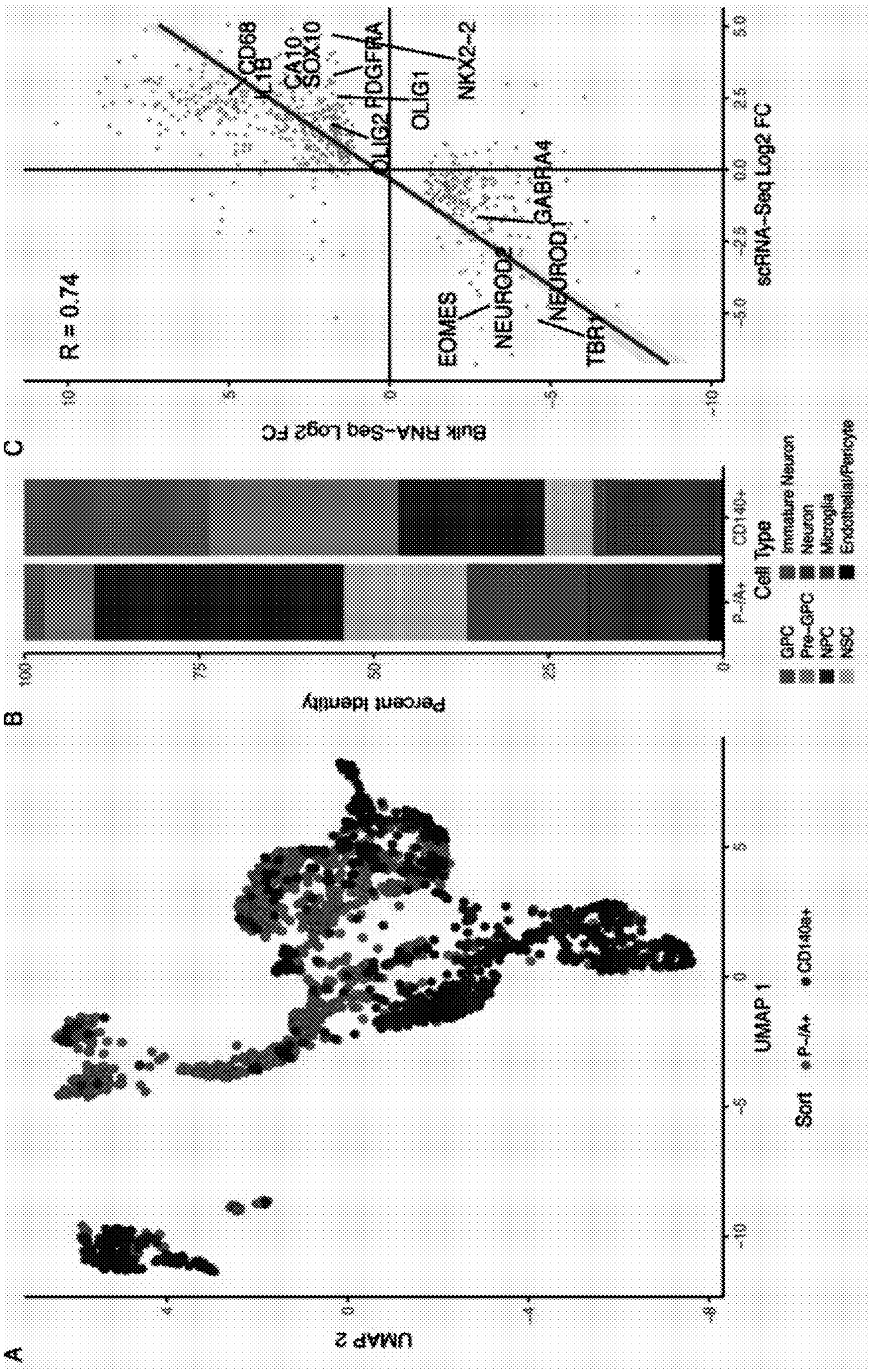
FIG. 9A, 9B, and 9C

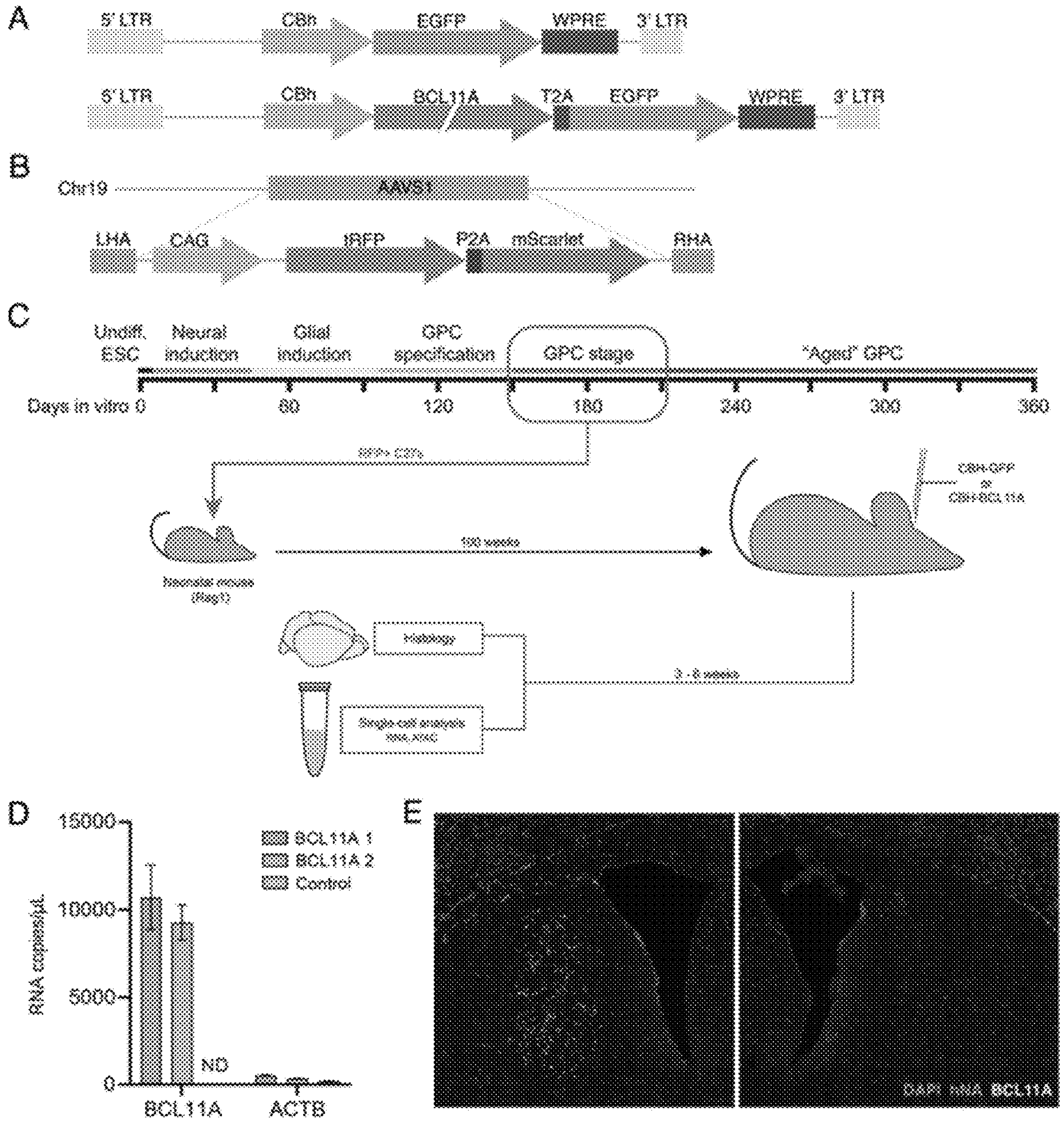
FIG. 14A, 14B, 14C, 14D, and 14E

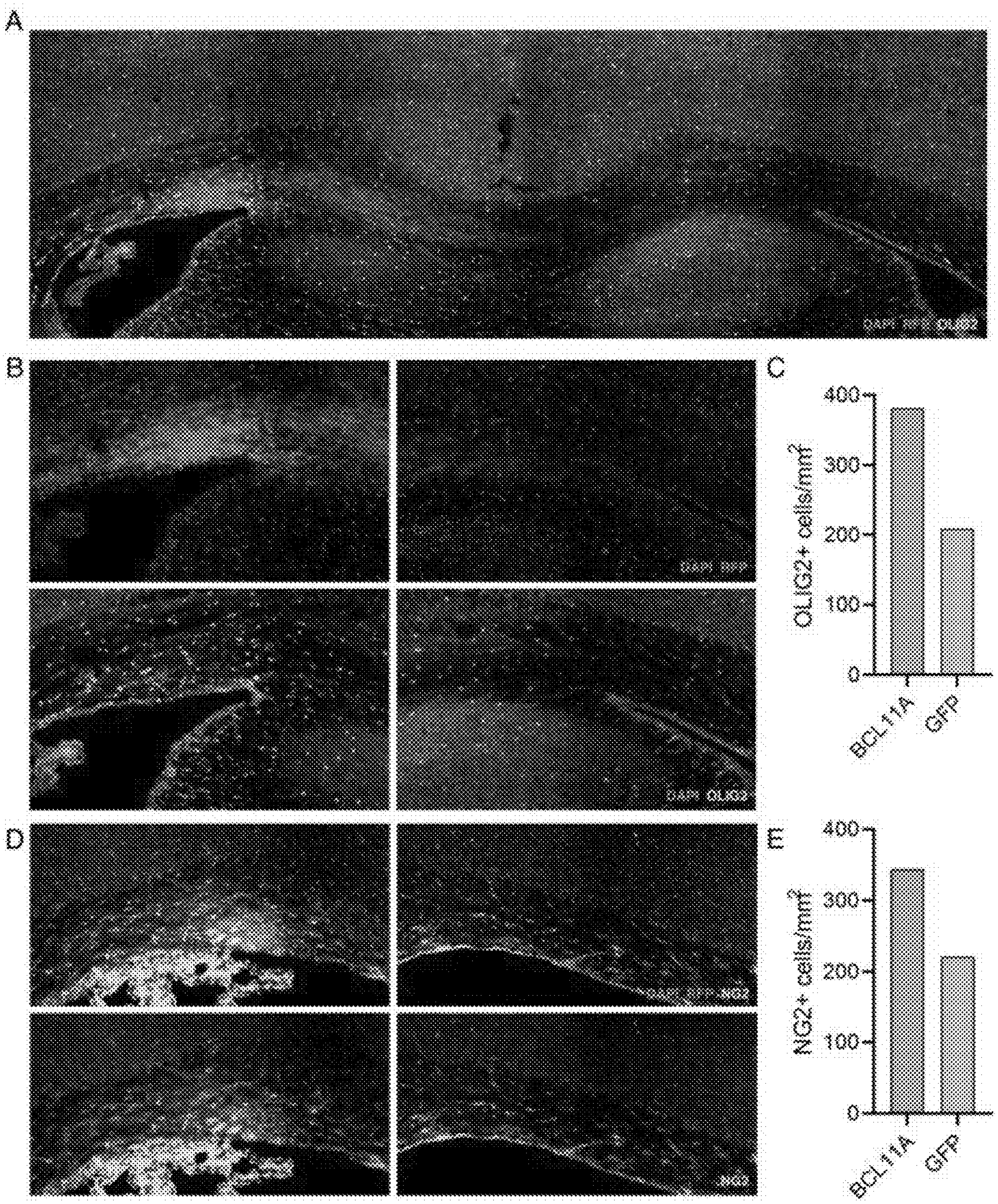
FIG. 15A, 15B, 15C, 15D, and 15E

SEQUENCE LISTING

```
Sequence total quantity: 21
SEQ ID NO: 1            moltype = RNA  length = 22
FEATURE                 Location/Qualifiers
source                  1..22
                        mol_type = other RNA
                        organism = Homo sapiens
SEQUENCE: 1
tgggtctttg cgggcgagat ga                                            22

SEQ ID NO: 2            moltype = RNA  length = 23
FEATURE                 Location/Qualifiers
source                  1..23
                        mol_type = other RNA
                        organism = Homo sapiens
SEQUENCE: 2
atcacattgc cagggattac cac                                           23

SEQ ID NO: 3            moltype = RNA  length = 21
FEATURE                 Location/Qualifiers
source                  1..21
                        mol_type = other RNA
                        organism = Homo sapiens
SEQUENCE: 3
tggctgttgg agggggcagg c                                             21

SEQ ID NO: 4            moltype = RNA  length = 20
FEATURE                 Location/Qualifiers
source                  1..20
                        mol_type = other RNA
                        organism = Homo sapiens
SEQUENCE: 4
cggggtgggt gaggtcgggc                                               20

SEQ ID NO: 5            moltype = RNA  length = 20
FEATURE                 Location/Qualifiers
source                  1..20
                        mol_type = other RNA
                        organism = Homo sapiens
SEQUENCE: 5
tcagggagtc aggggagggc                                               20

SEQ ID NO: 6            moltype = RNA  length = 22
FEATURE                 Location/Qualifiers
source                  1..22
                        mol_type = other RNA
                        organism = Homo sapiens
SEQUENCE: 6
tggctcagtt cagcaggaac ag                                            22

SEQ ID NO: 7            moltype = RNA  length = 22
FEATURE                 Location/Qualifiers
source                  1..22
                        mol_type = other RNA
                        organism = Homo sapiens
SEQUENCE: 7
agaggctggc cgtgatgaat tc                                            22

SEQ ID NO: 8            moltype = RNA  length = 21
FEATURE                 Location/Qualifiers
source                  1..21
                        mol_type = other RNA
                        organism = Homo sapiens
SEQUENCE: 8
tggtagacta tggaacgtag g                                             21

SEQ ID NO: 9            moltype = RNA  length = 22
FEATURE                 Location/Qualifiers
source                  1..22
                        mol_type = other RNA
                        organism = Homo sapiens
SEQUENCE: 9
tccctgagac cctaacttgt ga                                            22

SEQ ID NO: 10           moltype = RNA  length = 23
FEATURE                 Location/Qualifiers
source                  1..23
                        mol_type = other RNA
                        organism = Homo sapiens
```

```
SEQUENCE: 10
aaaagtgctt acagtgcagg tag                                   23

SEQ ID NO: 11          moltype = RNA  length = 23
FEATURE                Location/Qualifiers
source                 1..23
                       mol_type = other RNA
                       organism = Homo sapiens
SEQUENCE: 11
caaagtgctt acagtgcagg tag                                   23

SEQ ID NO: 12          moltype = RNA  length = 22
FEATURE                Location/Qualifiers
source                 1..22
                       mol_type = other RNA
                       organism = Homo sapiens
SEQUENCE: 12
cagtgcaatg ttaaaagggc at                                    22

SEQ ID NO: 13          moltype = RNA  length = 22
FEATURE                Location/Qualifiers
source                 1..22
                       mol_type = other RNA
                       organism = Homo sapiens
SEQUENCE: 13
cagtgcaatg atgaaagggc at                                    22

SEQ ID NO: 14          moltype = RNA  length = 22
FEATURE                Location/Qualifiers
source                 1..22
                       mol_type = other RNA
                       organism = Homo sapiens
SEQUENCE: 14
actgctgagc tagcacttcc cg                                    22

SEQ ID NO: 15          moltype = RNA  length = 19
FEATURE                Location/Qualifiers
source                 1..19
                       mol_type = other RNA
                       organism = Homo sapiens
SEQUENCE: 15
atcccaccac tgccaccat                                        19

SEQ ID NO: 16          moltype = RNA  length = 23
FEATURE                Location/Qualifiers
source                 1..23
                       mol_type = other RNA
                       organism = Homo sapiens
SEQUENCE: 16
tgcaccatgg ttgtctgagc atg                                   23

SEQ ID NO: 17          moltype = RNA  length = 22
FEATURE                Location/Qualifiers
source                 1..22
                       mol_type = other RNA
                       organism = Homo sapiens
SEQUENCE: 17
tgtaaacatc ctacactcag ct                                    22

SEQ ID NO: 18          moltype = RNA  length = 22
FEATURE                Location/Qualifiers
source                 1..22
                       mol_type = other RNA
                       organism = Homo sapiens
SEQUENCE: 18
ataaagctag ataaccgaaa gt                                    22

SEQ ID NO: 19          moltype = RNA  length = 23
FEATURE                Location/Qualifiers
source                 1..23
                       mol_type = other RNA
                       organism = Homo sapiens
SEQUENCE: 19
tctttggtta tctagctgta tga                                   23

SEQ ID NO: 20          moltype = DNA  length = 2319
FEATURE                Location/Qualifiers
source                 1..2319
                       mol_type = other DNA
```

-continued

```
                         organism = Homo sapiens
SEQUENCE: 20
atgtctcgcc gcaagcaagg caaaccccag cacttaagca aacgggaatt ctcgcccgag  60
cctcttgaag ccattcttac agatgatgaa ccagaccacg gcccgttggg agctccagaa  120
ggggatcatg acctcctcac ctgtgggcag tgccagatga acttcccatt gggggacatt  180
cttattttta tcgagcacaa acggaaacaa tgcaatggca gcctctgctt agaaaaagct  240
gtggataagc caccttcccc ttcaccaatc gagatgaaaa aagcatccaa tcccgtggag  300
gttggcatcc aggtcacgcc agaggatgac gattgtttat caacgtcatc tagaggaatt  360
tgccccaaac aggaacacat agcagataaa cttctgcact ggaggggcct ctcctcccct  420
cgttctgcac atggagctct aatccccacg cctgggatga gtgcagaata tgccccgcag  480
ggtatttgta aagatgagcc cagcagctac acatgtacaa cttgcaaaca gccattcacc  540
agtgcatggt ttctcttgca acacgcacag aacactcatg gattaagaat ctacttagaa  600
agcgaacacg gaagtcccct gaccccgcgg gttggtatcc cttcaggact aggtgcagaa  660
tgtccttccc agccacctct ccatgggatt catattgcag acaataaccc ctttaacctg  720
ctaagaatac caggatcagt atcgagagag gcttccggcc tggcagaagg gcgctttcca  780
cccactcccc ccctgtttag tccaccaccg agacatcact tggaccccca ccgcatagag  840
cgcctggggg cggaagagat ggccctggcc acccatcacc cgagtgcctt tgacagggtg  900
ctgcggttga atccaatggc tatggagcct cccgccatgg atttctctag gagacttaga  960
gagctggcag ggaacacgtc tagcccaccg ctgtccccag gccggcccag ccctatgcaa  1020
aggttactgc aaccattcca gccaggtagc aagccgccct tcctggcgac gccccccctc  1080
cctcctctgc aatccgcccc tcctccctcc cagccccogg tcaagtccaa gtcatgcgag  1140
ttctgcggca agacgttcaa atttcagagc aacctggtgg tgcaccggcg cagccacacg  1200
ggcgagaagc cctacaagtg caacctgtgc gaccacgcgt gcacccaggc cagcaagctg  1260
aagcgccaca tgaagacgca catgcacaaa tcgtccccca tgacggtcaa gtccgacgac  1320
ggtctctcca ccgccagctc cccggaaccc ggcaccagcg acttggtggg cagcgccagc  1380
agcgcgctca agtccgtggt ggccaagttc aagagcgaga acgaccccaa cctgatcccg  1440
gagaacgggg acgaggagga agaggaggac gacgaggaag aggaagaaga ggaggaagag  1500
gaggaggagg agctgacgga gagcgagagg gtggactacg gcttcgggct gagcctggag  1560
gcggcgcgcc accacgagaa cagctcgcgg ggcgcggtcg tgggcgtggg cgacgagagc  1620
cgcgccctgc ccgacgtcat gcagggcatg gtgctcagct ccatgcagca cttcagcgag  1680
gccttccacc aggtcctggg cgagaagcat aagcgcggcc acctggccga ggccgagggc  1740
cacagggaca cttgcgacga agactcggtg gccggcgagt cggaccgcat agacgatggc  1800
actgttaatg gccgcggctg ctccccgggc gagtcggcct cgggggcct gtccaaaaag  1860
ctgctgctgg gcagccccag ctcgctgagc cccttctcta agcgcatcaa gctcgagaag  1920
gagttcgacc tgcccccggc cgcgatgccc aacacggaga acgtgtactc gcagtggctc  1980
gccggctacg cggcctccag gcagctcaaa gatcccttcc ttagcttcgg agactccaga  2040
caatcgcctt ttgcctcctc gtcggagcac tcctcggaga acgggagctt gcgcttctcc  2100
acaccgcccg ggagctgga cggagggatc tcggggcgca gcggcacggg aagtggaggg  2160
agcacgcccc atattagtgg tccgggcccg ggcaggccca gctcaaaaga gggcagacgc  2220
agcgacactt gttcttcaca cacccccatt cggcgtagta cccagagagc tcaagatgtg  2280
tggcagtttt cggatggaag ctcgagagcc cttaagttc                        2319

SEQ ID NO: 21            moltype = AA  length = 773
FEATURE                  Location/Qualifiers
source                   1..773
                         mol_type = protein
                         organism = Homo sapiens
SEQUENCE: 21
MSRRKQGKPQ HLSKREFSPE PLEAILTDDE PDHGPLGAPE GDHDLLTCGQ CQMNFPLGDI  60
LIFIEHKRKQ CNGSLCLEKA VDKPPSPSPI EMKKASNPVE VGIQVTPEDD DCLSTSSRGI  120
CPKQEHIADK LLHWRGLSSP RSAHGALIPT PGMSAEYAPQ GICKDEPSSY TCTTCKQPFT  180
SAWFLLQHAQ NTHGLRIYLE SEHGSPLTPR VGIPSGLGAE CPSQPPLHGI HIADNNPFNL  240
LRIPGSVSRE ASGLAEGRFP PTPPLFSPPP RHHLDPHRIE RLGAEEMALA THHPSAFDRV  300
LRLNPMAMEP PAMDFSRRLR ELAGNTSSPP LSPGRPSPMQ RLLQPFQPGS KPPFLATPPL  360
PPLQSAPPPS QPPVKSKSCE FCGKTFKFQS NLVVHRRSHT GEKPYKCNLC DHACTQASKL  420
KRHMKTHMHK SSPMTVKSDD GLSTASSPEP GTSDLVGSAS SALKSVVAKF KSENDPNLIP  480
ENGDEEEEED DEEEEEEEEE EEEELTESER VDYGFGLSLE AARHHENSSR GAVVGVGDES  540
RALPDVMQGM VLSSMQHFSE AFHQVLGEKH KRGHLAEAEG HRDTCDEDSV AGESDRIDDG  600
TVNGRGCSPG ESASGGLSKK LLLGSPSSLS PFSKRIKLEK EFDLPPAAMP NTENVYSQWL  660
AGYAASRQLK DPFLSFGDSR QSPFASSSEH SSENGSLRFS TPPGELDGGI SGRSGTGSGG  720
STPHISGPGP GRPSSKEGRR SDTCSSHTPI RRSTQRAQDV WQFSDGSSRA LKF         773
```

METHODS AND COMPOSITIONS FOR REJUVENATING CNS GLIAL POPULATIONS BY SUPPRESION OF TRANSCRIPTION FACTORS

This application claims priority from U.S. provisional Nos. 63/257,827, filed Oct. 20, 2021, and 63/350,039, 63/350,041, 63/350,042, filed Jun. 8, 2022, which are incorporated herein by reference.

This invention was made with government support under NS110776 and AG072298 awarded by National Institutes of Health. The government has certain rights in the invention.

FIELD

This application relates to methods and compositions for rejuvenating CNS glial populations with an agent suppressing a transcription factor.

BACKGROUND

Glial progenitor cells (GPCs, also referred to as oligodendrocyte progenitor cells and NG2 cells) colonize the human brain during development, and persist in abundance throughout adulthood. During development, human GPCs (hGPCs) are highly proliferative bipotential cells, producing new oligodendrocytes and astrocytes (French-Constant and Raff, "Proliferating Bipotential Glial Progenitor Cells in Adult Rat Optic Nerve," Nature 319:499-502 (1986) and Raff et al., "A Glial Progenitor Cell that Develops in Vitro into an Astrocyte or an Oligodendrocyte Depending on Culture Medium," Nature 303:390-396 (1983)). In rodents, this capacity wanes during normal aging, with proliferation, migration, and differentiation competence all diminishing in aged GPCs (Chari et al., "Decline in Rate of Colonization of Oligodendrocyte Progenitor Cell (OPC)-depleted Tissue by Adult OPCs With Age," J. Neuropathol. Exp. Neurol. 62:908-916 (2003); Gao and Raff, "Cell Size Control and a Cell-intrinsic Maturation Program in Proliferating Oligodendrocyte Precursor Cells," J. Cell Biol. 138:1367-1377 (1997); Moyon et al., "TET1-mediated DNA Hydroxymethylation Regulates Adult Remyelination in Mice," Nature Communications 12:3359-3359 (2021); Segel et al., "Niche Stiffness Underlies the Ageing of Central Nervous System Progenitor Cells," Nature 573:130-134 (2019); Tang et al., "Long-Term Culture of Purified Postnatal Oligodendrocyte Precursor Cells. Evidence for an Intrinsic Maturation Program that Plays Out Over Months," J. Cell Biol. 148:971-984 (2000); Temple & Raff, "Clonal Analysis of Oligodendrocyte Development in Culture: Evidence for a Developmental Clock that Counts Cell Divisions," Cell 44:773-779 (1986); Wolswijk & Noble, "Identification of an Adult-Specific Glial Progenitor Cell," Development 105: 387-400 (1989); and Wren et al., "In Vitro Analysis of the Origin and Maintenance of O-2Aadult Progenitor Cells," J. Cell Biol. 116:167-176 (1992)). Similarly, it was previously found that adult human GPCs are less proliferative, less migratory, and more readily differentiated than their fetal counterparts when transplanted into congenitally dysmyelinated murine hosts (Windrem et al., "Fetal and Adult Human Oligodendrocyte Progenitor Cell Isolates Myelinate the Congenitally Dysmyelinated Brain," Nat. Med. 10:93-97 (2004)). Yet despite the manifestly different competencies of fetal and adult hGPCs, and the abundant data on GPC transcription in rodent models of aging (Bouhrara et al., "Evidence of Demyelination in Mild Cognitive Impairment and Dementia Using a Direct and Specific Magnetic Resonance Imaging Measure of Myelin Content," Alzheimers Dement. 14:998-1004 (2018); de la Fuente et al., "Changes in the Oligodendrocyte Progenitor Cell Proteome with Ageing," Mol. Cell Proteomics 19:1281-1302 (2020); Neumann et al., "Metformin Restores CNS Remyelination Capacity by Rejuvenating Aged Stem Cells," Cell Stem Cell 25:473-485 e478 (2019); and Spitzer et al., "Oligodendrocyte Progenitor Cells Become Regionally Diverse and Heterogeneous with Age," Neuron 101:459-471 e455 (2019)), little data are available that address changes in GPC gene expression during human aging (Perlman et al., "Developmental Trajectory of Oligodendrocyte Progenitor Cells in the Human Brain Revealed by Single Cell RNA Sequencing," Glia 68:1291-1303 (2020) and Sim et al., "Complementary Patterns of Gene Expression by Human Oligodendrocyte Progenitors and their Environment Predict Determinants of Progenitor Maintenance and Differentiation," Ann. Neurol. 59:763-779 (2006)), or that provide clear head-to-head comparisons of transcription by fetal and adult human GPCs.

The present disclosure is directed to overcoming deficiencies in the art.

SUMMARY

One aspect of the present application relates to a method of inducing rejuvenation in a population of adult glial progenitor cells. The method comprises the step of administering, to the population of adult glial progenitor cells, an effective amount of an agent that suppresses one or more transcription factors selected from the group consisting of (i) zinc finger protein 274 (ZNF274), (ii) Myc-associated factor X (MAX), (iii) E2F transcription factor 6 (E2F6), (iv) zinc finger protein Aiolos (IKZF3), and (v) signal transducer and activator of transcription 3 (STAT3).

Another aspect of the present application relates to a method of treating a subject having a glial cell-related disorder. The method comprises the step of administering, to the subject, an effective amount of an agent that suppresses one or more transcription factors selected from the group consisting of ZNF274, MAX, E2F6, IKZF3, and STAT3.

BRIEF DESCRIPTION OF THE DRAWINGS

The patent or application file contains at least one drawing executed in color. Copies of this patent or application with color drawing(s) will be provided by the Office upon request and payment of the necessary fee.

FIG. 8, which is related to FIG. 2, shows single cell RNA-Seq quality filtering: Violin plots of unfiltered Panel A. A2B5+/PSA−NCAM− and Panel B. CD140a scRNA-seq captures. Panel C-D, Violin plots following quality filtration (Percent mitochondrial gene expression <15% and >500 unique genes) of Panel C, A2B5+/PSA−NCAM− and Panel D, CD140a+ captures.

FIG. 9, which is related to FIG. 2, shows single cell RNA-sequencing of PSA−NCAM−/A2B5+ vs CD140a+ fetal hGPCs: Panel A. UMAP plot of A2B5+ and CD140a+ fetal hGPCs. Panel B. Frequency of cell types in each sorting paradigm isolate. Panel C. Scatter plot of differentially expressed bulk RNA-Seq log 2 fold changes vs pseudobulk log 2 fold changes between CD140a+ and A2B5+ fetal hGPC isolates.

FIG. 14 demonstrates: Panel A. Design of the CBh-BCL11 A-GFP and control CBh-GFP lentivirus. Panel B: Generation of CRISPR-Cas9-modified C27 iPSC line expressing tRFP-mScarlet from the AAVS1 locus. Panel C. Schematic depicting the experimental paradigm for long-term chimerization and BCL 11 A overexpression in Rag1 mice. Panel D. BCL11A overexpression via CBh-BCL11A-GFP confirmed in vitro by ddPCR and (Panel E) in vivo by immunohistochemistry.

FIG. 15 demonstrates: Panel A. A coronal section of a Rag1-C271RFP mouse corpus callosum (CC) three weeks after injection with CBh-BCL11A-GFP (L) or CBH-GFP (R). Panel B. Zoomed-in coronal sections of the CC, showing the difference in RFP-tagged human cells and OLIG2 between BCL11A-GFP and GFP-only hemispheres, quantified in Panel C). Panel D. Magnified coronal sections of the CC, showing the difference in RFP-lagged human cells and mouse NG2 between BCL11A-GFP and GFP-only hemispheres, quantified in Panel E).

Figures 16A, 16B:
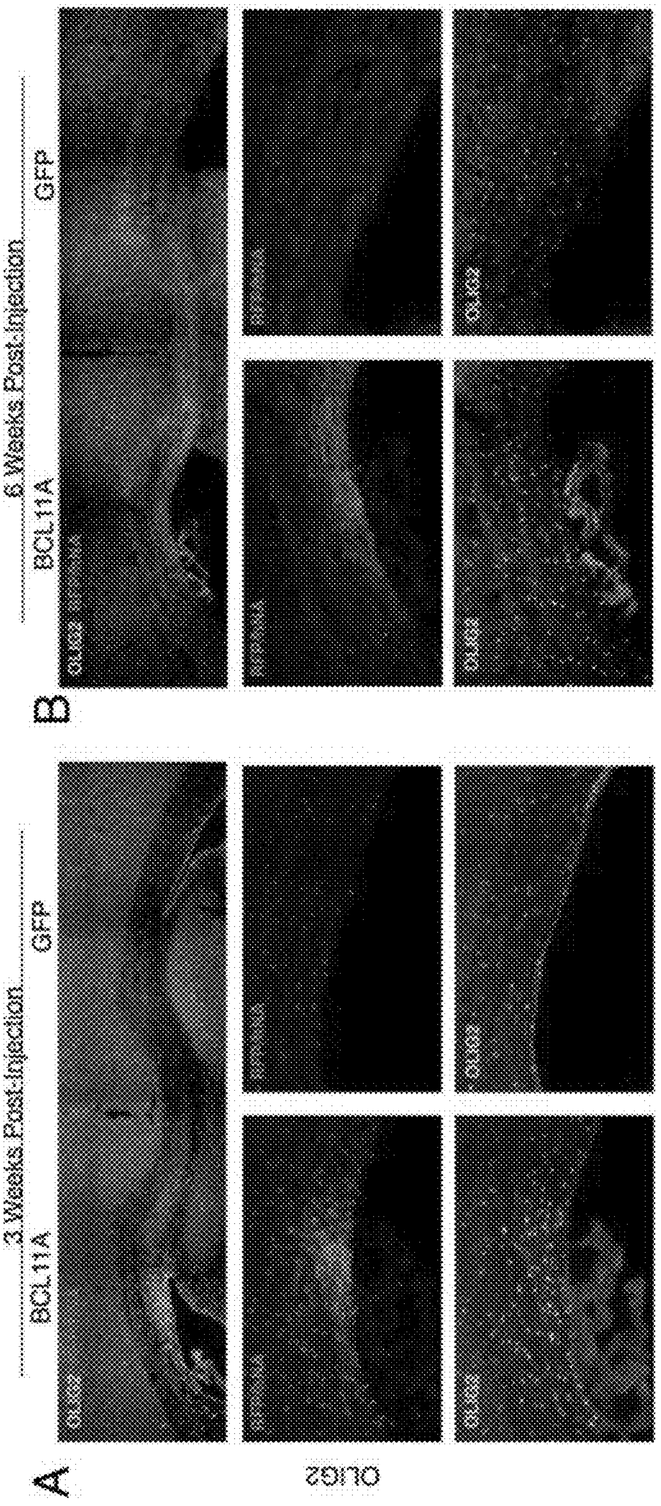
Figures 16C, 16D:
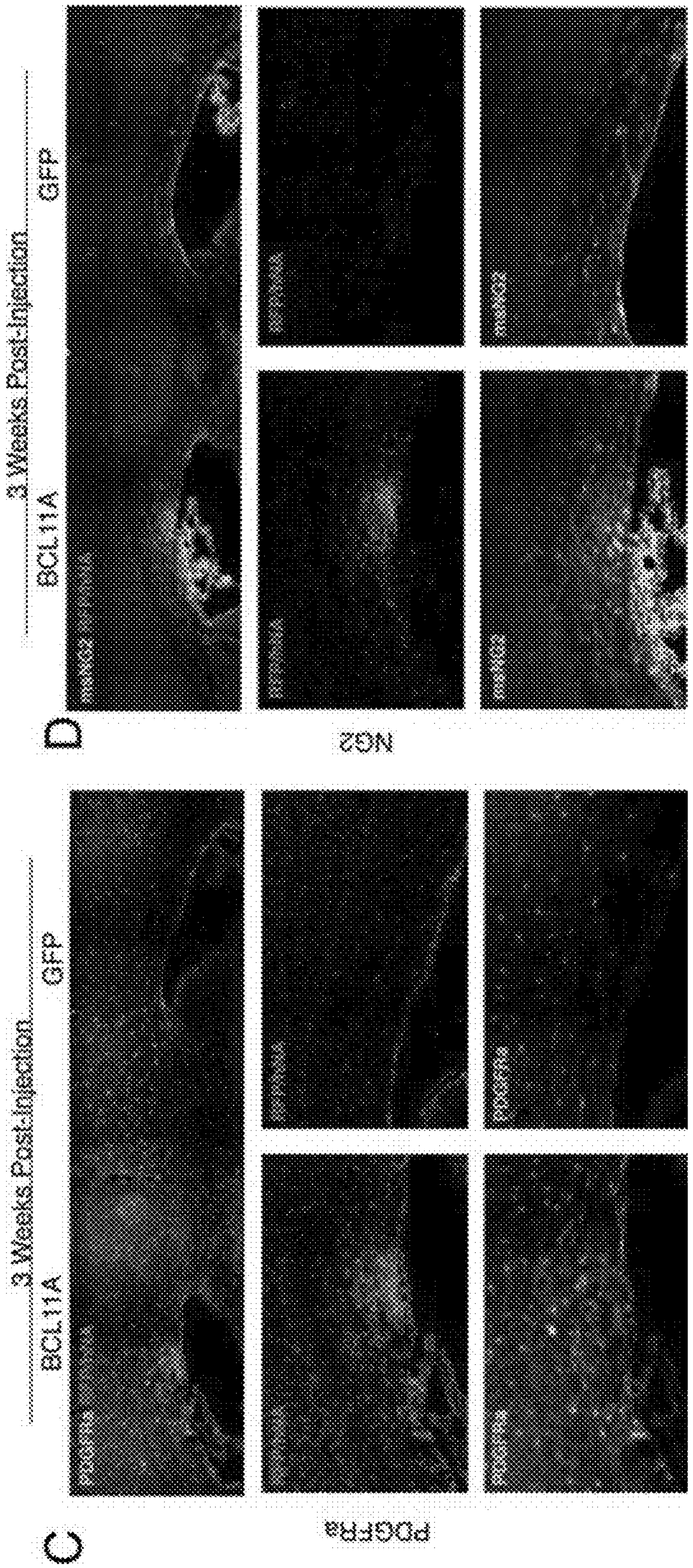

FIG. 16 demonstrates: Panel A. Coronal images of chimeric mouse corpus callosum (CC) three weeks after injection with CBh-BCL11A-GFP)L_ or CBh-GFP (R). Human cells are marked with tRFP/mScarlet and human nuclear antigen (hNA) in red, and OLIG2 is stained in green. Panel B. Coronal images of chimeric mouse CC six weeks after injection, human cells marked with tRFP/mScarlet and hNA in red, and OLIG2 in green. Panel C) Coronal images of chimeric mouse CC three weeks after injection, human cells marked with tRFP/mScarlet and hNA in red, and PDGFRa in green. Panel D. Coronal images of chimeric mouse CC three weeks after injection, human cells marked with tRFP/mScarlet and hNA in red, and mouse NG2 in green.

Figure 17:
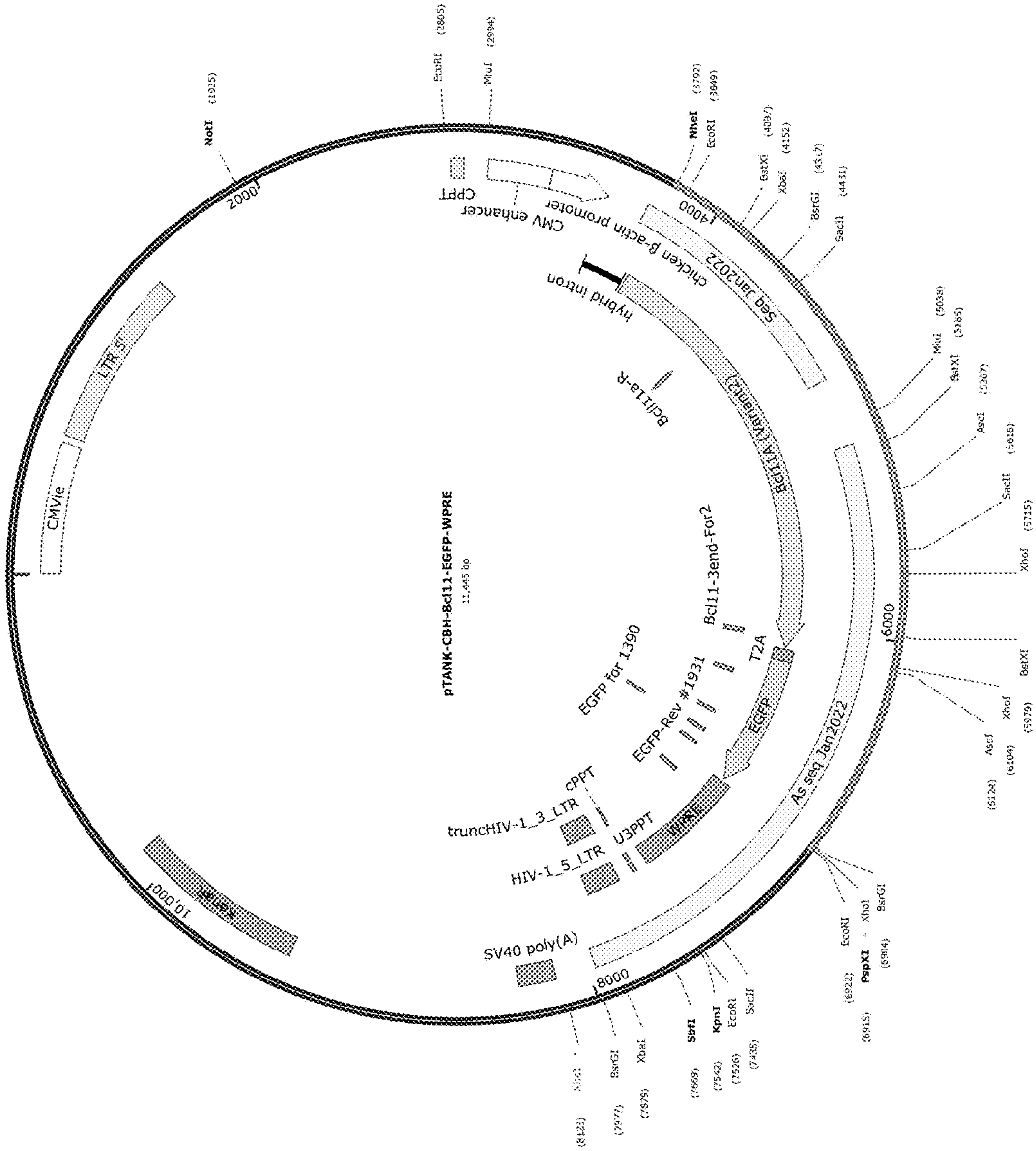

FIG. 17 shows an exemplary design of a BCL11A expression vector.

DETAILED DESCRIPTION

Reference will be made in detail to certain aspects and exemplary embodiments of the application, illustrating examples in the accompanying structures and figures. The aspects of the application will be described in conjunction with the exemplary embodiments, including methods, materials and examples, such description is non-limiting, and the scope of the application is intended to encompass all equivalents, alternatives, and modifications, either generally known, or incorporated here. The described aspects, features, advantages, and characteristics of the invention may be combined in any suitable manner in one or more further embodiments. One skilled in the relevant art will recognize that the invention may be practiced without one or more of the specific aspects or advantages of a particular embodiment. In other instances, additional aspects, features, and advantages may be recognized and claimed in certain embodiments that may not be present in all embodiments of the invention. Further, one skilled in the art will recognize many techniques and materials similar or equivalent to those described here, which could be used in the practice of the aspects and embodiments of the present application. The described aspects and embodiments of the application are not limited to the methods and materials described.

Unless otherwise defined, all technical and scientific terms used herein have the same meaning as commonly understood by one of ordinary skill in the art to which this application belongs.

As used in this specification and the appended claims, the singular forms "a," "an" and "the" include plural referents unless the content clearly dictates otherwise. Thus, for example, reference to "a peptide" includes "one or more" peptides or a "plurality" of such peptides.

I. Definitions

As used herein, the following terms or phrases (in parentheses) shall have the following meanings:

As used in this specification and the appended claims, the singular forms "a," "an" and "the" include plural referents unless the content clearly dictates otherwise. Thus, for example, reference to "a peptide" includes "one or more" peptides or a "plurality" of such peptides.

The term "about" or "approximately" includes being within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

The term "and/or" as used herein means that the listed items are present, or used, individually or in combination. In effect, this term means that "at least one of" or "one or more" of the listed items is used or present.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, and so on. As a non-limiting example, each range discussed herein can be readily broken down into a lower third, middle third and upper third, and so on. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "involving", "having", and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps. In embodiments or claims where the term comprising (or the like) is used as the transition phrase, such embodiments can also be envisioned with replacement of the term "comprising" with the terms "consisting of" or "consisting essentially of." The methods, kits, systems, and/or compositions of the present disclosure can comprise, consist essentially of, or consist of, the components disclosed.

In embodiments comprising an "additional" or "second" component, the second component as used herein is different from the other components or first component. A "third"

component is different from the other, first, and second components, and further enumerated or "additional" components are similarly different.

The term "complementary" when used in connection with nucleic acid, refers to the pairing of bases, A with T or U, and G with C. The term "complementary" refers to nucleic acid molecules that are completely complementary, that is, form A to T or U pairs and G to C pairs across the entire reference sequence, as well as molecules that are partially (e.g., at least 80%, 81%, 82%, 83%, 84%, 85%, 86%, 87%, 88%, 89%, 90%, 91%, 92%, 93%, 94%, 95%, 96%, 97%, 98%, or 99%) complementary.

The terms "nucleic acid", "nucleotide", and "polynucleotide" encompass both DNA and RNA unless specified otherwise.

The term "polypeptide," "peptide" or "protein" are used interchangeably and to refer to a polymer of amino acid residues. The terms encompass all kinds of naturally occurring and synthetic proteins, including protein fragments of all lengths, fusion proteins and modified proteins, including without limitation, glycoproteins, as well as all other types of modified proteins (e.g., proteins resulting from phosphorylation, acetylation, myristoylation, palmitoylation, glycosylation, oxidation, formylation, amidation, polyglutamylation, ADP-ribosylation, pegylation, biotinylation, etc.).

The terms "abrogate", "abrogation" "eliminate", or "elimination" of expression of a gene or gene product (e.g., RNA or protein) refers to a complete loss of the transcription and/or translation of a gene or a complete loss of the gene product (e.g., RNA or protein). Expression of a gene or gene product (e.g., RNA or protein) can be detected by standard art known methods such as those described herein, as compared to a control, e.g., an unmodified cell.

The terms "express" and "expression" mean allowing or causing the information in a gene or DNA sequence to become produced, for example producing an RNA or a protein by activating the cellular functions involved in transcription and/or translation of a corresponding gene or DNA sequence. A DNA sequence is expressed in or by a cell to form an "expression product" such as an RNA or a protein. The expression product itself, e.g., the resulting protein, may also be said to be "expressed" by the cell. An expression product can be characterized as intracellular, extracellular or transmembrane As used herein, the term "glial cells" refers to a population of non-neuronal cells that provide support and nutrition, maintain homeostasis, either form myelin or promote myelination, and participate in signal transmission in the nervous system. "Glial cells" as used herein encompasses fully differentiated cells of the glial lineage, such as oligodendrocytes or astrocytes, as well as glial progenitor cells, each of which can be referred to as macroglial cells.

As used herein, the term "adult glial progenitor cells" refers to glial progenitor cells that are present in a mammal at any developmental stage after birth. In some embodiments, the term "adult glial progenitor cells" refers to glial progenitor cells present in a human subject who is 1, 2, 3, 4, 5, 6, 7, 8, 9, 10, 11, 12, 13, 14, 15, 16, 17, or 18 years of age or older. In some embodiments, the term "adult glial progenitor cells" refers to glial progenitor cells present in a human subject who is 20 years of age or older, 25 years of age or older, 30 years of age or older, 35 years of age or older, 40 years of age or older, 45 years of age or older, or 50 years of age or older. In some embodiments, the term "adult glial progenitor cells" refers to glial progenitor cells present in a human subject of advanced age, such as an adult of 55 years of age or older, 60 years of age or older, 65 years of age or older, 70 years of age or older, 75 years of age or older, or 80 years of age or older.

The term "a functional variant" of a gene product (e.g., a transcription factor), refers to a modified transcription factor (e.g., by deletion, substitution, insertion, glycosylation, etc.) that retains at least 50% of the biological activity of the unmodified (wild-type) transcription factor in a competition assay.

The term "effective amount" refers to the amount of active compound or pharmaceutical agent that elicits the biological or medicinal response in a tissue, system, animal, individual or human that is being sought by a researcher, veterinarian, medical doctor or other clinician.

The term "regulatory sequence" or "regulatory element" refers to the nucleic acid sequences or elements that control, regulate, cause or permit expression of a gene to be regulated by such regulatory sequence or element. Regulatory elements/sequences may be found at the 5' or 3' side of the coding region, or within the coding region, or within introns, of the gene to be regulated. Examples of regulatory sequences/elements include, but are not limited to, promoters, enhancers, RNA polymerase initiation sites, ribosome binding sites, and other sequences that facilitate the expression of encoded polypeptides in a given expression system The term "promoter", as used herein, refers to a nucleotide sequence capable of controlling the expression of a coding sequence or functional RNA. In general, the polynucleotide of interest is located 3' of a promoter sequence. In some embodiments, the promoter is derived in its entirety from a native gene. In some embodiments, the promoter is composed of different elements derived from different naturally occurring promoters. In some embodiments, the promoter comprises a synthetic nucleotide sequence. It will be understood by those skilled in the art that different promoters will direct the expression of a gene in different tissues or cell types, or at different stages of development, or in response to different environmental conditions or to the presence or the absence of a drug or transcriptional co-factor. Ubiquitous, cell-type-specific, tissue-specific, developmental stage-specific, and conditional promoters, for example, drug-responsive promoters (e.g. tetracycline-responsive promoters) are well known to those of skill in the art. Examples of promoter include, but are not limited to, the phosphoglycerate kinase (PKG) promoter, CAG, NSE (neuronal specific enolase), synapsin or NeuN promoters, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), SFFV promoter, rous sarcoma virus (RSV) promoter, synthetic promoters, hybrid promoters, and the like. The promoters can be of human origin or from other species, including from mice. In addition, sequences derived from nonviral genes, such as the murine metallothionein gene promoter, will also find use herein. In some embodiments, the promoter is a heterologous promoter. In some embodiments, a promoter sequence consists of proximal and more distal upstream elements and can comprise an enhancer element.

The term "heterologous promoter", as used herein, refers to a promoter that does is not found to be operatively linked to a given encoding sequence in nature.

The term "enhancer" refers to a nucleotide sequence that can stimulate promoter activity and may be an innate element of the promoter or a heterologous element inserted to enhance the level or tissue-specificity of a promoter.

The term "operatively linked" or "operably linked" refers to the association of two or more nucleic acid fragments on a single nucleic acid fragment so that the function of one is affected by the other. For example, a promoter is operatively linked with a coding sequence when it is capable of affecting the expression of that coding sequence (e.g., the coding sequence is under the transcriptional control of the promoter). Encoding sequences can be operatively linked to regulatory sequences in sense or antisense orientation.

The term "transcription factor" refers to a DNA-binding protein that regulate the expression of specific genes.

A transcription factor can have a positive effect on gene transcription and, thus, may be referred to as a "transcription activator," "activator" or a "transcriptional activation factor." An exemplary activator (or transcriptional activation factor) is signal transducer and activator of transcription 3 (STAT3). As illustrated in FIG. 4F of the present disclosure, in the context of adult glial progenitor cells, STAT3 is predicted to activate a set of senescence-associated genes (e.g., BIN1, DMTF1, CD47, CTNNA1, RUNX2, RUNX1, MAP3K7, and OGT), glial cell-associated genes (e.g., PLP1, CNP, PMP22, SEMA4D, CLDN11, GPR37, MYRF, MAG, BCAS1, ST18, ERBB4, CERS2, LPAR1, and GJB1), and downstream transcription factors (e.g., MAX, E2F6, and IKZF3).

A transcription factor can also negatively affect gene expression and, thus, may be referred to as "transcription repressor," "repressor" or a "transcription repression factor." Exemplary repressors (or transcription repression factors) involved in glial progenitor cells senescence include, without limitation, ZNF274, MAX, E2F6, and IKZF3. As illustrated in FIG. 4G of the present disclosure, in the context of adult glial progenitor cells, ZNF274, MAX, E2F6, and IKZF3 are predicted to repress sets of proliferation-associated gene targets (e.g., YAP1, LMNB1, PATZ1, TEAD1, FN1, TP53, CDK1, CCND2, CDKN2D, CENPH, MKI67, CDK4, CENPF, CDK5, CDKN3, and CHEK1), glial cell-associated genes (e.g., CHRDL1, ST8SIA1, PTPRZ1, CA10, PDGFRA, BCAN, NXPH1, CSPG4, and, PCDH15), and downstream transcription factors (e.g., BLC11A, EZH2, HDAC2, NF1B, MYC, HMGA2, and TEAD).

The term "inhibitor of transcription factor" or "transcription factor repressor" refers to an agent that inhibits activity or expression of a transcription factor. An "inhibitor of transcription factor" or "transcription factor repressor" may be a small molecule, a polypeptide, a polynucleotide, such as an antisense oligonucleotide (ASO), a shRNA, or a miRNA.

Certain terms employed in the specification, examples, and claims are collected herein. Unless defined otherwise, all technical and scientific terms used in this disclosure have the same meanings as commonly understood by one of ordinary skill in the art to which this disclosure belongs.

Preferences and options for a given aspect, feature, embodiment, or parameter of the disclosure should, unless the context indicates otherwise, be regarded as having been disclosed in combination with any and all preferences and options for all other aspects, features, embodiments, and parameters of the disclosure.

II. Methods Involving the Activation of Transcription Factors

One aspect of the present application relates to a method of inducing rejuvenation in adult glial progenitor cells by activating certain transcription factors. In some embodiments, the method involves expressing, in the adult glial progenitor cells, an effective amount of one or more transcription factors selected from the group consisting of B-cell lymphoma/leukemia 11A (BCL11A), histone deacetylase 2 (HDAC2), histone-lysine N-methyltransferase EZH2 (EZH2), myc proto-oncogene protein (MYC), high 15 mobility group protein HMGI-C(HMGA2), nuclear factor 1 B-type (NFIB) and transcriptional enhancer factor TEF-4 (TEAD2).

As described herein, the term "rejuvenation" or "rejuvenating" refers to a reversion of the aging process in a cell and a return to youthful cell state, in particular with regard to proliferative and/or differentiation capacity, without loss of cell identity Adult glial progenitor cells suitable for use in the methods disclosed herein include mammalian glial progenitor cells, e.g., human glial progenitor cells, rodent glial progenitor cells, non-human primate glial progenitor cells, ovine glial progenitor cells, bovine glial progenitor cells, porcine glial progenitor cells, canine glial progenitor cells, and feline glial progenitor cells. In some embodiments, the adult glial progenitor cells are adult human glial progenitor cells.

In some embodiments, the glial progenitor cells are adult human glial progenitor cells. In some embodiments, the step of expressing is performed ex vivo. In some embodiments, the step of expressing is performed in vivo.

Another aspect of the application relates to a method of treating myelin deficiency in a subject by activating certain transcription factors in glial progenitor cells of the subject. In some embodiments, the method involves expressing, in glial progenitor cells of the subject, an effective amount of one or more transcription factors selected from the group consisting of BCL11A, HDAC2, EZH2, MYC, HMGA2, NFIB and TEAD2.

In some embodiments, the step of expressing is performed ex vivo. In some embodiments, the step of expressing is performed in vivo.

In accordance with this aspect of the present application, the myelin deficiency may be associated with a condition selected from the group consisting of multiple sclerosis, neuromyelitis optica, transverse myelitis, optic neuritis, subcortical stroke, diabetic leukoencephalopathy, hypertensive leukoencephalopathy, age-related white matter disease, spinal cord injury, radiation- or chemotherapy induced demyelination, post-infectious and post-vaccinial leukoencephalitis, periventricular leukomalacia, pediatric leukodystrophy (e.g., Pelizaeus-Merzbacher Disease, Tay-Sach Disease, Sandhoff's gangliosidoses, Krabbe's disease, metachromatic leukodystrophy, mucopolysaccharidoses, Niemann-Pick A disease, adrenoleukodystrophy, Canavan's disease, Vanishing White Matter Disease, and Alexander Disease), lysosomal storage diseases, congenital dysmyelination, inflammatory demyelination, vascular demyelination, and cerebral palsy.

In some embodiments, the myelin deficiency is associated with a neurodegenerative disease, e.g., Huntington's disease. As used herein, "Huntington's disease" refers to an autosomal dominant inherited brain disorder that typically becomes manifest in adulthood. Huntington's disease pathology is characterized by hypomyelination, as well as neuronal and white matter loss (see, e.g., Osipovitch et al., "Human ESC-Derived Chimeric Mouse Models of Huntington's Disease Reveal Cell-Intrinsic Defects in Glial Progenitor Cell Differentiation," Cell Stem Cell 24(1):107-122 (2019), which is hereby incorporated by reference in its entirety).

In other embodiments, the myelin deficiency is associated with a neuropsychiatric disease, e.g., schizophrenia. As used herein, "schizophrenia" refers to a condition typically characterized by a relative paucity of white matter and often frank hypomyelination (see, e.g., Windrem et al., "Human iPSC Glial Mouse Chimeras Reveal Glial Contributions to Schizophrenia," Cell Stem Cell 21(2):195-208 (2017), which is hereby incorporated by reference in its entirety).

As used hereinafter, the term, "treating" a subject having a myelin deficiency encompasses: (1) preventing, delaying, or reducing the incidence and/or likelihood of the appearance of at least one clinical or sub-clinical symptom of the myelin deficiency developing in a subject that may be afflicted with or predisposed to the myelin deficiency, but does not yet experience or display clinical or subclinical symptoms of the myelin deficiency; or (2) inhibiting the myelin deficiency, i.e., arresting, reducing or delaying the development of the myelin deficiency or a relapse thereof or at least one clinical or sub-clinical symptom thereof; or (3) relieving the myelin deficiency, i.e., causing regression of the myelin deficiency or at least one of its clinical or sub-clinical symptoms. The benefit to a subject to be treated is either statistically significant or at least perceptible to the patient or to the physician.

As used hereinafter, the term "subject" refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cat, or a dog. In some embodiments, the subject is a research animal. In some embodiments, the subject is genetically engineered, e.g., a genetically engineered non-human subject. The subject may be an adult subject. In some embodiments, the subject is at least 1 year old, least 2 year old, least 4 year old, least 6 year old, least 8 year old, least 10 year old, least 12 year old, least 15 year old, at least 18 years old, at least 20 years old, at least 25 years old, at least 30 years old, at least 35 years old, at least 40 years old, at least 45 years old, at least 50 years old, at least 55 years old, at least 60 years old, at least 65 years old, at least 70 years old, at least 75 years old, at least 80 years old, at least 85 years old, at least 90 years old, at least 95 years old, at least 100 years old, or more. In some embodiments, the subject is an adult subject between 18 to 100 years old, 20 to 100 years old, 30 to 100 years old, 40 to 100 years old, 50 to 100 years old, 50 to 100 years old, 60 to 100 years old, 70 to 100 years old, 80 to 100 years old, or 90 to 100 years old.

In some embodiments, the expressing step in the method of inducing rejuvenation in adult GPCs, or in the method of treating myelin deficiency in a subject, comprises administering to the adult GPCs or GPCs in the subject, respectively, one or more nucleic acid molecules encoding one or more transcription factors selected from the group consisting of BCL11A, HDAC2, EZH2, MYC, HMGA2, NFIB and TEAD2.

In some embodiments, the expressing step in the method of inducing rejuvenation in adult GPCs, or in the method of treating myelin deficiency in a subject, comprises administering to the adult GPCs or GPCs in the subject, respectively, one or more expression vectors that express one or more transcription factors selected from the group consisting of BCL11A, HDAC2, EZH2, MYC, HMGA2, NFIB and TEAD2, wherein each of the expression vector comprises (1) a nucleotide sequence encoding one or more transcription factors selected from the group consisting of BCL11A, HDAC2, EZH2, MYC, HMGA2, NFIB and TEAD2, and (2) a regulatory sequence operably linked to the nucleotide sequence.

As used herein, transcription factors mentioned in this application, such as BCL11A, HDAC2, EZH2, MYC, HMGA2, NFIB and TEAD2, include all transcript variants and functional variants thereof. Nucleotide sequences_encoding the one or more transcription factors identified herein are well known and accessible in the art. Table 1 below identifies the transcription factors, and their transcript variants by their gene name, Gene ID No., and NCBI Reference transcript accession number.

TABLE 1

Exemplary Human Genes and Transcript Variants

| Gene | Gene ID No.* | Transcript Variant | Reference Transcript Accession Nos.* |
|---|---|---|---|
| BAF chromatin remodeling complex subunit (BCL11A) | 53335 | transcript variant 3 | NM_138559.2 |
| | | transcript variant 2 | NM_018014.4 |
| | | transcript variant 4 | NM_001363864.1 |
| | | transcript variant X3 | XM_011532910.1 |
| | | transcript variant X1 | XM_011532909.1 |
| | | transcript variant 1 | NM_022893.4 |
| | | transcript variant 5 | NM_001365609.1 |
| | | transcript variant X7 | XM_024452962.1 |
| | | transcript variant X5 | XM_017004335.1 |
| | | transcript variant X2 | XM_017004333.1 |
| | | transcript variant X7 | XM_024452963.1 |
| | | transcript variant X8 | XM_017004336.1 |
| Histone deacetylase 2 (HDAC2) | 3066 | transcript variant 1 | NM_001527.4 |
| | | transcript variant 2 | NR_033441.2 |
| | | transcript variant 3 | NR_073443.2 |
| | | transcript variant X1 | XM_017010799.1 |
| Enhancer of Zeste 2 polycomb repressive complex 2 (EZH2) | 2146 | transcript variant 1 | NM_004456.5 |
| | | transcript variant 2 | NM_152998.3 |
| | | transcript variant 3 | NM_001203247.2 |
| | | transcript variant 4 | NM_001203248.2 |
| | | transcript variant 5 | NM_001203249.2 |
| | | transcript variant X3 | XM_005249962.4 |
| | | transcript variant X6 | XM_005249963.4 |
| | | transcript variant X21 | XM_005249964.4 |
| | | transcript variant X2 | XM_011515883.2 |
| | | transcript variant X4 | XM_011515884.2 |
| | | transcript variant X5 | XM_011515885.2 |
| | | transcript variant X7 | XM_011515886.2 |
| | | transcript variant X8 | XM_011515887.3 |
| | | transcript variant X9 | XM_011515888.2 |
| | | transcript variant X11 | XM_011515889.2 |
| | | transcript variant X12 | XM_011515890.2 |
| | | transcript variant X13 | XM_011515891.3 |
| | | transcript variant X14 | XM_011515892.2 |
| | | transcript variant X15 | XM_011515893.2 |
| | | transcript variant X17 | XM_011515894.2 |
| | | transcript variant X19 | XM_011515895.2 |
| | | transcript variant X22 | XM_011515896.2 |
| | | transcript variant X23 | XM_011515897.2 |
| | | transcript variant X24 | XM_011515898.2 |
| | | transcript variant X26 | XM_011515899.3 |
| | | transcript variant X30 | XM_011515901.3 |
| | | transcript variant X1 | XM_017011817.2 |
| | | transcript variant X10 | XM_017011818.1 |
| | | transcript variant X18 | XM_017011819.1 |
| | | transcript variant X20 | XM_017011820.2 |
| | | transcript variant X25 | XM_017011821.1 |
| | | transcript variant X16 | XM_024446680.1 |
| | | transcript variant X29 | XR_001744581.1 |
| | | transcript variant X27 | XR_002956413.1 |
| | | transcript variant X28 | XR_002956414.1 |
| MYC proto-oncogene, bHLH transcription factor (MYC) | 4609 | transcript variant 1 | NM_002467.6 |
| | | transcript variant 2 | NM_001354870.1 |

TABLE 1-continued

| Exemplary Human Genes and Transcript Variants | | | |
|---|---|---|---|
| Gene | Gene ID No.* | Transcript Variant | Reference Transcript Accession Nos.* |
| High mobility group AT hook 2 (HMAG2) | 8091 | transcript variant 1 | NM_003483.6 |
| | | transcript variant 2 | NM_003484.1 |
| | | transcript variant 3 | NM_001300918.1 |
| | | transcript variant 4 | NM_001300919.1 |
| | | transcript variant 5 | NM_001330190.1 |
| Nuclear Factor IB (NFIB) | 4781 | transcript variant 1 | NM_001190737.2 |
| | | transcript variant 3 | NM_005596.3 |
| | | transcript variant 2 | NM_001190738.2 |
| | | transcript variant 4 | NM_001282787.2 |
| | | transcript variant 5 | NM_001369458.1 |
| | | transcript variant 6 | NM_001369459.1 |
| | | transcript variant 7 | NM_001369460.1 |
| | | transcript variant 8 | NM_001369461.1 |
| | | transcript variant 9 | NM_001369462.1 |
| | | transcript variant 10 | NM_001369463.1 |
| | | transcript variant 11 | NM_001369464.1 |
| | | transcript variant 12 | NM_001369465.1 |
| | | transcript variant 13 | NM_001369466.1 |
| | | transcript variant 14 | NM_001369467.1 |
| | | transcript variant 15 | NM_001369468.1 |
| | | transcript variant 16 | NM_001369469.1 |
| | | transcript variant 17 | NM_001369470.1 |
| | | transcript variant 18 | NM_001369471.1 |
| | | transcript variant 19 | NM_001369472.1 |
| | | transcript variant 20 | NM_001369473.1 |
| | | transcript variant 21 | NM_001369474.1 |
| | | transcript variant 22 | NM_001369475.1 |
| | | transcript variant 23 | NM_001369476.1 |
| | | transcript variant 24 | NM_001369477.1 |
| | | transcript variant 25 | NM_001369478.1 |
| | | transcript variant 26 | NM_001369479.1 |
| | | transcript variant 27 | NM_001369480.1 |
| | | transcript variant 28 | NM_001369481.1 |
| | | transcript variant 29 | NR_161382.1 |
| | | transcript variant 30 | NR_161383.1 |
| | | transcript variant 31 | NR_161384.1 |
| | | transcript variant 32 | NR_161385.1 |
| | | transcript variant X1 | XM_005251467.3 |
| | | transcript variant X14 | XM_005251471.3 |
| | | transcript variant X2 | XM_006716773.3 |
| | | transcript variant X5 | XM_006716774.3 |
| | | transcript variant X6 | XM_006716775.3 |
| | | transcript variant X9 | XR_001746308.2 |
| | | transcript variant X10 | XR_001746309.2 |
| TEA Domain Transcription Factor 2 (TEAD2) | 8463 | transcript variant 3 | NM_001256660.2 |
| | | transcript variant 5 | NM_003598.2 |
| | | transcript variant 1 | NM_001256658.2 |
| | | transcript variant 2 | NM_001256659.2 |
| | | transcript variant 4 | NM_001256661.2 |
| | | transcript variant 6 | NM_001256662.2 |
| | | transcript variant X8 | XM_005259334.4 |
| | | transcript variant X7 | XM_006723428.3 |
| | | transcript variant X9 | XM_006723429.2 |
| | | transcript variant X1 | XM_011527399.2 |
| | | transcript variant X2 | XM_011527400.2 |
| | | transcript variant X3 | XM_011527401.1 |
| | | transcript variant X4 | XM_011527402.2 |
| | | transcript variant X5 | XM_011527403.1 |
| | | transcript variant X6 | XM_011527404.2 |
| | | transcript variant X10 | XM_011527405.3 |
| | | transcript variant XI1 | XM_011527406.3 |

*Each of which is hereby incorporated by reference in its entirety.

In some embodiments, the one or more expression vectors comprises an expression vector comprising a nucleotide sequence encoding BCL11A, a transcript variant or functional variant thereof. In some embodiments, the one or more expression vectors comprises an expression vector comprising a nucleotide sequence encoding the BCL11A variant of SEQ ID NO: 21. In some embodiments, the one or more expression vectors comprises an expression vector comprising the nucleotide sequence of SEQ ID NO:20.

In some embodiments, the one or more expression vectors comprises an expression vector comprising a nucleotide sequence encoding HDAC2, a transcript variant or functional variant thereof.

In some embodiments, the one or more expression vectors comprises an expression vector comprising a nucleotide sequence encoding EZH2, a transcript variant or functional variant thereof.

In some embodiments, the one or more expression vectors comprises an expression vector comprising a nucleotide sequence encoding MYC, a transcript variant or functional variant thereof.

In some embodiments, the one or more expression vectors comprises an expression vector comprising a nucleotide sequence encoding HMGA2, a transcript variant or functional variant thereof.

In some embodiments, the one or more expression vectors comprises an expression vector comprising a nucleotide sequence encoding HFIB, a transcript variant or functional variant thereof.

In some embodiments, the one or more expression vectors comprises an expression vector comprising a nucleotide sequence encoding TEAD2, a transcript variant or functional variant thereof.

In some embodiments, the expressing step in the method of inducing rejuvenation in adult GPCs, or in the method of treating myelin deficiency in a subject, comprises administering to the adult GPCs or GPCs in the subject, respectively, an effective amount of an inhibitor of a transcription factor repressor.

As used herein, the term "transcription factor repressor" refers to an agent that inhibits activity or expression of a transcription factor. A "transcription factor repressor" may be a polypeptide or a polynucleotide.

In some embodiments, the inhibitor of a transcription factor repressor is a small molecule.

In some embodiments, the inhibitor of a transcription factor repressor is a polypeptide or a polynucleotide. In some embodiments, the expressing step in the method of inducing rejuvenation in adult GPCs, or in the method of treating myelin deficiency in a subject, comprises administering to the adult GPCs or GPCs in the subject, respectively, an effective amount of an expression vector that comprises (1) a nucleotide sequence encoding an inhibitor of a transcription factor repressor, and (2) a regulatory sequence operably linked to the nucleotide sequence.

In some embodiments, the transcription factor repressor is aryl 20 hydrocarbon receptor (AHR). In accordance with such embodiments, the inhibitor of transcription factor repressor is an AHR inhibitor. In some embodiments, the AHR inhibitor is a small molecule inhibitor.

Suitable AHR inhibitors are known in the art and include, without limitation, a small molecule such as BAY-218 (see, e.g., Abstract 1288: Blocking Tumor Associated Immune Suppression with BAY-218, a Novel, Selective Aryl Hydrocarbon Receptor (AhR) Inhibitor," Proceedings of the American Association for Cancer 25 Research Annual Meeting 2019; 2019 Mar. 29-Apr. 3; Atlanta, GA. Philadelphia (PA): AACR; Cancer Res. 79(13 Suppl): Abstract nr 1288 (2019), which is hereby incorporated by reference in its entirety); perillaldehyde (see, e.g., Fuyuno et al., "Perillaldehyde Inhibits AHR Signaling and Activates NRF2 Antioxidant Pathway in Human Keratinocytes," Oxid. Med. Cell Longev. 2018:9524657 (2018), which is hereby incorporated by reference in its entirety); StemRegenin 1 (SR1) (see, e.g., Boitano et al., "Aryl Hydrocarbon Receptor Antagonists Promote the Expansion of Human Hematopoietic Stem Cells," Science 329(5997):1345-1348 (2010), which is hereby incorporated by reference in its entirety); KYN-101 (see, e.g., Campesato et al., "Blockade of the AHR Restricts a Treg-Macrophage Suppressive Axis Induced by L-5 Kynurenine," Nature Comm. 11:4011 (2020), which is hereby incorporated by reference in its entirety); CH-223191 (see, e.g., Kim et al., "Novel Compound 2-Methyl-2H-Pyrazole-3-Carboxylic acid (2-Methyl-4-o-Tolylazo-Phenyl)-Amide (CH-223191) Prevents 2,3,7,8-TCDD-Induced Toxicity by Antagonizing the Aryl Hydrocarbon Receptor," Mol. Pharmaocl. 69(6):1871-1878 (2006), which is hereby incorporated by 10 reference in its entirety); BAY 2416964 (see, e.g., International Patent Publication No. WO/2018/146010 to Bayer Aktiengesellschaft et al., which is hereby incorporated by reference in its entirety); PDM2 (see, e.g., de Medina et al., "Synthesis and Biological Properties of New Stilbene Derivatives of Resveratrol as New Selective Aryl Hydrocarbon Modulators," J. Med. Chem. 48:287-291 (2005), which is hereby 15 incorporated by reference in its entirety), and GNF351 (see, e.g., Smith et al., "Identification of a High-Affinity Ligand that Exhibits Complete Aryl Hydrocarbon Receptor Antagonism," J. Pharmacol. Exp. Ther. 338(1):318-327 (2011), which is hereby incorporated by reference in its entirety). Exemplary AHR small molecule inhibitors are shown in Table 2 below.

TABLE 2

| | Exemplary AHR Small Molecule Inhibitors |
|---|---|
| aryl hydrocarbon receptor (AHR) | 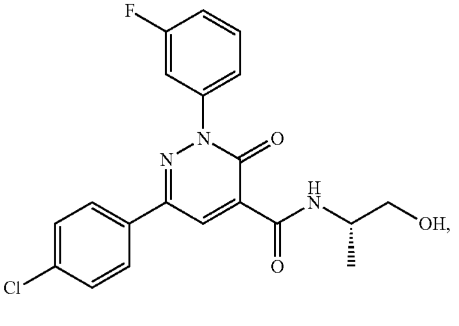 [SMILES: C[C@@H](CO)NC(=O)c1cc(-c2ccc(Cl)cc2)nn(-c2cccc(F)c2)c1=O]<br>BAY-218 |
| | 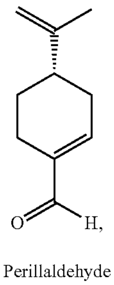<br>Perillaldehyde |
| | 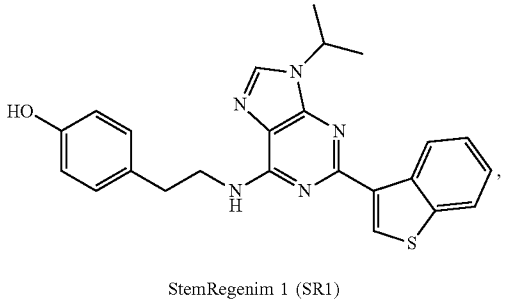<br>StemRegenim 1 (SR1) |

TABLE 2-continued

| Exemplary AHR Small Molecule Inhibitors |
|---|
| 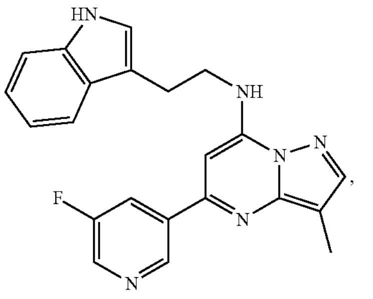 [SMILES: Cc1cnn2c(NCCc3c[nH]c4ccccc34)cc(-c3cncc(F)c3)nc12]<br>KYN-101 |
| 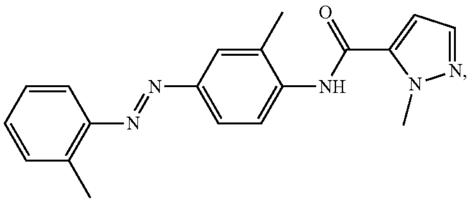 [SMILES: Cc1ccccc1/N=N/c1ccc(NC(=O)c2ccnn2C)c(C)c1]<br>CH-223191 |
| 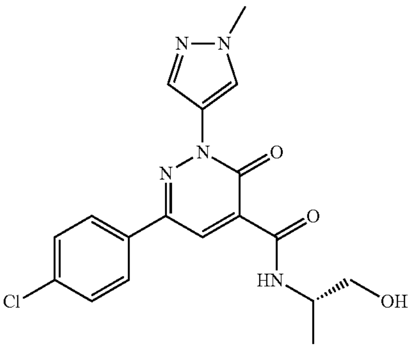 [SMILES: C[C@@H](CO)NC(=O)c1cc(-c2ccc(Cl)cc2)nn(-c2cnn(C)c2)c1=O]<br>BAY 2416964 |
| 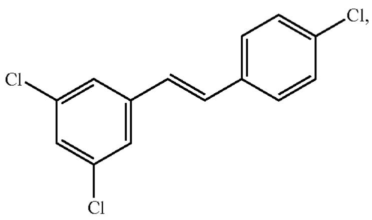 and<br>PDM2 |

TABLE 2-continued

| Exemplary AHR Small Molecule Inhibitors |
| --- |
| 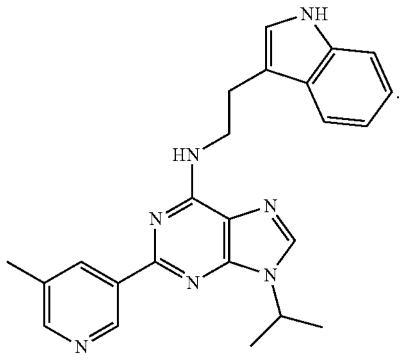 [SMILES: Cc1cncc(-c2nc(NCCc3c[nH]c4ccccc34)c3ncn(C(C)C)c3n2)c1] |
| GNF351 |

In some embodiments, the transcription factor repressor is Myc box-dependent-interacting protein (BIN1). In accordance with such embodiments, the inhibitor of a transcription factor repressor is a BIN1 inhibitor.

In some embodiments, the transcription factor repressor is a miRNA molecule. In accordance with such embodiments, the inhibitor of a transcription factor repressor is an inhibitor of miRNA. As described herein, miRNAs that function as transcription factor repressors include, without limitation, those identified in Table 3 below.

TABLE 3

Exemplary Human miRNA Transcription factor Repressors

| miRNA | Sequence | SEQ ID NO: |
| --- | --- | --- |
| miR-193a-5p | UGGGUCUUUGCGGGCGAGAUGA | 1 |
| miR-23b-3p | AUCACAUUGCCAGGGAUUACCAC | 2 |
| miR-4687-3p | UGGCUGUUGGAGGGGGCAGGC | 3 |
| miR-4651 | CGGGGUGGGUGAGGUCGGGC | 4 |
| miR-4270 | UCAGGGAGUCAGGGGAGGGC | 5 |
| miR-24-3p | UGGCUCAGUUCAGCAGGAACAG | 6 |

In some embodiments, the inhibitor of a transcription factor repressor is an inhibitor of any one or more of the above identified miRNAs (target miRNAs). Inhibitors of miRNA are known in the art as "antagomirs". An antagomir is an RNA oligonucleotide or RNA oligonucleotide mimetic having complementarity to a specific miRNA, and which inhibits the activity of that miRNA.

In some embodiments, the inhibitor of a transcription factor repressor is an antagomir targeting one or more of the miRNAs listed in Table 3. The antagomir may comprise 1, 2, 3, 4, 5, 6, 7, 8, 9 or 10 nucleotide differences from the complementary sequence of the miRNA that it inhibits. Further, antagomirs may have the same length, a longer length, or a shorter length than the miRNA that they inhibit. In certain embodiments, the antagomir hybridizes to 6-8 nucleotides at the 5' end of the miRNA it inhibits. In other embodiments, the antagomir is complementary to a miRNA is 5, 6, 7, 8, 9, 10, 11, 12, 13, 14, 15, 16, 17, 18, 19, 20, 21, 22, 23, 24, 25, 27, 28, 29, 30, 31, 32, 33, 34, 35, 36, 37, 38, 39, 40, 41, 42, 43, 44, 45, 46, 47, 48, 49 or 50 nucleotides in length. In other embodiments, the antagomir is 5-10, 6-8, 10-20, 10-15 or 5-500 nucleotides in length.

In some embodiments, the antagomir is a synthetic reverse complement of a target RNA that tightly binds to and inactivates the target miRNA. Thus, in some embodiments, the antagomir specifically inhibits or bocks the expression or activity of the target miRNA.

In some embodiments, the antagomir is at least 90%, at least 91%, at least 92%, at least 93%, at least 94%, at least 95%, at least 96%, at least 97%, at least 98%, at least 99%, or 100% complimentary to any one of the miRNA sequence provided in Table 3 above.

In some embodiments, the antagomir is capable of inhibiting the expression of one or more miRNAs disclosed in Table 3.

In particular, the antagomirs of the present application may be substantially complementary to nucleic acid sequence specific to miRNA selected from miR-193a-5p, miR-23b-3p, miR-4687-3p, miR-4651, miR-4270, or miR-24-3p, or to a portion thereof. Accordingly, nucleic acids or analogs thereof displaying substantially equivalent or altered activity are likewise contemplated.

In some embodiments, the antagomir comprises chemical modifications which improve nuclease resistance and binding affinity. Suitable modifications include, without limitation, 2' sugar modifications, such as 2'-O-Me, 2'-O-methoxyethyl(2'-MOE), or 2'-fluoro (2'-F).

In some embodiments, the expressing step in the method of inducing rejuvenation in adult GPCs, or in the method of treating myelin deficiency in a subject, comprises administering to the adult GPCs or GPCs in the subject, respectively, an effective amount of (1) an inhibitor of a transcription factor repressor, and/or (2) an effective amount of one or more transcription factors selected from the group consisting of B-cell lymphoma/leukemia 11A (BCL11A), histone deacetylase 2 (HDAC2), histone-lysine N-methyltransferase EZH2 (EZH2), myc proto-oncogene protein (MYC), high 15 mobility group protein HMGI-C(HMGA2), nuclear factor 1 B-type (NFIB) and transcriptional enhancer factor TEF-4 (TEAD2).

In some embodiments, the expressing step in the method of inducing rejuvenation in adult GPCs, or in the method of treating myelin deficiency in a subject, comprises administering to the adult GPCs or GPCs in the subject, respectively, an effective amount of (1) an expression vector encoding an inhibitor of a transcription factor repressor, and/or (2) an effective amount of an expression vector encoding one or more transcription factors selected from the group consisting of B-cell lymphoma/leukemia 11A (BCL11A), histone deacetylase 2 (HDAC2), histone-lysine N-methyltransferase EZH2 (EZH2), myc proto-oncogene protein (MYC), high 15 mobility group protein HMGI-C(HMGA2), nuclear factor 1 B-type (NFIB) and transcriptional enhancer factor TEF-4 (TEAD2).

In some embodiments, the regulatory sequence of the expression vector described above in the method of inducing rejuvenation in adult GPCs, or in the method of treating myelin deficiency in a subject, comprises a promoter and/or enhancer for a gene selectively or specifically expressed by glial progenitor cells.

Genes selectively expressed by glial progenitor cells include platelet 25 derived growth factor alpha (PDGFRA), zinc finger protein 488 (ZNF488), G protein-coupled receptor (GPR17), oligodendrocyte Transcription Factor 2

(OLIG2), chondroitin sulfate proteoglycan 4 (CSPG4), and SRY-box transcription factor 10 (SOX10).

In accordance with such embodiments, promoter sequences suitable for controlling expression of the nucleic acid inhibitors disclosed herein include, without limitation, the platelet derived growth factor alpha (PDGFRA) promoter, the zinc finger protein 488 (ZNF488) promoter, the G protein-coupled receptor (GPR17) promoter, the oligodendrocyte Transcription Factor 2 (OLIG2) promoter, the chondroitin sulfate proteoglycan 4 (CSPG4) promoter, and the SRY-box transcription factor 10 (SOX10) promoter, which are identified in Table 4 below.

TABLE 4

Exemplary Genes which are Selectively or Specifically Expressed by Glial Progenitor Cells

| Gene | Organism | Gene ID No.* | NCBI Reference Sequence:* |
|---|---|---|---|
| Platelet derived growth factor alpha (PDGFRA) | *Homo sapiens* | 5156 | NG_009250.1 |
| Zinc finger protein 488 (ZNF488) | *Homo sapiens* | 118738 | |
| G protein-coupled receptor (GPR17) | *Homo sapiens* | 2840 | NG_042235.1 |
| Oligodendrocyte Transcription Factor 2 OLIG2) | *Homo sapiens* | 10215 | NG_011834.1 |
| chondroitin sulfate proteoglycan 4 (CSPG4) | *Homo sapiens* | 1464 | |
| SRY-box transcription factor 10 (SOX10) | *Homo sapiens* | 6663 | NG_007948.1 |

*Each of which is hereby incorporated by reference in its entirety.

In some embodiments, the regulatory sequence of the expression vector described above in the method of inducing rejuvenation in adult GPCs, or in the method of treating myelin deficiency in a subject, comprises an inducible promoter or promoter system, such as tetracycline controlled inducible system, cumate-controlled inducible system and rapamycin controlled inducible systems, which are described in more detail infra.

In some embodiments, the expression vector described above in the method of inducing rejuvenation in adult GPCs, or in the method of treating myelin deficiency in a subject, is a plasmid vector, a viral vector, or a bacterial vector.

In some embodiments, the expression vector described above in the method of inducing rejuvenation in adult GPCs, or in the method of treating myelin deficiency in a subject, is a viral vector selected from the group consisting of adenoviruses, adeno-associated viruses (AAVs), retroviruses, lentiviruses, vaccinia viruses, and herpes viruses. In some embodiments, the expression vector is a lentiviral vector. In some embodiments, the expression vector is a retroviral vector. In other embodiments, the expression vector is an AAV vector. Methods for generating and isolating viral vectors suitable for use as expression vectors are described in more details infra.

III. Methods Involving the Suppression of Transcription Factors

Another aspect of the present application relates to a method of inducing rejuvenation in a population of adult glial progenitor cells by suppressing certain transcription factors. The method involves administering, to the population of adult glial progenitor cells, an effective amount of an agent that suppresses one or more transcription factor selected from the group consisting of zinc finger protein 274 (ZNF274), Myc-associated factor X (MAX), E2F transcription factor 6 (E2F6), zinc finger protein Aiolos (IKZF3), and signal transducer and activator of transcription 3 (STAT3).

Another aspect of the present application relates to a method of inducing rejuvenation in a population of adult glial progenitor cells by suppressing certain senescence genes. The method involves administering, to the population of adult glial progenitor cells, an effective amount of an agent that inhibits expression of one or more senescence genes selected from the group consisting of RUNX1, BIN1, VAMP3, DMTF1, CTNNA1, SERPINE1, CDK19, CDKNIC, RUNX2, EFEMP1, MAP3K7, AHR, OGT, PAK1, CBX7, and CYLD.

Another aspect of the present application relates to a method of inducing rejuvenation in a population of adult glial progenitor cells by suppressing certain senescence genes. The method involves administering, to the population of adult glial progenitor cells, an effective amount of an agent that inhibits expression of one or more glial target genes selected from the group consisting of MBP, CD9, ENPP2, PLP1, ERBIN, ZNF365, UGT8, GDNF, DUSP10, PMP22, ERBB4, and MYRF.

Adult glial progenitor cells suitable for use in the methods disclosed herein include mammalian glial progenitor cells, e.g., human glial progenitor cells, rodent glial progenitor cells, non-human primate glial progenitor cells, ovine glial progenitor cells, bovine glial progenitor cells, porcine glial progenitor cells, canine glial progenitor cells, and feline glial progenitor cells. In some embodiments, the adult glial progenitor cells are adult human glial progenitor cells.

In some embodiments, said administering is carried out ex vivo. In other embodiments of the methods according to the present disclosure, said administering is carried out in vivo.

Another aspect of the present application relates to a method of treating a myelin deficiency in a subject by suppressing certain transcription factors. This method involves administering, to the subject having the myelin deficiency, an agent that suppresses one or more transcription factors selected from the group consisting of ZNF274, MAX, E2F6, IKZF3, and STAT3, wherein the agent is administered in an effective amount to suppress the one or more transcription factors in adult glial progenitor cells of the subject.

Another aspect of the present application relates to a method of treating a myelin deficiency in a subject by suppressing certain senescence genes. The method involves administering, to the subject, an agent that inhibits expression of one or more senescence genes selected from the group consisting of RUNX1, BIN1, VAMP3, DMTF1, CTNNA1, SERPINE1, CDK19, CDKNIC, RUNX2, EFEMP1, MAP3K7, AHR, OGT, PAK1, CBX7, and CYLD, wherein the agent is administered in an effective amount to suppress the one or more senescence genes in adult glial progenitor cells of the subject.

Another aspect of the present application relates to a method of treating a myelin deficiency in a subject by suppressing certain glial target genes. The method involves administering, to the subject, an agent that inhibits expression of one or more senescence genes selected from the group consisting of MBP, CD9, ENPP2, PLP1, ERBIN, ZNF365, UGT8, GDNF, DUSP10, PMP22, ERBB4, and MYRF, wherein the agent is administered in an effective amount to suppress the one or more glial target genes in adult glial progenitor cells of the subject.

In accordance with this aspect of the present application, the myelin deficiency may be associated with a condition selected from the group consisting of multiple sclerosis, neuromyelitis optica, transverse myelitis, optic neuritis, subcortical stroke, diabetic leukoencephalopathy, hypertensive leukoencephalopathy, age-related white matter disease, spinal cord injury, radiation- or chemotherapy induced demyelination, post-infectious and post-vaccinial leukoencephalitis, periventricular leukomalacia, pediatric leukodystrophy (e.g., Pelizaeus-Merzbacher Disease, Tay-Sach Disease, Sandhoff's gangliosidoses, Krabbe's disease, metachromatic leukodystrophy, mucopolysaccharidoses, Niemann-Pick A disease, adrenoleukodystrophy, Canavan's disease, Vanishing White Matter Disease, and Alexander Disease), lysosomal storage diseases, congenital dysmyelination, inflammatory demyelination, vascular demyelination, and cerebral palsy.

In some embodiments, the myelin deficiency is associated with a neurodegenerative disease, e.g., Huntington's disease. As used herein, "Huntington's disease" refers to an autosomal dominant inherited brain disorder that typically becomes manifest in adulthood. Huntington's disease pathology is characterized by hypomyelination, as well as neuronal and white matter loss.

In other embodiments, the myelin deficiency is associated with a neuropsychiatric disease, e.g., schizophrenia.

In some embodiments, the agent used in the method of inducing rejuvenation or the method of treating myelin deficiency is an agent that suppresses STAT3. As illustrated in FIG. 4F of the present disclosure, in the context of adult glial progenitor cells, STAT3 is predicted to activate a set of senescence-associated genes (e.g., BIN1, DMTF1, CD47, CTNNA1, RUNX2, RUNX1, MAP3K7, and OGT), glial cell-associated genes (e.g., PLP1, CNP, PMP22, SEMA4D, CLDN11, GPR37, MYRF, MAG, BCAS1, ST18, ERBB4, CERS2, LPAR1, and GJB1), and downstream transcription factors (e.g., MAX, E2F6, and IKZF3). In some embodiments, the agent is an agent that suppresses or silences the activity of STAT3 and/or any of the senescence-associated genes noted above that are activated by STAT3.

In some embodiments, the agent used in the method inducing rejuvenation and the method of treating myelin deficiency is an agent that suppresses one or more of ZNF274, MAX, E2F6, and IKZF3. As illustrated in FIG. 4G of the present application, in the context of adult glial progenitor cells, ZNF274, MAX, E2F6, and IKZF3 are predicted to repress sets of proliferation-associated gene targets (e.g., YAP1, LMNB1, PATZ1, TEAD1, FN1, TP53, CDK1, CCND2, CDKN2D, CENPH, MKI67, CDK4, CENPF, CDK5, CDKN3, and CHEK1), glial cell-associated genes (e.g., CHRDL1, ST8SIA1, PTPRZ1, CA10, PDGFRA, BCAN, NXPH1, CSPG4, and, PCDH15), and downstream transcription factors (e.g., BLC11A, EZH2, HDAC2, NF1B, MYC, HMGA2, and TEAD).

In some embodiments, the agent is an agent that suppresses or silences the activity of ZNF274, MAX, E2F6, IKZF3, or any combination thereof to allow the expression of downstream proliferation-associated gene targets.

In some embodiments, the agent is an agent that suppresses ZNF274, MAX, E2F6, IKZF3, and/or STAT3. Suitable agents for use in the methods described herein include, without limitation, a ZNF274 inhibitor, a MAX inhibitor, an E2F6 inhibitor, an IKZF3 inhibitor, and a STAT3 inhibitor.

The ZNF274 inhibitor, MAX inhibitor, E2F6 inhibitor, IKZF3 inhibitor, and/or STAT3 inhibitor may be (1) a small molecule inhibitor, (2) a nucleic acid molecule inhibitor (e.g., a miRNA, a shRNAi, a siRNA, and an antisense oligonucleotide), (3) a nuclease-based gene editing system (e.g., a CRISPR/Cas-system targeted to silence ZNF274, MAX, E2F6, IKZF3, and/or STAT expression), or (4) a nucleic acid molecule encoding (2) or (3).

Small Molecule Inhibitors

In some embodiments, the ZNF274 inhibitor, MAX inhibitor, E2F6 inhibitor, IKZF3 inhibitor, and/or STAT3 inhibitor is a small molecule inhibitor. Exemplary small molecule inhibitors of these transcription factors that are known in the art and suitable for use in accordance with the methods described herein are provided in Table 5 below. Analogs and derivatives of the small molecule inhibitors of Table 5 are also contemplated for use in the methods described herein.

TABLE 5

Exemplary Small Molecule Inhibitors

| Transcription Factor | Exemplary Small Molecule Inhibitors |
|---|---|
| MYC-associated factor X (MAX) inhibitor | 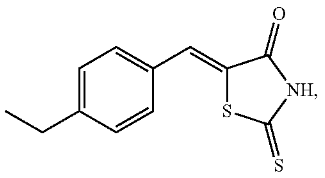 [SMILES: CCc1ccc(/C=C2\SC(=S)NC2=O)cc1] 100-58-F4 (1RH) 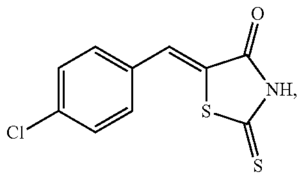 [SMILES: O=C1NC(=S)S/C1=C\c1ccc(Cl)cc1] 12RH |

TABLE 5-continued
| Exemplary Small Molecule Inhibitors | |
|---|---|
| Transcription Factor | Exemplary Small Molecule Inhibitors |
| | 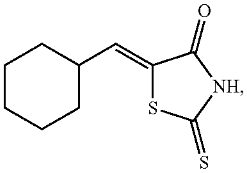 [SMILES: O=C1NC(=S)S/C1=C\C1CCCCC1] 22RH |
| | 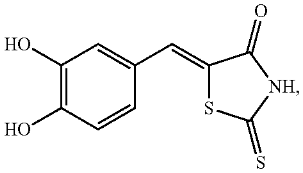 [SMILES: O=C1NC(=S)S/C1=C\c1ccc(O)c(O)c1] 27RH |
| | 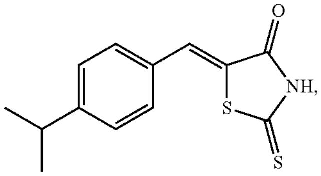 [SMILES: CC(C)c1ccc(/C=C2\SC(=S)NC2=O)cc1] 28RH |
| | 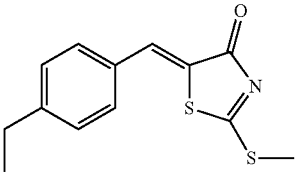 [SMILES: CCc1ccc(/C=C2\SC(SC)=NC2=O)cc1] 1RH-S-Me |
| | 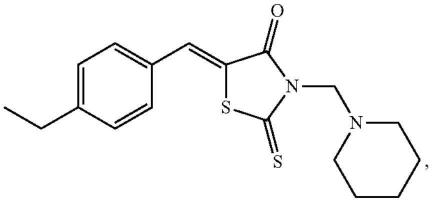 [SMILES: CCc1ccc(/C=C2\SC(=S)N(CN3CCCCC3)C2=O)cc1] 1RH-NCN-1 |
| | 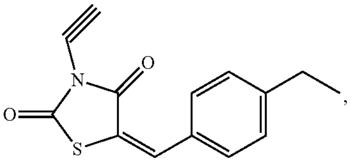 [SMILES: C#CN1C(=O)S/C(=C/c2ccc(CC)cc2)C1=O] #015 |

TABLE 5-continued
| Exemplary Small Molecule Inhibitors | |
|---|---|
| Transcription Factor | Exemplary Small Molecule Inhibitors |
| | 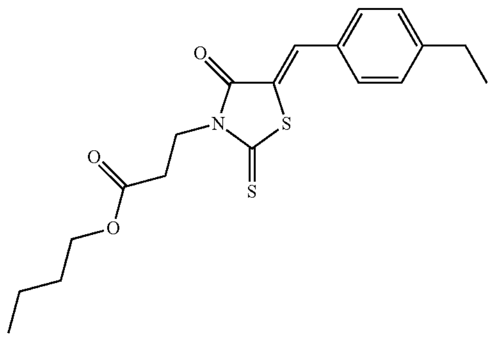 [SMILES: CCCCOC(=O)CCN1C(=O)/C(=C/c2ccc(CC)cc2)SC1=S]<br>#474<br>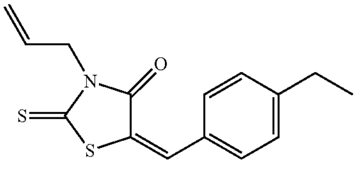 [SMILES: C=CCN1C(=O)/C(=C\c2ccc(CC)cc2)SC1=S]<br>#764<br>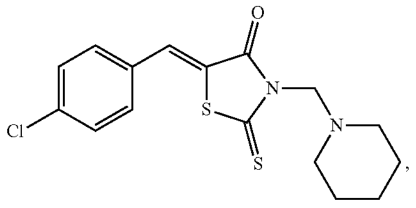 [SMILES: O=C1/C(=C/c2ccc(Cl)cc2)SC(=S)N1CN1CCCCC1]<br>12RH-NCN-1<br>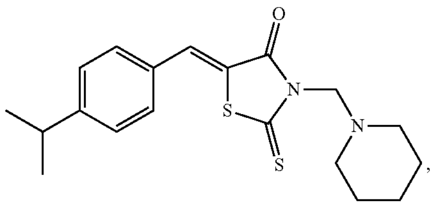 [SMILES: CC(C)c1ccc(/C=C2\SC(=S)N(CN3CCCCC3)C2=O)cc1]<br>28RH-NCN-1<br>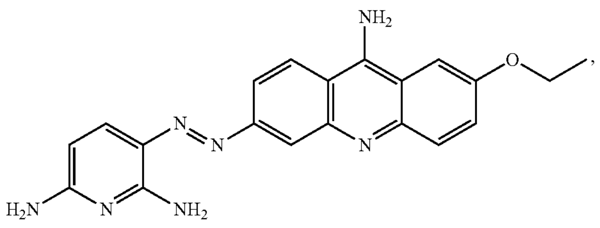 [SMILES: CCOc1ccc2nc3cc(/N=N/c4ccc(N)nc4N)ccc3c(N)c2c1]<br>MYCMI-6 |

TABLE 5-continued
| Exemplary Small Molecule Inhibitors | |
|---|---|
| Transcription Factor | Exemplary Small Molecule Inhibitors |
| | 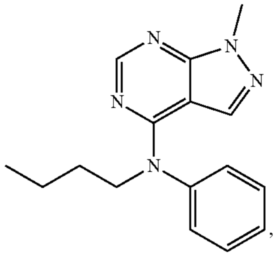 , and MYCMI-11 |
| | 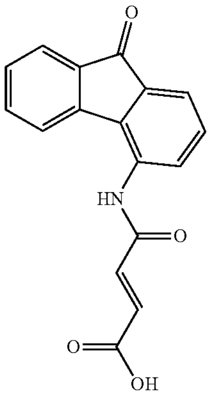 [SMILES: O=C(O)/C=C/C(=O)Nc1cccc2c1-c1ccccc1C2=O] MYCMI-14 |
| Zinc finger protein Aiolos (IKZF3) | 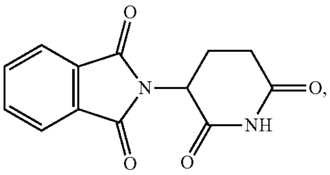 [SMILES: O=C1CCC(N2C(=O)c3ccccc3C2=O)C(=O)N1] , Thalidomide |
| | 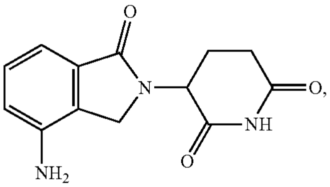 [SMILES: Nc1cccc2c1CN(C1CCC(=O)NC1=O)C2=O] , Lenalidomide |
| | 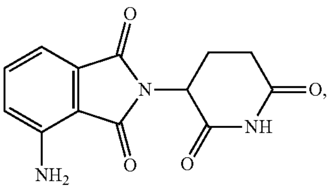 [SMILES: Nc1cccc2c1C(=O)N(C1CCC(=O)NC1=O)C2=O] , Pomalidomide |

TABLE 5-continued
| Exemplary Small Molecule Inhibitors | |
|---|---|
| Transcription Factor | Exemplary Small Molecule Inhibitors |
| | 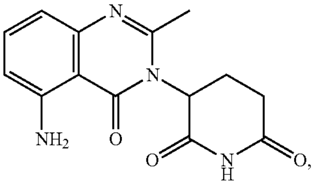 [SMILES: Cc1nc2cccc(N)c2c(=O)n1C1CCC(=O)NC1=O] CC-122 |
| | 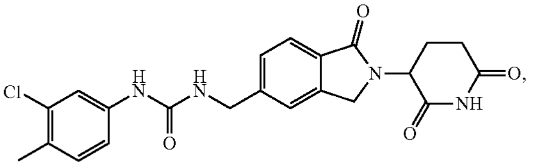 and CC-885 |
| | 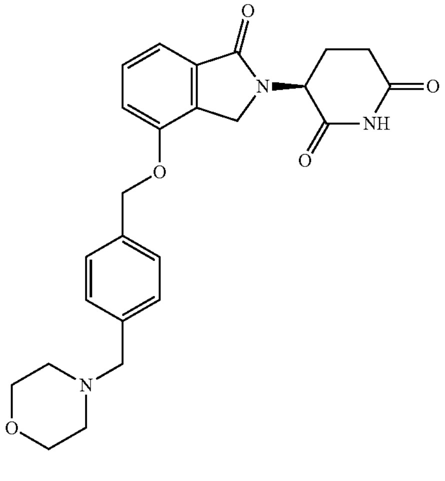 [SMILES: O=C1CC[C@H](N2Cc3c(OCc4ccc(CN5CCOCC5)cc4)cccc3C2=O)C(=O)N1] CC-220 |
| Signal transducer and activator of transcription 3 (STAT3) | 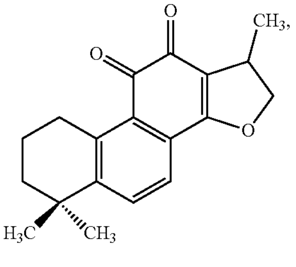 Cryptotanshinone |
| | 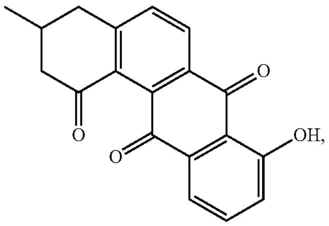 [SMILES: CC1CC(=O)c2c(ccc3c2C(=O)c2cccc(O)c2C3=O)C1] STA-21 |

TABLE 5-continued
| Exemplary Small Molecule Inhibitors | |
| --- | --- |
| Transcription Factor | Exemplary Small Molecule Inhibitors |
| | 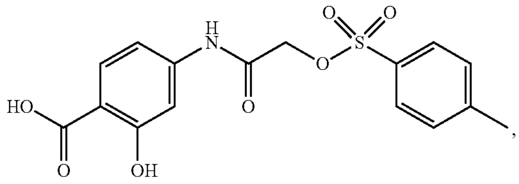 [SMILES: Cc1ccc(S(=O)(=O)OCC(=O)Nc2ccc(C(=O)O)c(O)c2)cc1], NSC 74859 (S31-201) |
| | 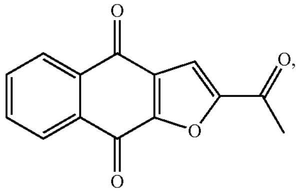 [SMILES: CC(=O)c1cc2c(o1)C(=O)c1ccccc1C2=O] Napabucasin |
| | 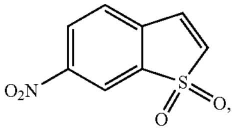 [SMILES: O=[N+]([O-])c1ccc2c(c1)S(=O)(=O)C=C2] Stattic, 1 |
| | 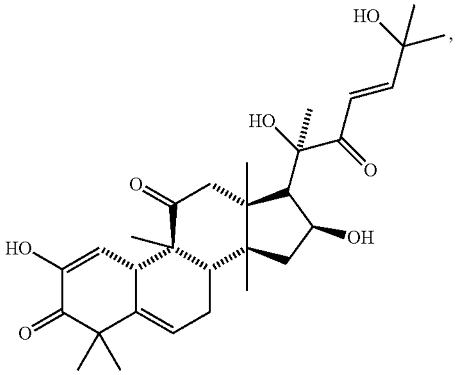, Cucurbitacin I JSI-124 |
| | 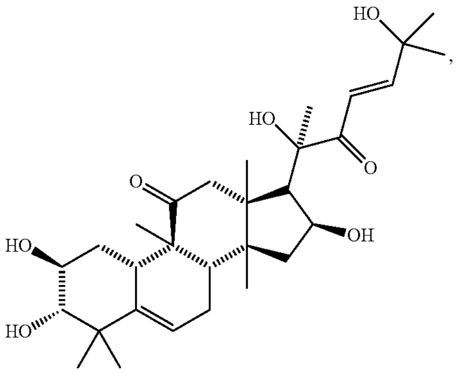, Cucurbitacin Q |

TABLE 5-continued
| Exemplary Small Molecule Inhibitors | |
|---|---|
| Transcription Factor | Exemplary Small Molecule Inhibitors |
| | 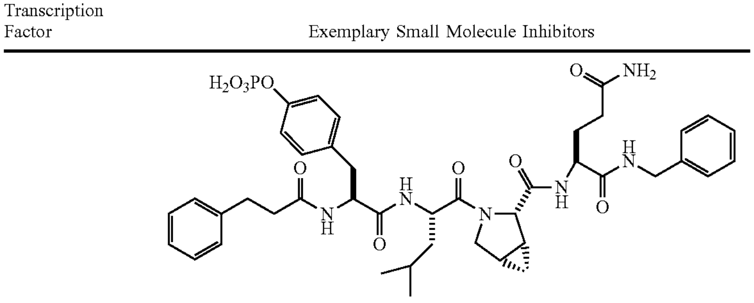<br>Phpr-pTyr-Leu-cis-3,4-methanoPro-Gln-NHBn<br>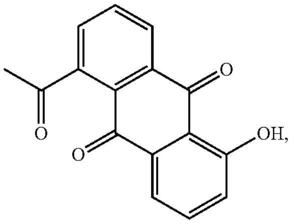 [SMILES: CC(=O)c1cccc2c1C(=O)c1cccc(O)c1C2=O]<br>LLL-3<br>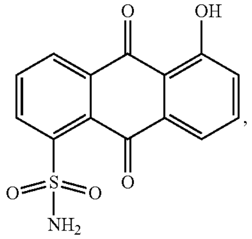 [SMILES: NS(=O)(=O)c1cccc2c1C(=O)c1cccc(O)c1C2=O]<br>LLL-12<br>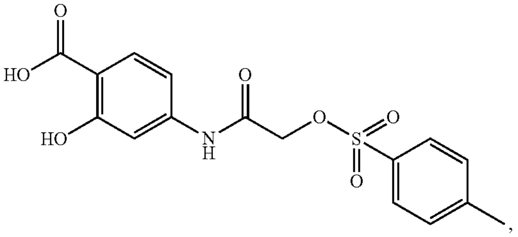 [SMILES: Cc1ccc(S(=O)(=O)OCC(=O)Nc2ccc(C(=O)O)c(O)c2)cc1]<br>S31-201<br>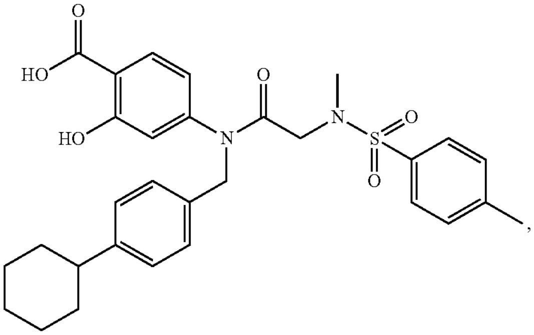 [SMILES: Cc1ccc(S(=O)(=O)N(C)CC(=O)N(Cc2ccc(C3CCCCC3)cc2)c2ccc(C(=O)O)c(O)c2)cc1]<br>SF-1-066 |

TABLE 5-continued
| Exemplary Small Molecule Inhibitors | |
|---|---|
| Transcription Factor | Exemplary Small Molecule Inhibitors |
| | 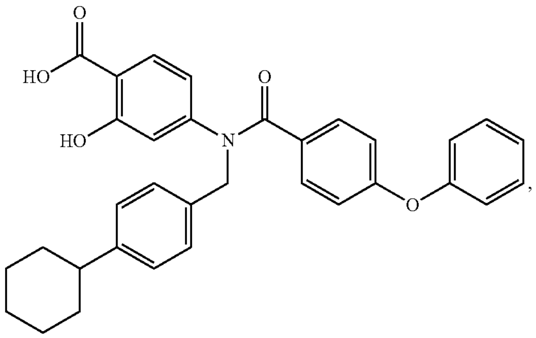 [SMILES: O=C(O)c1ccc(N(Cc2ccc(C3CCCCC3)cc2)C(=O)c2ccc(Oc3ccccc3)cc2)cc1O] S31-1757 |
| | 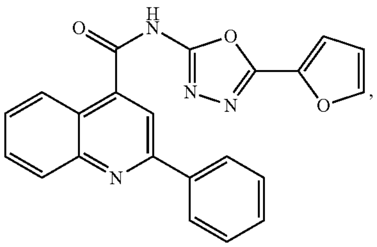 [SMILES: O=C(Nc1nnc(-c2ccco2)o1)c1cc(-c2ccccc2)nc2ccccc12] STX-0119 |
| | 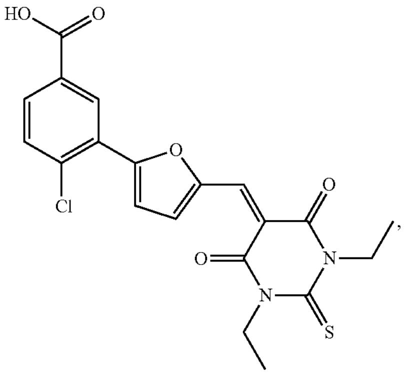 [SMILES: CCN1C(=O)C(=Cc2ccc(-c3cc(C(=O)O)ccc3Cl)o2)C(=O)N(CC)C1=S] Cpd30-12 |
| | 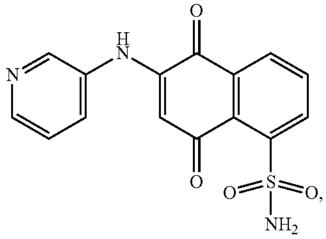 [SMILES: NS(=O)(=O)c1cccc2c1C(=O)C=C(Nc1cccnc1)C2=O] LY5 |

TABLE 5-continued

| Exemplary Small Molecule Inhibitors | |
|---|---|
| Transcription Factor | Exemplary Small Molecule Inhibitors |
| | 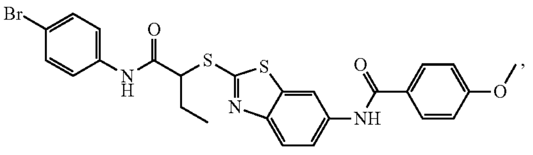, and Cpd9 |
| | 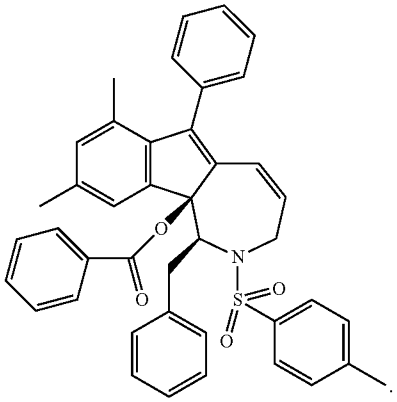 [SMILES: Cc1ccc(S(=O)(=O)N2CC=CC3=C(c4ccccc4)c4c(C)cc(C)cc4[C@@]3(OC(=O)c3ccccc3)[C@@H]2Cc2ccccc2)cc1]. Cpd1 |

In some embodiments, the small molecule inhibitor is a small molecule inhibitor of Myc-associated factor X (MAX) selected from the group consisting of 10058-F4 (also known as "10058-F4 (1RH)") (see, e.g., Huang et al., "A Small-Molecule c-Myc Inhibitor, 10058-F4, Induces Cell-Cycle Arrest, Apoptosis, and Myeloid Differentiation of Human Acute Myeloid Leukemia," Exp. Hematol. 34(11):1480-1489 (2006), which is hereby incorporated by reference in its entirety); MYCMI-6, MYCMI-11, and MYCMI-14 (see, e.g., Castell et al., "A Selective High Affinity MYC-Binding Compound Inhibits MYC: MAX Interaction and MYC-Dependent Tumor Cell Proliferation," Sci. Rep. 8:10064 (2018), which is hereby incorporated by reference in its entirety); 12RH, 22RH, 27RH, 28RH, 1RH-S-Me, 1RH-NCN-1, #015, #474, #764, 12RH-NCN-1, and 28RH-NCN-1 (see, e.g., Wang et al., "Improved Low Molecular Weight Myc-Max inhibitors," Mol. Cancer Ther. 6(9):2399-2408 (2007), which is hereby incorporated by reference in its entirety).

In some embodiments, the small molecule inhibitor is a small molecule inhibitor of signal transducer and activator of transcription 3 (STAT3) selected from the group consisting of cryptotanshinone (see, e.g., Shin et al., "Cryptotanshinone Inhibits Constitutive Signal Transducer and Activator of Transcription 3 Function through Blocking the Dimerization in DU145 Prostate Cancer Cells," Cancer Res. 69(1): 193-202 (2009), which is hereby incorporated by reference in its entirety); STA-21 (see, e.g., Song et al., "A Low-Molecular-Weight Compound Discovered through Virtual Database Screening Inhibits Stat3 Function in Breast Cancer Cells," PNAS 102(13):4700-4705 (2005), which is hereby incorporated by reference in its entirety); NSC 7459 (S31-201) (see, e.g., Siddiquee et al., "Selective Chemical Probe Inhibitor of Stat3, Identified through Structure-Based Virtual Screening, Induces Antitumor Activity," PNAS 104 (18):7391-7396 (2007), which is hereby incorporated by reference in its entirety); napabucasin (BBI608) (see, e.g., Li et al., "Suppression of Cancer Relapse and Metastasis by Inhibiting Cancer Stemness," PNAS 112(6):1839-1844 (2015) and Hubbard et al., "Napabucasin: An Update on the First-in-Class Cancer Stemness Inhibitor," Drugs 77(10): 1091-1103 (2017), which are hereby incorporated by reference in their entirety); Stattic, cucurbitacin I, cucurbitacin Q, Phpr-pTyr-Leu-cis-3,4-methanoPro-Gln-NHBn (see, e.g., McMurray, J., "A New Small-Molecule Stat3 Inhibitor," Chem. Biol. 13(11):1123-1124 (2006), which is hereby incorporated by reference in its entirety); LLL-3 (see, e.g., Fuh et al., "LLL-3 Inhibits STAT3 Activity, Suppresses Glioblastoma Cell Growth and Prolongs Survival in a Mouse Glioblastoma Model," Br. J. Cancer 100(1):106-112 (2009), which is hereby incorporated by reference in its entirety); LLL-12, S31-201, SF-1-066, S31-1757, STX-0119, Cpd30-12, LY5, Cpd9, and Cpd1 (see, e.g., Orlova et al., "Direct Targeting Options for STAT3 and STAT5 in Cancer," Cancers 11(12):1930 (2019), which is hereby incorporate by reference in its entirety); SF-1-087, SF-1-121, S3I-M2001, S3I-201.1066, and BP-1-102 (see, e.g., Wu et al., "Negative Regulators of STAT Signaling Pathway in Cancers," Cancer Manag. Res. 11:4957-4969 (2019), which is hereby incorporated by reference in its entirety); HO-3867 (see, e.g., Tierney et al., "HO-3867, a STAT3 Inhibitor Induces Apoptosis by Inactivation of STAT3 Activity in BRCA1-Mutated Ovarian Cancer Cells," Cancer Biol. Ther. 13(9):766-775 (2012); corylifol A (see, e.g., Lee et al., "Phenolic Compounds Isolated from Psoralea corylifolia Inhibit IL-6-Induced STAT3 Activation," Planta. Med. 78(9):903-906 (2012), which is hereby incorporated by reference in its entirety); and SD 1008 (see, e.g., Liu et al., "SOCS3 Promotes Inflammation and Apoptosis via Inhibiting JAK2/STAT3 Signaling Pathway in 3T3-L1 Adipocyte," Immunobiology 220(8):947-953 (2015), which is hereby incorporated by reference in its entirety).

Nucleic Acid Inhibitors

In some embodiments, the ZNF274 inhibitor, MAX inhibitor, E2F6 inhibitor, IKZF3 inhibitor, and/or STAT3 inhibitor is a nucleic acid molecule inhibitor.

As used herein, the term "nucleic acid molecule inhibitor" refers to a nucleic acid molecule that reduces or eliminates the expression of a target gene. The nucleic acid molecule inhibitor typically contains a region that specifically targets a sequence in the target gene or target gene mRNA to achieve target-specific inhibition. Typically, the targeting region of the nucleic acid inhibitor molecule comprises a sequence that is sufficiently complementary to a sequence on the target gene or target gene mRNA to direct the effect of the nucleic acid inhibitor molecule to the specified target gene or target gene mRNA. For example, a "nucleic acid molecule inhibitor of ZNF274" reduces or eliminates the expression of a ZNF274 gene. The nucleic acid inhibitor molecule may include natural ribonucleotides, natural deoxyribo-nucleotides, and/or modified nucleotides. The modified nucleotides include modifications such as substitution on positions on the sugar ring, modifications of the phosphoester linkages between nucleotides, non-natural bases, and non-natural alternative carbon structures such as locked nucleic acids ("LNA") and unlocked nucleic acids ("UNA").

As used herein, the term "reduce" or "reduces" refers to its meaning as is generally accepted in the art. With reference to exemplary nucleic acid inhibitor molecules (e.g., nucleic acid molecule inhibitors of ZNF274, MAX, E2F6, IKZF3, and/or STAT3 selected from a miRNA, a shRNAi, a siRNA, and an antisense oligonucleotide), reduce" or "reduces" generally refers to a suppression in the transcription and/or translation of a gene or in the levels of the gene product relative to the transcription and/or translation of the gene observed in the absence of the nucleic acid inhibitor molecule. In some embodiments, the reduction in the transcription and/or translation of a gene or in the levels of the gene product is at least 10%, at least 20%, at least 30%, at least 40%, at least 50%, at least 60%, at least 70%, at least 80%, at least 90%, at least 95%, at least 96%, at least 97%, at least 98%, at least 99%, up to 100% (i.e., no detectable transcription and/or translation) or a reduction of at least 2-fold, at least 5-fold, at least 10-fold, at least 20-fold, at least 30-fold, at least 40-fold, at least 50-fold, or more relative to that observed in the absence of the nucleic acid inhibitor molecule according to the present disclosure.

Suitable nucleic acid inhibitor molecules include, without limitation, (i) a nucleic acid molecule inhibitor of ZNF274 selected from a miRNA, a shRNAi, a siRNA, and an antisense oligonucleotide (ASO); (ii) a nucleic acid molecule inhibitor of MAX selected from a miRNA, a shRNAi, a siRNA, and an antisense oligonucleotide; (iii) a nucleic acid molecule inhibitor of E2F6 selected from a miRNA, a shRNAi, a siRNA, and an antisense oligonucleotide; (iv) a nucleic acid molecule inhibitor of IKZF3 selected from a miRNA, a shRNAi, a siRNA, and an antisense oligonucleotide; and (v) a nucleic acid molecule inhibitor of STAT3 selected from a miRNA, a miRNA inhibitor, a shRNAi, a siRNA, and an antisense oligonucleotide.

As use herein, the term "microRNA" or "miRNA" refers to a class of small RNA molecules that may negatively regulate gene expression (see, e.g., Lam et al., "siRNA Versus miRNA as Therapeutics for Gene Silencing," Mol. Ther. Nucleic Acids 4(9):e252 (2015), which is hereby incorporated by reference in its entirety). miRNA gene transcription is carried out by RNA polymerase II in the nucleus to give primary miRNA (pri-miRNA), which is a 5' capped, 3' polyadenylated RNA with double-stranded stem-loop structure. The pri-miRNA is then cleaved by a microprocessor complex (comprising Drosha and microprocessor complex subunit DCGR8) to form precursor miRNA (pre-miRNA), which is a duplex that contains 70-100 nucleotides with interspersed mismatches and adopts a loop structure. The pre-miRNA is subsequently transported by Exportin 5 from the nucleus to the cytoplasm, where it is further processed by Dicer into a miRNA duplex of 18-25 nucleotides. The miRNA duplex then associates with the RISC forming a complex called miRISC. The miRNA duplex is unwound, releasing and discarding the passenger strand (sense strand). The mature single-stranded miRNA guides the miRISC to the target mRNAs. Mature miRNA may bind to a target mRNA through partial complementary base pairing with the consequence that the target gene silencing occurs via translational repression, degradation, and/or cleavage. In some embodiments, the nucleic acid inhibitor molecule is a miRNA molecule. Suitable miRNA inhibitor molecules for use in the methods of the present disclosure include, without limitation, those identified in Table 6 below.

TABLE 6

Exemplary miRNA sequences

| Transcription Factor | miRNA | Sequence | SEQ ID NO: |
|---|---|---|---|
| MAX | miR-485-5p | AGAGGCUGGCCGUGAUGAAUUC | 7 |
| E2F6 | miR-379-5p | UGGUAGACUAUGGAACGUAGG | 8 |
| STAT3 | miR-125b-5p | UCCCUGAGACCCUAACUUGUGA | 9 |
| STAT3 | miR-106a-5p | AAAAGUGCUUACAGUGCAGGUAG | 10 |
| STAT3 | miR-17-5p | CAAAGUGCUUACAGUGCAGGUAG | 11 |
| STAT3 | miR-130a-3p | CAGUGCAAUGUUAAAAGGGCAU | 12 |
| STAT3 | miR-130b-3p | CAGUGCAAUGAUGAAAGGGCAU | 13 |

In some embodiments, the MAX inhibitor is a nucleic acid molecule inhibitor of MAX, and a suitable MAX nucleic acid molecule inhibitor is a miRNA. In accordance with such embodiment, exemplary MAX inhibitor miRNAs have a nucleotide sequence corresponding to miR-485-5p, pre-miR-485-5p, or mature miR-485-5p. For example, the miRNA may have the nucleotide sequence of SEQ ID NO:7.

In some embodiments, the E2F6 inhibitor is a nucleic acid molecule inhibitor of E2F6, and a suitable E2F6 nucleic acid molecule inhibitor is a miRNA. In accordance with such embodiment, exemplary E2F6 inhibitor miRNAs have a nucleotide sequence corresponding to miR-379-5p, pre-miR-379-5p, or mature miR-379-5p. For example, the miRNA may have the nucleotide sequence of SEQ ID NO:8.

In some embodiments, the STAT3 inhibitor is a nucleic acid molecule inhibitor of STAT3, and a suitable STAT3 inhibitor is a miRNA. In accordance with such embodiment, exemplary STAT3 inhibitory miRNAs have a nucleotide sequence corresponding to miR-125b-5p, pre-miR-125b-5p, mature miR-125b-5p, miR-106a-5p, pre-miR-106a-5p, mature miR-106a-5p, miR-17-5p, pre-miR-17-5p, mature miR-17-5p, miR-130a-3p, pre-miR-130a-3p, mature miR- 130a-3p, miR-130b-3p, pre-miR-130b-3p, or mature miR-130b-3p. For example, the miRNA may have the nucleotide sequence of SEQ ID NO:9, SEQ ID NO: 10, SEQ ID NO: 11, SEQ ID NO:12, or SEQ ID NO: 13.

In some embodiments, the agent used in the method of inducing rejuvenation and the method of treating myelin deficiency comprises one or more expression vectors encoding (i) one or more microRNA selected from the group consisting of miR-125b-5p, miR-106a-5p, miR-17-5p, miR-130a-3p, and miR-130b-3p, wherein said administering suppresses the signal transducer and activator of transcription 3 (STAT3) signaling pathway; (ii) miR-379-5p, wherein said administering suppresses the E2F transcription factor 6 (E2F6) signaling pathway; and/or (iii) miR-485-5p, wherein said administering suppresses the Myc-associated factor X (MAX) signaling pathway.

In some embodiments, the agent used in the method of inducing rejuvenation and the method of treating myelin deficiency comprises an expression vectors encoding an MAX inhibitor. In some embodiments, the MAX inhibitor is a nucleic acid molecule inhibitor. In some embodiments, the MAX nucleic acid molecule inhibitor is a miRNA. In accordance with such an embodiment, exemplary MAX inhibitor miRNAs have a nucleotide sequence corresponding to miR-485-5p, pre-miR-485-5p, or mature miR-485-5p. For example, the miRNA may have the nucleotide sequence of SEQ ID NO:7.

In some embodiments, the agent used in the method of inducing rejuvenation and the method of treating myelin deficiency comprises an expression vector encoding an E2F6 inhibitor. In some embodiments, the E2F6 inhibitor is a nucleic acid molecule inhibitor. In some embodiments, the E2F6 nucleic acid molecule inhibitor is a miRNA. In accordance with such embodiment, exemplary E2F6 inhibitor miRNAs have a nucleotide sequence corresponding to miR-379-5p, pre-miR-379-5p, or mature miR-379-5p. For example, the miRNA may have the nucleotide sequence of SEQ ID NO:8.

In some embodiments, the agent used in the method of inducing rejuvenation and the method of treating myelin deficiency comprises an expression vector encoding an STAT3 inhibitor. In some embodiments, the STAT3 inhibitor is a nucleic acid molecule inhibitor. In some embodiments, the STAT3 nucleic acid molecule inhibitor is a miRNA. In accordance with such embodiment, exemplary STAT3 inhibitory miRNAs have a nucleotide sequence corresponding to miR-125b-5p, pre-miR-125b-5p, mature miR-125b-5p, miR-106a-5p, pre-miR-106a-5p, mature miR-106a-5p, miR-17-5p, pre-miR-17-5p, mature miR-17-5p, miR-130a-3p, pre-miR-130a-3p, mature miR-130a-3p, miR-130b-3p, pre-miR-130b-3p, or mature miR-130b-3p. For example, the miRNA may have the nucleotide sequence of SEQ ID NO:9, SEQ ID NO: 10, SEQ ID NO:11, SEQ ID NO:12, or SEQ ID NO: 13.

In some embodiments, the agent used in the method of inducing rejuvenation and the method of treating myelin deficiency comprises an expression vector that encodes (1) one or more microRNA selected from the group consisting of miR-485-5p miR-379-5p, miR-125b-5p, miR-106a-5p, miR-17-5p, miR-130a-3p and miR-130b-3p, and (2) one or more microRNA selected from the group consisting of miR-93-3p, miR-1260b, miR-767-5p, miR-30b-5p, miR-9-3p, and miR-9-5p, as shown in Table 7 below.

TABLE 7 miRNA Sequences

| miRNA | Sequence | SEQ ID NO: |
|---|---|---|
| miR-93-3p | ACUGCUGAGCUAGCACUUCCCG | 8 |
| miR-1260b | AUCCCACCACUGCCACCAU | 9 |
| miR-767-5p | UGCACCAUGGUUGUCUGAGCAUG | 10 |
| miR-30b-5p | UGUAAACAUCCUACACUCAGCU | 11 |
| miR-9-3p | AUAAAGCUAGAUAACCGAAAGU | 12 |
| miR-9-5p | UCUUUGGUUAUCUAGCUGUAUGA | 13 |

In some embodiments, the nucleic acid inhibitor molecule of ZNF274, MAX, E2F6, IKZF3, and/or STAT3 is an shRNA molecule. Short hairpin RNA (shRNA) molecules comprise the sense and antisense sequences from a target gene connected by a loop. Once transcribed, shRNA molecules are transported from the nucleus into the cytoplasm where the enzyme Dicer processes them into small/short interfering RNAs (siRNAs) in a short hairpin RNA interference process. As used herein, the term "short hairpin RNA interference" or "shRNAi" is a process mediated by a class of small RNA molecules that negatively regulate gene expression.

In some embodiments, the ZNF274 inhibitor is a nucleic acid molecule inhibitor of ZNF274, and a suitable ZNF274 inhibitor is a ZNF274 shRNA. In some embodiments, the MAX inhibitor is a nucleic acid molecule inhibitor of MAX, and a suitable MAX inhibitor is a MAX shRNA. In some embodiments, the E2F6 inhibitor is a nucleic acid molecule inhibitor of E2F6, and a suitable E2F6 inhibitor is an E2F6 shRNA. In some embodiments, the IKZF3 inhibitor is a nucleic acid molecule inhibitor of IKZF3, and a suitable IKZF3 inhibitor is an IKZF3 shRNA. In some embodiments, the STAT3 inhibitor is a nucleic acid molecule inhibitor of STAT3, and a suitable STAT3 inhibitor is a STAT3 shRNA.

In some embodiments, the nucleic acid inhibitor molecule of ZNF274, MAX, E2F6, IKZF3, and/or STAT3 is a siRNA. As used herein, the term "short interfering RNA" or "siRNA" refers to short nucleic acid molecules typically 21-23 nucleotides in length with 3'-two nucleotide overhangs (see, e.g., McManus & Sharp, "Gene Silencing in Mammals by Small Interfering RNAs," Nat. Rev. Genet. 3(10):737-747 (2002), which is hereby incorporated by reference in its entirety). siRNA interacts with and activates the RNA-induced silencing complex ("RISC"). The endonuclease argonaute 2 (AGO2) component of the RISC cleaves the passenger strand (sense strand) of the siRNA while the guide strand (antisense strand) remains associated with the RISC.

Subsequently, the guide strand guides the active RISC to its target mRNA for cleavage by AGO2. As the guide strand only binds to mRNA that is fully complementary to it, siRNA causes specific gene silencing (see, e.g., Lam et al., "siRNA Versus miRNA as Therapeutics for Gene Silencing," Mol. Ther. Nucleic Acids 4 (9): e252 (2015), which is hereby incorporated by reference in its entirety).

In some embodiments, the ZNF274 inhibitor is a ZNF274 siRNA. In some embodiments, the MAX inhibitor is a MAX siRNA. In some embodiments, the E2F6 inhibitor is an E2F6 siRNA. In some embodiments, the IKZF3 inhibitor is an IKZF3 siRNA. In some embodiments, the STAT3 inhibitor is a STAT3 siRNA.

In some embodiments, the nucleic acid inhibitor molecule of ZNF274, MAX, E2F6, IKZF3, and/or STAT3 is an antisense oligonucleotide. As used herein, the term "antisense oligonucleotide" or "ASO" refers to small (~18-30 nucleotides), synthetic, single-stranded nucleic acid polymers of diverse chemistries, which can be employed to modulate gene expression via various mechanisms (see, e.g., Roberts et al., "Advances in Oligonucleotide Drug Delivery," Nature Reviews Drug Discovery 19:673-694 (2020), which is hereby incorporated by reference in its entirety). ASOs can be subdivided into two major categories: RNase H competent and steric block. The endogenous RNase H enzyme RNASEH1 recognizes RNA-DNA heteroduplex substrates that are formed when DNA-based oligonucleotides bind to their cognate mRNA transcripts and catalyzes the degradation of RNA. Cleavage at the site of ASO binding results in destruction of the target RNA, thereby silencing target gene expression. Steric block oligonucleotides are ASOs that are designed to bind to target transcripts with high affinity but do not induce target transcript degradation as they lack RNase H competence. Such oligonucleotides therefore comprise either nucleotides that do not form RNase H substrates when paired with RNA or a mixture of nucleotide chemistries (that is, 'mixmers') such that runs of consecutive DNA-like bases are avoided.

In some embodiments, the ZNF274 inhibitor is a ZNF274 ASO. In some embodiments, the MAX inhibitor is a MAX ASO. In some embodiments, the E2F6 inhibitor is an E2F6 ASO. In some embodiments, the IKZF3 inhibitor is an IKZF3 ASO. In some embodiments, the STAT3 inhibitor is a STAT3 ASO, e.g., danvatirsen (see, e.g., Xu et al., "Population Pharmacokinetic Analysis of Danvatirsen Supporting Flat Dosing Switch," J. Pharmacokinet. Pharmacodyn. 46(1):65-74 (2019), which is hereby incorporated by reference in its entirety).

Methods of designing nucleic acid inhibitors are well known in the art and suitable for designing nucleic acid inhibitors for use in the methods described herein (see, e.g., Lam et al., "siRNA Versus miRNA as Therapeutics for Gene Silencing," Mol. Ther. Nucleic Acids 4(9):e252 (2015) and Kulkarni et al., "The Current Landscape of Nucleic Acid Therapeutics," Nature Nanotechnology 16:630-643 (2021), which are hereby incorporated by reference in their entirety).

Nucleic acid inhibitor molecules are designed to target ZNF274, MAX, E2F6, IKZF3, and/or STAT3 and transcription variants thereof in a sequence specific manner. The sequences of ZNF274, MAX, E2F6, IKZF3, and/or STAT3 and transcription variants thereof are well known in the art and accessible via various curated databases, e.g., NCBI nucleotide or gene database. In some embodiments, the nucleic acid inhibitor molecule is designed to target one or more of the transcription factors identified in Table 8 below using the sequences available via the NCBI Accession number provided.

TABLE 8

Exemplary Human Transcription Factor Genes and Transcript Variants

| Transcription Factor | Gene ID No.* | Transcript Variant | Reference Transcript Accession Nos.* |
|---|---|---|---|
| zinc finger protein 274 (ZNF274) | 10782 | ZNF274c | NM_133502.3 |
| | | ZNF274b | NM_016324.4 |
| | | ZNF274a | NM_016325.4 |
| | | ZNF274d | NM_001278734.2 |

TABLE 8-continued

Exemplary Human Transcription Factor Genes and Transcript Variants

| Transcription Factor | Gene ID No.* | Transcript Variant | Reference Transcript Accession Nos.* |
|---|---|---|---|
| | | transcript variant X1 | XM_011526327.1 |
| | | transcript variant X3 | XM_011526328.2 |
| | | transcript variant X2 | XM_017026174.1 |
| | | transcript variant X5 | XM_017026175.1 |
| | | transcript variant X4 | XR_001753588.2 |
| | | transcript variant X6 | XR_001753589.2 |
| Myc-associated factor X (MAX) | 4149 | transcript variant 1 | NM_002382.5 |
| | | transcript variant 2 | NM_145112.3 |
| | | transcript variant 3 | NM_145113.3 |
| | | transcript variant 4 | NM_145114.3 |
| | | transcript variant 6 | NM_197957.4 |
| | | transcript variant 7 | NM_001271068.2 |
| | | transcript variant 8 | NM_001271069.2 |
| | | transcript variant 11 | NM_001320415.2 |
| | | transcript variant 9 | NR_073137.1 |
| | | transcript variant 10 | NR_073138.1 |
| | | transcript variant X1 | XM_011536773.3 |
| | | transcript variant X7 | XM_017021312.2 |
| | | transcript variant X8 | XM_017021313.1 |
| | | transcript variant X3 | XR_943450.3 |
| | | transcript variant X4 | XR_943451.3 |
| | | transcript variant X5 | XR_943452.3 |
| | | transcript variant X6 | XR_001750326.2 |
| | | transcript variant X9 | XR_001750327.2 |
| | | transcript variant X2 | XR_002957553.1 |
| E2F transcription factor 6 (E2F6) | 1876 | transcript variant a | NM_198256.4 |
| | | transcript variant f | NM_212540.3 |
| | | transcript variant b | NM_001278275.2 |
| | | transcript variant c | NM_001278276.2 |
| | | transcript variant d | NM_001278277.2 |
| | | transcript variant e | NM_001278278.2 |
| | | transcript variant g | NR_103490.2 |
| | | transcript variant X1 | XM_017003547.1 |
| | | transcript variant X2 | XM_017003548.1 |
| | | transcript variant X3 | XM_017003549.2 |
| | | transcript variant X4 | XR_001738660.1 |
| zinc finger protein Aiolos (IKZF3) | 22806 | transcript variant 1 | NM_012481.5 |
| | | transcript variant 2 | NM_183228.3 |
| | | transcript variant 3 | NM_183229.3 |
| | | transcript variant 4 | NM_183230.3 |
| | | transcript variant 5 | NM_183231.3 |
| | | transcript variant 6 | NM_183232.3 |
| | | transcript variant 7 | NM_001257408.2 |
| | | transcript variant 8 | NM_001257409.2 |
| | | transcript variant 9 | NM_001257410.2 |
| | | transcript variant 10 | NM_001257411.2 |
| | | transcript variant 11 | NM_001257412.2 |
| | | transcript variant 12 | NM_001257413.2 |
| | | transcript variant 13 | NM_001257414.2 |
| | | transcript variant 14 | NM_001284514.2 |
| | | transcript variant 15 | NM_001284515.2 |
| | | transcript variant 16 | NM_001284516.1 |
| signal transducer and activator of transcription 3 (STAT3) | 6774 | transcript variant 1 | NM_139276.3 |
| | | transcript variant 2 | NM_003150.4 |
| | | transcript variant 3 | NM_213662.2 |
| | | transcript variant 4 | NM_001369512.1 |
| | | transcript variant 5 | NM_001369513.1 |
| | | transcript variant 6 | NM_001369514.1 |
| | | transcript variant 7 | NM_001369516.1 |
| | | transcript variant 8 | NM_001369517.1 |
| | | transcript variant 9 | NM_001369518.1 |
| | | transcript variant 10 | NM_001369519.1 |
| | | transcript variant 11 | NM_001369520.1 |
| | | transcript variant 12 | NM_001384984.1 |
| | | transcript variant 13 | NM_001384985.1 |
| | | transcript variant 14 | NM_001384986.1 |
| | | transcript variant 15 | NM_001384987.1 |
| | | transcript variant 16 | NM_001384988.1 |
| | | transcript variant 17 | NM_001384989.1 |
| | | transcript variant 18 | NM_001384990.1 |
| | | transcript variant 19 | NM_001384991.1 |
| | | transcript variant 20 | NM_001384992.1 |
| | | transcript variant 21 | NM_001384993.1 |

TABLE 8-continued

| Exemplary Human Transcription Factor Genes and Transcript Variants | | | |
|---|---|---|---|
| Transcription Factor | Gene ID No.* | Transcript Variant | Reference Transcript Accession Nos.* |
| | | transcript variant 22 | XM_017024973.2 |
| | | transcript variant 22 | XM_024450896.1 |

*Each of which is hereby incorporated by reference in its entirety.

In some embodiments, the ZNF274 inhibitor, MAX inhibitor, E2F6 inhibitor, IKZF3 inhibitor, and/or STAT3 inhibitor is a nuclease-based gene editing system capable of silencing expression of ZNF274, MAX, E2F6, IKZF3, and/or STAT3. As used herein, the term "nuclease-based gene editing system" refers to a system comprising a nuclease or a derivative thereof that can be recruited to a target sequence in the genome. The system may comprise a Clustered Regularly Interspaced Short Palindromic Repeat-associated ("Cas") protein (e.g., Cas9, Cas12a, and Cas12b), a zinc finger nuclease ("ZFNs"), or a transcription activator-like effector nucleases ("TALEN").

In some embodiments, the nuclease-based gene editing system is a CRISPR/Cas system targeted to silence ZNF274 expression, MAX expression, E2F6 expression, IKZF3 expression, and/or STAT3 expression. The CRISPR/Cas system may comprise a Cas protein or a nucleic acid molecule encoding the Cas protein and a guide RNA comprising a nucleotide sequence that is complementary to a portion of a target DNA sequence.

As described herein, Cas proteins form a ribonucleoprotein complex with a guide RNA, which guides the Cas protein to a target DNA sequence. Suitable Cas proteins include Cas nucleases (i.e., Cas proteins capable of introducing a double strand break at a target nucleic acid sequence), Cas nickases (i.e., Cas protein derivatives capable of introducing a single strand break at a target nucleic acid sequence), and nuclease dead Cas (dCas) proteins (i.e., Cas protein derivatives that do not have any nuclease activity).

In some embodiments, the Cas protein is a Cas9 protein. As used herein, the term "Cas9 protein" or "Cas9" includes any of the recombinant or naturally-occurring forms of the CRISPR-associated protein 9 (Cas9) or variants or homologs thereof. In some embodiments, the variants or homologs have at least 90%, 95%, 96%, 97%, 98%, 99% or 100% amino acid sequence identity across the whole sequence or a portion of the sequence (e.g., a 50, 100, 150, or 200 continuous amino acid portion) compared to a naturally occurring Cas9 protein. In some embodiments, the Cas9 protein is substantially identical to the protein identified by the UniProt reference number Q99ZW2, G3ECR1, J7RUA5, A0Q5Y3, or J3F2B0 (which are hereby incorporated by reference in their entirety) or a variant or homolog having substantial identity thereto. In some embodiments, the Cas9 protein is selected from the group consisting of a Cas9 nuclease, a Cas9 nickases, and a nuclease dead Cas 9 ("dCas9").

In some embodiments, the Cas protein is a Cas12a protein. As used herein, the term "Cas12a protein" or "Cas12a" includes any of the recombinant or naturally-occurring forms of the CRISPR-associated protein 12 (Cas12a) or variants or homologs thereof. In some embodiments, the variants or homologs have at least 90%, 95%, 96%, 97%, 98%, 99% or 100% amino acid sequence identity across the whole sequence or a portion of the sequence (e.g., a 50, 100, 150, or 200 continuous amino acid portion) compared to a naturally occurring Cas12a protein. In some embodiments, the Cas12a protein is substantially identical to the protein identified by the UniProt reference number A0Q7Q2, U2UMQ6, AOA7C6JPC1, A0A7C9H0Z9, or A0A7J0AY55 (which are hereby incorporated by reference in their entirety) or a variant or homolog having substantial identity thereto. In some embodiments, the Cas12a protein is selected from the group consisting of a Cas12a nuclease, a Cas12a nickase, and a nuclease dead Cas12a ("dCas12a").

In some embodiments, the Cas protein is a Cas12b protein. As used herein, the term "Cas12b protein" or "Cas12b" includes any of the recombinant or naturally-occurring forms of the CRISPR-associated protein 12 (Cas12b) or variants or homologs thereof. In some embodiments, the variants or homologs have at least 90%, 95%, 96%, 97%, 98%, 99% or 100% amino acid sequence identity across the whole sequence or a portion of the sequence (e.g., a 50, 100, 150, or 200 continuous amino acid portion) compared to a naturally occurring Cas12b protein. In some embodiments, the Cas12b protein is substantially identical to the protein identified by the UniProt reference number T0D7A2, A0A613SPI6, A0A617FUC4, A0A6N9TP17, A0A6M1UF64, A0A7Y8V748, A0A7X7KIS4, A0A7X8X2U5, or A0A7X8UMW7 (which are hereby incorporated by reference in their entirety) or a variant or homolog having substantial identity thereto. In some embodiments, the Cas 12b protein is selected from the group consisting of a Cas12b nuclease, a Cas12b nickase, and a nuclease dead Cas12b ("dCas12b").

As used herein, the term "guide RNA" or "gRNA" refers to a ribonucleotide sequence capable of binding a nucleoprotein, thereby forming ribonucleoprotein complex. In accordance with the methods and systems of the present disclosure, the guide RNA comprises (i) a DNA-targeting sequence that is complementary to a target nucleic acid sequence of ZNF274, MAX, E2F6, IKZF3, or STAT3 sequence and (ii) a binding sequence for the Cas protein (e.g., Cas9 nuclease, Cas9 nickase, dCas9, Cas12a nuclease, Cas12a nickase, or dCas12a).

In some embodiments, the guide RNA is a single guide RNA molecule (single RNA nucleic acid), which may include a "single-guide RNA" or "sgRNA". In other embodiments, the nucleic acid of the present disclosure includes two RNA molecules (e.g., joined together via hybridization at the binding sequence). Thus, the term guide RNA is inclusive, referring both to two-molecule nucleic acids and to single molecule nucleic acids (e.g., sgRNAs).

In some embodiments, the gRNA is 10, 20, 30, 40, 50, 60, 70, 80, 90, 100 or more nucleic acid residues in length. In some embodiments, the gRNA is from 10 to 30 nucleic acid residues in length. In some embodiments, the gRNA is 20 nucleic acid residues in length. In some embodiments, the length of the gRNA is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleic acid residues or sugar residues in length. In some embodiments, the gRNA is from 5 to 50, 10 to 50, 15 to 50, 20 to 50, 25 to 50, 30 to 50, 35 to 50, 40 to 50, 45 to 50, 5 to 75, 10 to 75, 15 to 75, 20 to 75, 25 to 75, 30 to 75, 35 to 75, 40 to 75, 45 to 75, 50 to 75, 55 to 75, 60 to 75, 65 to 75, 70 to 75, 5 to 100, 10 to 100, 15 to 100, 20 to 100, 25 to 100, 30 to 100, 35 to 100, 40 to 100, 45 to 100, 50 to 100, 55 to 100, 60 to 100, 65 to 100, 70 to 100, 75 to 100, 80 to 100, 85 to 100, 90 to 100, 95 to 100, or more residues in length. In some embodiments, the gRNA is from 10 to 15, 10 to 20, 10 to 30, 10 to 40, or 10 to 50 residues in length.

In some embodiments, a CRISPR/Cas system is targeted to silence ZNF274 gene expression, and the guide RNA comprises a nucleotide sequence that is complementary to a portion of a ZNF274 gene sequence.

In some embodiments, a CRISPR/Cas system is targeted to silence MAX gene expression, and the guide RNA comprises a nucleotide sequence that is complementary to a portion of a MAX gene sequence.

In some embodiments, a CRISPR/Cas system is targeted to silence E2F6 gene expression, and the guide RNA comprises a nucleotide sequence that is complementary to a portion of a E2F6 gene sequence.

In some embodiments, a CRISPR/Cas system is targeted to silence IKZF3 gene expression, and the guide RNA comprises a nucleotide sequence that is complementary to a portion of a IKZF3 gene sequence.

In some embodiments, a CRISPR/Cas system is targeted to silence STAT3 DNA expression, and the guide RNA comprises a nucleotide sequence that is complementary to a portion of a STAT3 gene sequence.

In some embodiments, the CRISPR/Cas-system targeted to silence ZNF274 expression, MAX expression, E2F6 expression, IKZF3 expression, and/or STAT3 expression is a CRISPRi system. As used herein, the term "CRISPR interference" or "CRISPRi" refers to a system that allows for sequence-specific repression of gene expression. CRISPRi systems comprise nuclease dead Cas ("dCas") proteins (i.e., nuclease-inactivated Cas proteins) to block the transcription of a target gene, without cutting the target DNA sequence. Nuclease inactivated Cas proteins and methods of generating nuclease-inactivated Cas proteins are well known in the art (see, e.g., Qi et al., "Repurposing CRISPR as an RNA-Guided Platform for Sequence-Specific Control of Gene Expression," Cell 152(5):1173-1183 (2013), which is hereby incorporated by reference in its entirety).

The CRISPRi system suitable for use as described herein may comprise (i) a nuclease dead Cas (dCas) protein (i.e., a nuclease-inactivated Cas protein) or nucleic acid molecule encoding the dCas protein and (ii) a guide RNA comprising a nucleotide sequence that is complementary to a portion of ZNF274, MAX, E2F6, IKZF3, and STAT3.

In some embodiments, the nuclease dead Cas (dCas) protein is selected from the group consisting of dCas9, dCas12a, and dCas12b.

In some embodiments, the nuclease dead Cas (dCas) protein is a fusion protein comprising a Cas protein and one or more epigenetic modulators that suppress or silence the expression of the target gene, i.e., ZNF274, MAX, E2F6, IKZF3, and STAT3.

Suitable epigenetic modulators include, but are not limited to, DNA methyltransferase enzymes (e.g., DNA methyltransferase 3 alpha ("DNMT3A") and DNA methyltransferase 3 like ("DNMT3L")), histone demethylation enzymes (e.g., lysine-specific histone demethylase 1 ("LSD1")), histone methyltransferase enzymes (e.g., G9A and SuV39 h1), transcription factor recruitment domains (e.g., Krüppel-associated box domain ("KRAB"), KRAB-Methyl-CpG binding protein 2 domain ("KRAB-MeCP2"), enhancer of Zeste 2 ("EZH2")), zinc finger transcriptional repressor domains (e.g., spalt like transcription factor 1 ("SALL1") and suppressor of defective silencing protein 3 ("SDS3")) (see, e.g., Brezgin et al., "Dead Cas Systems: Types, Principles, and Applications," Int. J. Mol. Sci. 20:6041 (2019), which is hereby incorporated by reference in its entirety).

In some embodiments, the epigenetic modulator is selected from the group consisting of DNMT3A, DNMT2L, LSD1, KRAB, KRAB-MeCP2, EZH2, SALL1, SDS3, G9A, and Suv39 h1 (see, e.g., Yeo et al., "An Enhanced CRISPR Repressor for Targeted Mammalian Gene Regulation," 15(8): 611-616 (2018); Alerasool et al., "An Efficient KRAB Domain for CRISPRi Applications in Human Cells," Nature Methods 17:1093-1096 (2020); and Duke et al., "An Improved CRISPR/dCas9 Interference Tool for Neuronal Gene Suppression," Frontiers in Genome Editing 2:9 (2020), which are hereby incorporated by reference in their entirety).

In some embodiments, the ZNF274 inhibitor is a CRISPRi system targeted to silence ZNF274 DNA expression, and the guide RNA comprises a nucleotide sequence that is complementary to a portion of a ZNF274 gene sequence.

In some embodiments, the MAX inhibitor is a CRISPRi system targeted to silence MAX DNA expression, and the guide RNA comprises a nucleotide sequence that is complementary to a portion of a MAX gene sequence.

In some embodiments, the E2F6 inhibitor is a CRISPRi system targeted to silence E2F6 DNA expression, and the guide RNA comprises a nucleotide sequence that is complementary to a portion of a E2F6 gene sequence.

In some embodiments, the IKZF3 inhibitor is a CRISPRi system targeted to silence IKZF3 DNA expression, and the guide RNA comprises a nucleotide sequence that is complementary to a portion of a IKZF3 gene sequence.

In some embodiments, the STAT3 inhibitor is a CRISPRi system targeted to silence STAT3 DNA expression, and the guide RNA comprises a nucleotide sequence that is complementary to a portion of a STAT3 gene sequence.

In some embodiments, the agent that suppresses ZNF274, MAX, E2F6, IKZF3 and/or STAT3 comprises one or more expression vectors that express one or more transcription factor inhibitors selected from the group consisting of ZNF274 inhibitors, MAX inhibitors, E2F6 inhibitors, IKZF3 inhibitors and IKZF3 inhibitors. Each expression vector comprises (1) a nucleotide sequence encoding one or more nucleic acid inhibitors for ZNF274, MAX, E2F6, IKZF3 and/or IKZF3, and (2) a regulatory sequence operably linked to the nucleotide sequence. In some embodiments, the regulatory sequence comprises a glial cell specific promoter selected from the group consisting of PDGFRA promoter, ZNF488 promoter, GPR17 promoter, OLIG2 promoter, CSPG4 promoter, and SOX10 promoter. In some embodiments, the regulatory sequence comprises an inducible promoter or promoter system, such as tetracycline controlled inducible system, cumate-controlled inducible system and rapamycin controlled inducible systems, which are described in more detail infra.

In some embodiments, the one or more expression vectors comprises a plasmid vector, a viral vector, or a bacterial vector. In some embodiments, one or more expression vectors comprises a viral vector selected from the group consisting of adenoviruses, AAV, retroviruses, lentiviruses, vaccinia viruses, and herpes viruses. In some embodiments, the one or more expression vectors comprises a lentiviral vector. In some embodiments, the one or more expression vectors comprises a retroviral vector. In other embodiments, the one or more expression vectors comprises an AAV vector. Methods for generating and isolating viral vectors suitable for use as expression vectors are described in more details infra.

IV. Expression Vectors

Another aspect of the disclosure relates to an expression vector described in this application. In some embodiments, the expression vector expresses one or more transcription factors selected from the group consisting of BCL11A, HDAC2, EZH2, MYC, HMGA2, NFIB and TEAD2, wherein the expression vector comprises (1) a nucleotide sequence encoding one or more transcription factors selected from the group consisting of BCL11A, HDAC2, EZH2, MYC, HMGA2, NFIB and TEAD2, and (2) a regulatory sequence operably linked to the nucleotide sequence In some embodiments, the expression vector comprises (1) a nucleotide sequence encoding one or more nucleic acid inhibitors for ZNF274, MAX, E2F6, IKZF3 and/or IKZF3, and (2) a regulatory sequence operably linked to the nucleotide sequence.

In some embodiments, the regulatory sequence comprises a glial cell specific promoter selected from the group consisting of PDGFRA promoter, ZNF488 promoter, GPR17 promoter, OLIG2 promoter, CSPG4 promoter, and SOX10 promoter.

In some embodiments, the regulatory sequence comprises an inducible promoter and/or operator system sequence. Inducible promoters and/or operator systems that may be used in performing the methods or included in the systems of the present disclosure include those regulated by hormones and hormone analogs such as progesterone, ecdysone and glucocorticoids as well as promoters which are regulated by tetracycline, heat shock, heavy metal ions, interferon, and lactose operon activating compounds. An inducible promoter and/operator system is capable of directly or indirectly activating transcription of the nucleic acid molecule that it is operatively coupled to in response to a "regulatory agent" (e.g., a chemical agent or biological molecule, such as a metabolite, a small molecule) or a stimulus. In the absence of a "regulatory agent" or stimulus, the nucleotide sequence operably linked to the inducible promoter and/or operator system will not be transcribed or will not be substantially expressed.

The term "not be transcribed" or "not substantially expressed" means that the level of transcription is at least 50-fold lower than the level of transcription observed in the presence of an appropriate stimulus or regulatory agent; and preferably at least 100-fold, 250-fold, or 500-fold or lower than the level of transcription observed in the presence of an appropriate stimulus or regulatory agent. For a review of these systems see Gingrich & Roder, "Inducible Gene Expression in the Nervous System of Transgenic Mice," Annu. Rev. Neurosci. 21:377-405 (1998), which is hereby incorporated by reference in its entirety.

Suitable inducible promoter and/or operator systems for inclusion in the expression vector of the present disclosure are well known in the art and include, without limitation, tetracycline-controlled operator systems, cumate-controlled operator systems, rapamycin inducible systems, FKCsA inducible system, and ABA inducible system (see, e.g., Kallunki et al., "How to Choose the Right Inducible Gene Expression System for Mammalian Studies?" Cells 8(8):796 (2019); U.S. Pat. Nos. 8,728,759; and 7,745,592, which are hereby incorporated by reference in their entirety).

In some embodiments, the tetracycline-controlled operator system comprises a repression-based configuration, in which a Tet operator ("TetO") is inserted between a constitutive promoter and gene of interest and where the binding of the Tet repressor ("TetR") to the operator suppresses downstream transcription of a nucleic acid sequence of interest (see, e.g., Kallunki et al., "How to Choose the Right Inducible Gene Expression System for Mammalian Studies?" Cells 8(8):796 (2019), which is hereby incorporated by reference in its entirety). In accordance with such embodiments, the addition of tetracycline (or the synthetic tetracycline derivative doxycycline) results in the disruption of the association between TetR and TetO, thereby triggering TetO-dependent transcription of the nucleic acid sequence of interest.

In some embodiments, the tetracycline-controlled operator system comprises a Tet-off configuration, where tandem TetO sequences are positioned upstream of a minimal promoter followed by a nucleic acid sequence of interest (see, e.g., Kallunki et al., "How to Choose the Right Inducible Gene Expression System for Mammalian Studies?" Cells 8(8):796 (2019), which is hereby incorporated by reference in its entirety). In accordance with such embodiments, a chimeric protein consisting of TetR and VP16 ("tTA"), a eukaryotic transactivator derived from herpes simplex virus type 1, is converted into a transcriptional activator, and the expression plasmid is transfected together with the operator plasmid. Thus, the presence of tetracycline (or the synthetic tetracycline derivative doxycycline) switches off the expression of the system or its components, while removing tetracycline switches it on.

In some embodiments, the tetracycline-controlled operator system comprises a Tet-on configuration, where the system or its components is transcribed when tetracycline is present (see, e.g., Kallunki et al., "How to Choose the Right Inducible Gene Expression System for Mammalian Studies?" Cells 8(8):796 (2019), which is hereby incorporated by reference in its entirety). In accordance with such embodiments, tandem TetO sequences are positioned upstream of a minimal promoter followed by a nucleic acid sequence of interest. In the presence of tetracycline (or the 5 synthetic tetracycline derivative doxycycline), a mutant rTa ("rtTa") binds to TetO sequences, thereby activating the minimal promoter.

In some embodiments, the inducible promoter and/or operator system is a cumate-controlled operator system. Similar to the tetracycline-controlled operator system, the cumate-controlled operator system, the cumate operator ("CuO") and its repressor ("CymR") may be engineered into a repressor configuration, an activator configuration, and a reverse activator configuration (see, e.g., Kallunki et al., "How to Choose the Right Inducible Gene Expression System for Mammalian Studies?" Cells 8(8):796 (2019), which is hereby incorporated by reference in its entirety).

In some embodiments, the cumate-controlled operator system comprises a repression-based configuration, in which the cumate operator ("CuO") is inserted between a constitutive promoter and gene of interest and where the binding of the cumate repressor ("CymR") to the operator suppresses downstream transcription of the system (or system components) as described herein. In accordance with such embodiments, the addition of cumate releases CymR thereby triggering CuO-dependent expression of the system or system components.

In some embodiments, the cumate-controlled operator system comprises an activator configuration, where chimeric molecular ("cTA") is formed via the fusion of CymR and VP16. In this configuration, a minimal promoter is placed downstream of the multimerized operator binding sites (e.g., 6×CuO). Transcription of a nucleic acid sequence of interest is controlled by the minimal promoter, which is activated in the absence of cumate.

In some embodiments, the cumate-controlled operator system comprises a reverse activator configuration, where a nucleic acid sequence is transcribed when cumate is present. In accordance with such embodiments, tandem CuO sequences are positioned upstream of a minimal promoter followed by a nucleic acid sequence of interest. In the presence of cumate, a cTA mutant ("rcTA") binds to CuO sequences, thereby activating the minimal promoter.

In some embodiments, the inducible promoter and/or operator system is a rapamycin inducible system. In accordance with such embodiments, the promoter is a rapamycin-inducible promoter (e.g., a minimal IL-2 promoter). In this system, a DNA 25 binding domain (ZFHD1) and a transcription factor activation domain (NF-KB p65) are expressed separately as fusion proteins with the rapamycin-binding domains of FKBP12 and FRAP (mTOR), respectively (see, e.g., Koh et al., "Use of a Stringent Dimerizer-Regulated Gene Expression System for Controlled BMP2 Delivery," Mol. Ther. 14(5):P684-691 (2006), which is hereby incorporated by reference in its entirety). On addition of rapamycin (or the rapamycin analog FK506), the fusion proteins are reversibly cross-linked to drive transcription of a nucleic acid sequence of interest. Mutation of the rapamycin-binding region of the mTOR-activation domain fusion protein results in systems responsive to rapamycin-like compounds (rapalogs) that, unlike rapamycin, do not bind to endogenous mTOR protein and, therefore, have little immunosuppressive or antiproliferative activity.

In some embodiments, the regulatory sequence comprises a human elongation factor 1α promoter ("EF1A"), 5 cytomegalovirus ("CMV") promoter, human ubiquitin C promoter ("UBC"), chicken beta-actin promoter, hybrid chicken beta-actin promoter (CBh) and phosphoglycerokinase ("PGK") promoter. In accordance with such embodiments, the promoter may be modified to comprise one, two, three, or more Tet operator (TetO) sites or one, two, three, four, five, six, or more CuO sites Additional suitable promoters for inclusion in the expression vectors of the present application include, but are not limited to, H1 promoter and U6 promoter. In some embodiments, when the inducible promoter and/or operator system is operatively linked to the nucleotide sequence encoding one or more guide RNAs in a Cas system, the promoter is an H1 promoter or a U6 promoter. The H1 promoter may be a modified H1 promoter comprising one, two, three, or more Tet operator (TetO) sites. The U6 promoter may be a modified U6 promoter comprising one, two, or three Tet operator (TetO) sites or one, two, three, four, five, six, or more CuO sites (see, e.g., Sun et al., "Development of Drug-20 Inducible CRISPR-Cas9 Systems for Large-Scale Functional Screening," BMC Genomics 20:225 (2019), which is hereby incorporated by reference in its entirety).

In some embodiments, the regulatory sequence may further comprise a transcriptional enhancer binding site, a RNA polymerase initiation site, a ribosome binding site, and/or other sites that facilitate the expression of the nucleotide sequence operably linked to the regulatory sequence in the expression vector.

In some embodiments, the expression vector encodes a system for inducing rejuvenation of a population of adult glial progenitor cells or treating myelin deficiency in a subject.

In some embodiments, the system for inducing rejuvenation of a population of adult glial progenitor cells or treating myelin deficiency in a subject is a nuclease dead Cas (dCas) system. This system comprises a first nucleic acid molecule encoding a fusion protein comprising a nuclease dead Cas (dCas) protein fused to an epigenetic modulator; a second nucleic acid molecule encoding one or more guide RNAs, where the one or more guide RNAs each comprise an RNA sequence that hybridizes to a portion of a DNA sequence of ZNF274, MAX, E2F6, IKZF3, and/or STAT3; and an inducible promoter and/or operator system that is operatively linked to the first nucleic acid molecule, the second nucleic acid molecule, or both. In some embodiments, the inactivated Cas protein (dCas) is selected from the group consisting of dCas9, dCas12a, and dCas12b (see, e.g., Brezgin et al., "Dead Cas Systems: Types, Principles, and Applications," Int. J. Mol. Sci. 20:6041 (2019), which is hereby incorporated by reference in its entirety).

Suitable epigenetic modulators are described in detail supra. In some embodiments, the epigenetic modulator is selected from the group consisting of DNMT3A, DNMT2L, LSD1, KRAB, KRAB-MeCP2, EZH2, SALL1, SDS3, G9A, Suv39 h1, Cs, and WRPW (see, e.g., Yeo et al., "An Enhanced CRISPR Repressor for Targeted Mammalian Gene Regulation," 15(8):611-616 (2018); Alerasool et al., "An Efficient KRAB Domain for CRISPRi Applications in Human Cells," Nature Methods 17:1093-1096 (2020); and Duke et al., "An Improved CRISPR/dCas9 Interference Tool for Neuronal Gene Suppression," Frontiers in Genome Editing 2:9 (2020), which are hereby incorporated by reference in their entirety). In some embodiments, when methylation of a gene or gene promoter is effective to suppress its transcription, the epigenetic modulator is a methyltransferase.

In some embodiments, the epigenetic modulator is selected from the group consisting of Tet methylcytosine dioxygenase 1 ("TET1"), SunTag-TET1, MS2/MCP-TET1, p300Core, four tandem copies of herpes simplex viral protein 16 ("VP64"), VP160, NF-κB p65 activation domain ("p65"), Epstein-Barr Virus-derived R transactivator ("Rta"), SunTag-VP64, VP64-p65-Rta ("VPR"), SunTag-p65-HSF1, TV, synergistic activation mediator ("SAM"), Three-Component Repurposed Technology for Enhanced Expression ("TREE"), Casilio, Scaffold, and CMV (see, e.g., Brezgin et al., "Dead Cas Systems: Types, Principles, and Applications," Int. J. Mol. Sci. 20(23):6041 (2019), which is hereby incorporated by reference in its entirety). In some embodiments, when demethylation of a gene or gene protein is effective to suppress its transcription, the epigenetic modulator is a demethylase (e.g., TET1).

In some embodiments, the system for inducing rejuvenation in a population of adult glial progenitor cells or treating myelin deficiency in a subject comprises a dCas fusion protein, where the dCas is fused to a methyltransferase. In any embodiment, the system for inducing rejuvenation in a population of adult glial progenitor cell or treating myelin deficiency in a subject comprises a dCas fusion protein, where the dCas is fused to a demethylase.

Exemplary dCas fusion proteins and dCas fusion protein systems for use according to the methods of the present disclosure are identified in Table 9 below.

TABLE 9

Exemplary Cas Fusion Proteins

| | |
|---|---|
| dCas9-TET1 | Liu et al., "Editing DNA Methylation in the Mammalian Genome," *Cell* 167: 233-247 (2016) |
| dCas9-SunTag-TET1 | Morita et al., "Targeted DNA Demethylation in vivo using dCas9-Peptide Repeat and scFv-TET1 Catalytic Domain Fusions," *Nat. Biotechnol.* 34: 1060-1065 (2016) |
| dCas9-MS2/MCP-TET1 | Xu et al., "A CRISPR-Based Approach for Targeted DNA Demethylation," *Cell Discov.* 2: 16009 (2016) |
| dCas9-P300 Core | Hilton et al., "Epigenome Editing by a CRISPR/Cas9-Based Acetyltransferase Activates Genes from Promoter and Enhancers," *Nat. Biotechnol.* 33(5): 510-517 (2015) |

TABLE 9-continued

| Exemplary Cas Fusion Proteins | |
|---|---|
| dCas9-VP64 | Gilbert et al., "CRISPR-Mediated Modular RNA-Guided Regulation of Transcription in Eukaryotes," *Cell* 154: 442-451 (2013) |
| dCas9-VP160 | Cheng et al., "Multiplexed Activators of Endogenous Genes by CRISPR-on, an RNA-Guided Transcriptional Activator System," *Cell Res.* 23: 1163 (2013) |
| dCas9-p65 | Gilbert et al., "CRISPR-Mediated Modular RNA-Guided Regulation of Transcription in Eukaryotes," *Cell* 154: 442-451 (2013) |
| dCas9-VPR | Chavez et al., "Highly Efficient Cas9-Mediated Transcriptional Programming," *Nat. Methods.* 12: 326 (2015) |
| dCas9 SAM system | Konermann et al., "Genome-Scale Transcriptional Activation by an Engineered CRISPR-Cas9 Complex," *Nature* 517(7536): 583-588 (2015) |
| dCas9 TREE system | Kunii et al., "Three-Component Repurposed Technology for Enhanced Expression: Highly Accumulable Transcriptional Activators via Branched Tag Arrays," *CRISPR J.* 1(5): 337-347 (2018) |
| dCas9-TV (i.e., dCas9-6TAL-VP128) | Li et al., "A potent Cas9-Derived Gene Activator for Plant and Mammalian Cells," *Nat. Plants.* 3: 930-936 (2017) |
| dCas12a-VPR | Liu et al., "Engineering Cell Signaling Using Tunable CRISPR-Cpf1-Based Transcription Factors," *Nat. Commun.* 8: 2095 (2017) |
| dCas12a-p65 | Tak et al., "Inducible and Multiplex Gene Regulation Using CRISPR-Cpf1-Based Transcription Factors," *Nat. Methods* 14: 1163-1166(2017) |

*Each of which is hereby incorporated by reference in its entirety.

In some embodiments, the dCas protein is a dCas9 or dCas 12 protein.

In some embodiments, the first and second nucleic acid molecules of this dCas system are contained in a single expression vector. In some embodiments, the first and second nucleic acid molecules of this system are contained in separate expression vectors.

In some embodiments, the system for inducing rejuvenation of a population of adult glial progenitor cells or treating myelin deficiency in a subject is a Cas system. This system comprises a first nucleic acid molecule encoding a Cas protein; a second nucleic acid molecule encoding one or more guide RNAs, where said one or more guide RNAs each comprise an RNA sequence that hybridizes to a portion of a DNA sequence of ZNF274, MAX, E2F6, IKZF3, and/or STAT3; and an inducible promoter and/or operator system that is operatively linked to the first nucleic acid molecule, the second nucleic acid molecule, or both.

In some embodiments, this Cas nuclease system comprises a Cas9 protein or a Cas12 protein (e.g., Cas12a or Cas12b). Suitable Cas proteins and derivatives thereof for inclusion in the systems according to the present disclosure are well known in the art and are described in more detail supra.

In some embodiments, the first and second nucleic acid molecules of this Cas nuclease system are contained in a single expression vector. In some embodiments, the first and second nucleic acid molecules are contained in separate expression vectors.

In some embodiments, the system for inducing rejuvenation of a population of adult glial progenitor cells or treating myelin deficiency in a subject is a gene-editing nuclease system. This system comprises: a first nucleic acid molecule encoding a first sequence specific gene editing nuclease comprising a first DNA binding motif, where the first DNA binding motif binds to a first DNA sequence of ZNF274, MAX, E2F6, IKZF3 and/or STAT3, respectively; a second nucleic acid molecule encoding a second sequence specific gene editing nuclease comprising a second DNA binding motif, where said second DNA binding motif binds to a second DNA sequence of ZNF274, MAX, E2F6, IKZF3 and/or STAT3, respectively; and an inducible promoter and/or operator system sequence that is operatively coupled to the first nucleic acid molecule, the second nucleic acid molecule, or both the first and second nucleic acid molecules.

Suitable sequence specific gene editing nucleases for inclusion the systems according to the present disclosure are well known in the art and include, without limitation, zinc finger nucleases ("ZFNs") and transcription activator-like effector nucleases ("TALENs").

In one embodiment, the sequence specific gene editing nucleases of the system described herein is a ZFN. A ZFN is an artificial endonuclease that comprises at least 1 zinc finger motif (e.g., at least 2, 3, 4, or 5 zinc finger motifs) fused to a nuclease domain (e.g., the cleavage domain of the FokI restriction enzyme). Heterodimerization of two individual ZFNs at a target nucleic acid sequence can result in cleavage of the target sequence. For example, two individual ZFNs may bind opposite strands of a target DNA sequence to induce a double-strand break in the target nucleic acid sequence. Methods of designing suitable ZFNs for inclusion in the systems of the presently claimed disclosure are well known in the art (see, e.g., Urnov et al., "Genome Editing with Engineered Zinc Finger Nucleases," Nat. Rev. Genet. 11 (9): 636-646 (2010); Gaj et al., "Targeted Gene Knockout by Direct Delivery of Zinc-Finger Nuclease Proteins," Nat. Methods 9(8):805-807 (2012); U.S. Pat. Nos. 6,534,261; 6,607,882; 6,746,838; 6,794,136; 6,824,978; 6,866,997; 6,933,113; 6,979,539; 7,013,219; 7,030,215; 7,220,719; 7,241,573; 7,241,574; 7,585,849; 7,595,376; 6,903,185; and 6,479,626, which are hereby incorporated by reference in their entirety). In some embodiments, the first and second gene editing nucleases are FokI nucleases. In accordance with such embodiments, the first and second DNA binding motifs are zinc finger motifs.

In some embodiments, the sequence specific gene editing nucleases of the system described herein is a TALEN. A TALEN is an engineered transcription activator-like effector nuclease that comprise a DNA-binding domain and a nuclease domain (e.g., a cleavage domain of the FokI restriction enzyme). The DNA-binding domain comprises a series of 33-35 amino acid repeat domains that each recognize a single base pair. Heterodimerization of two individual TALENs at a target nucleic acid sequence can result in cleavage of the target sequence. For example, two individual TALENs may bind opposite strands of a target DNA sequence to induce a double-strand break in the target nucleic acid sequence. Methods of designing suitable ZFNs for inclusion in the systems of the presently claimed disclosure are well known in the art (see, e.g., Scharenberg et al., "Genome Engineering with TAL-Effector Nucleases and Alternative Modular Nuclease Technologies," Curr. Gene Ther. 13(4): 291-303 (2013); Gaj et al., "Targeted Gene Knockout by Direct Delivery of Zinc-Finger Nuclease Proteins," Nat. Methods 9(8):805-807 (2012); Beurdeley et al., "Compact Designer TALENs for Efficient Genome Engineering," Nat. Commun. 4:1762 (2013); U.S. Pat. Nos. 8,440,431; 8,440,432; 8,450,471; 8,586,363; and 8,697,853, which are hereby incorporated by reference in their entirety). In some embodiments, the first and second gene editing nucleases are FokI nucleases. In accordance with such embodiments, the first and second DNA binding motifs are TALE motifs.

In some embodiments, the first and second nucleic acid molecules of the sequence specific gene editing nuclease systems described herein are contained in a single expression vector. In some embodiments, the first and second nucleic acid molecules are contained in separate expression vectors.

In all systems described herein for rejuvenating glial progenitor cells or treating myelin deficiency in a subject, the first and/or second nucleic acid molecules of the system are operatively coupled to an inducible promoter and/or operator system as described in more details above.

In some embodiments, the expression vector of the present application is a plasmid vector, a viral vector, or a bacterial vector.

In some embodiments, the expression vector of the present application is a lentiviral vector (see, e.g., U.S. Pat. No. 748,529 to Fang et al.; Ura et al., "Developments in Viral Vector-Based Vaccines," Vaccines 2:624-641 (2014); and Hu et al., "Immunization Delivered by Lentiviral Vectors for Cancer and Infection Diseases," Immunol. Rev. 239:45-61 (2011), 15 which are hereby incorporated by reference in their entirety).

In some embodiments, the expression vector of the present application is a retroviral vector (see e.g., U.S. Pat. No. 748,529 to Fang et al., and Ura et al., "Developments in Viral Vector-Based Vaccines," Vaccines 2:624-641 (2014), which are hereby incorporated by reference in their entirety), a vaccinia virus, a replication deficient adenovirus vector, and a gutless adenovirus vector (see e.g., U.S. Pat. No. 5,872,005, which is incorporated herein by reference in its entirety).

In other embodiments, the expression vector of the present application is an adeno-associated virus (AAV) vector (see, e.g., Krause et al., "Delivery of Antigens by Viral Vectors for Vaccination," Ther. Deliv. 2(1):51-70 (2011); Ura et al., "Developments in Viral Vector-Based Vaccines," Vaccines 2:624-641 (2014); Buning et al, "Recent Developments in Adeno-associated Virus Vector Technology," J. Gene Med. 10:717-733 (2008), each of which is incorporated herein by reference in its entirety).

Methods for generating and isolating viral expression vectors suitable for use as vectors are known in the art (see, e.g., Bulcha et al., "Viral Vector Platforms within the Gene Therapy Landscape," Nature 6:53 (2021); Bouard et al., "Viral Vectors: From Virology to Transgene Expression," Br. J. Pharmacol. 157(2): 153-165 (2009); Grieger & Samulski, "Adeno-associated Virus as a Gene Therapy Vector: Vector Development, Production and Clinical Applications," Adv. Biochem. Engin/Biotechnol. 99:119-145 (2005); Buning et al, "Recent Developments in Adeno-associated Virus Vector Technology," J. Gene Med. 10:717-733 (2008), each of which is incorporated herein by reference in its entirety).

V. Genetically Modified Glial Progenitor Cell

Aspects of the present disclosure also relate to a glial progenitor cell genetically modified with an expression vector or nucleic acid molecule of the present application. In some embodiments, the expression vector or nucleic acid molecule is integrated into the genome of the genetically modified glial progenitor cell. In some embodiments, the expression vector or nucleic acid molecule is present in an epichromosomal form in the genetically modified glial progenitor cell.

In some embodiments, the glial progenitor cell is genetically modified with a nuclease dead Cas (dCas) system, a Cas nuclease system, or a gene-editing nuclease system according to the present application.

In some embodiments, the genetically modified glial progenitor cell is a mammalian glial progenitor cell. In any embodiment, the genetically modified glial progenitor cell is a human glial progenitor cell.

Glial progenitor cells suitable for genetic modification as described here can be derived from multipotent (e.g., neural stem cells) or pluripotent cells (e.g., embryonic stem cells and induced pluripotent stem cells) using methods known in the art or described herein. In yet another embodiment, glial progenitor cells can be extracted from embryonic tissue, fetal tissue, or adult brain tissue containing a mixed population of cells directly by using the promoter specific separation technique, as described in U.S. Patent Application Publication Nos. 20040029269 and 20030223972 to Goldman, which are hereby incorporated by reference in their entirety. In accordance with this embodiment, the glial progenitor cells are isolated from ventricular or subventricular zones of the brain or from the subcortical white matter.

In some embodiments, the genetically modified glial progenitor cells are genetically modified bi-potential glial progenitor cells. In some embodiment, the genetically modified glial progenitor cells are genetically modified oligodendrocyte-biased glial progenitor cells. In some embodiments, the genetically modified glial progenitor cells are genetically modified astrocyte-biased glial progenitor cells.

In some embodiment, it may be preferable to enrich a cell preparation comprising glial progenitor cells prior to or after genetic modification to increase the concentration and/or purity of the glial progenitor cells modified to contain the expression vector or systems described herein. Accordingly, in one embodiment, A2B5 monoclonal antibody (mAb) that recognizes and binds to gangliosides present on glial progenitor cells early in the developmental or differentiation process is utilized to separate glial progenitor cells from a mixed population of cells (Nunes et al., "Identification and Isolation of Multipotential Neural Progenitor Cells From the Subcortical White Matter of the Adult Human Brain.," Nat Med. 9(4):439-47 (2003), which is hereby incorporated by reference in its entirety). Using the A2B5 mAb, glial progenitor cells can be separated, enriched, or purified from a mixed population of cell types. In another embodiment, selection of CD140α/PDGFRα positive cells is employed to produce a purified or enriched preparation of bi-potential glial progenitor cells. In another embodiment, selection of CD9 positive cells is employed to produce a purified or enriched preparation of oligodendrocyte-biased glial progenitor cells. In yet another embodiment, both CD140a/PDGFRa and CD9 positive cell selection is employed to produce a purified or enriched preparation of oligodendrocyte-biased glial progenitor cells. In another embodiment, selection of CD44 positive cells is employed to produce a purified or enriched preparation of astrocyte-biased glial progenitor cells (Liu et al., "CD44 Expression Identifies Astrocyte-Restricted Precursor Cells," Dev. Biol. 276(1):31-46 (2004), which is hereby incorporated by reference in its entirety.) In another embodiment, both CD140a/PDGFRa and CD44 positive cell selection is employed to produce a purified or enriched preparation of oligodendrocyte-biased glial progenitor cells. In another embodiment, CD140a/PDGFRa, CD9, and CD44 positive cell selection is employed to produce a purified or enriched preparation of oligodendrocyte-biased glialprogenitor cells.

A further aspect of the present disclosure is directed to a preparation of glial progenitor cells expressing the genetic construct according to the present disclosure.

The examples below are intended to exemplify the practice of embodiments of the disclosure but are by no means intended to limit the scope thereof.

EXAMPLES

Materials and Methods

Cell Lines

The human iPSC line C27 was used to generate hGPCs in which predicted transcripts of interest were validated. The C27 line is male. Cells were differentiated into GPCs as detailed in Human iPSC-derived production of GPCs (Chambers et al., "Highly Efficient Neural Conversion of Human ES and iPS Cells by Dual Inhibition of SMAD Signaling," Nat Biotechnol 27:275-280 (2009), which is hereby incorporated by reference in its entirety).

Adult and Fetal Brain Processing for Cell Isolation

Human brain samples were obtained under approved Institutional Review Board protocols from consenting patients at Strong Memorial Hospital at the University of Rochester. Brain tissue was obtained from normal GW 18-24 cortical and/or VZ/SVZ dissections or adult white matter/cortex epileptic resections (18F,19M, and 27F years old for mRNA, 8M, 20F, 43M, and 54F years old for miRNA). Fetal GPC acquisition, dissociation and immunomagnetic sorting of A2B5+/PSA-NCAM− cells were as described (Windrem et al., "Fetal and Adult Human Oligodendrocyte Progenitor Cell Isolates Myelinate the Congenitally Dysmyelinated Brain," Nat. Med. 10:93-97 (2004), which is hereby incorporated by reference in its entirety). GPCs were isolated from dissociated tissue using a dual immunomagnetic sorting strategy: depleting mouse anti-PSA-NCAM+ (Millipore, DSHB) cells, using microbead tagged rat anti-mouse IgM (Miltenyi Biotech), then selecting A2B5+ (clone 105; ATCC, Manassas, VA) cells from the PSA-NCAM− pool, as described (Windrem et al., "Fetal and Adult Human Oligodendrocyte Progenitor Cell Isolates Myelinate the Congenitally Dysmyelinated Brain," Nat. Med. 10:93-97 (2004) and Windrem et al., "Neonatal Chimerization with Human Glial Progenitor Cells can both Remyelinate and Rescue the Otherwise Lethally Hypomyelinated Shiverer Mouse," Cell Stem Cell 2:553-565 (2008), which are hereby incorporated by reference in their entirety). After sorting, cells were maintained for 1-14 days in DMEM-F12/N1 with 10 ng/ml bFGF and 20 ng/ml PDGF-AA. Alternatively, CD140a/PDGF□R-defined GPCs were isolated and sorted using MACS as previously described (Sim et al., "CD140a Identifies a Population of Highly Myelinogenic, Migration-Competent and Efficiently Engrafting Human Oligodendrocyte Progenitor Cells," Nat. Biotechnol. 29:934-941 (2011b), which is hereby incorporated by reference in its entirety), yielding an enriched population of CD140+ glial progenitor cells.

Bulk RNA-Sequencing

RNA was purified from isolates via Qiagen RNeasy kits and bulk RNA sequencing libraries were constructed. Samples were sequenced deeply on an Illumina HiSeq 2500 at the University of Rochester Genomics Research Center. Raw FASTQ files were trimmed and adapters removed using fastp (Chen et al., "fastp: An Ultra-fast All-in-one FASTQ Preprocessor," Bioinformatics 34:1884-1890 (2018), which is hereby incorporated by reference in its entirety) and aligned to GRCh38 using Ensembl 95 gene annotations via STAR in 2-pass mode across all samples (Dobin et al., "STAR: Ultrafast Universal RNA-seq Aligner," Bioinformatics 29:15-21 (2013), which is hereby incorporated by reference in its entirety) and quantified with RSEM version (Li and Dewey, "RSEM: Accurate Transcript Quantification From RNA-Seq Data With or Without a Reference Genome," BMC Bioinformatics 12:323 (2011), which is hereby incorporated by reference in its entirety). Subsequent analysis was carried out in R (R Core Team R: A Language and Environment for Statistical Computing. (Vienna, Austria: R Foundation for Statistical Computing) (2017), which is hereby incorporated by reference in its entirety) where RSEM gene level results were imported via tximport (Soneson et al., "Differential Analyses for RNA-seq: Transcript-Level Estimates Improve Gene-Level Inferences," F1000Research 4:1521 (2015), which is hereby incorporated by reference in its entirety). DE analysis was carried out in DESeq2 (Love et al., "Moderated Estimation of Fold Change and Dispersion for RNA-seq Data With DESeq2," Genome Biology 15:550 (2014), which is hereby incorporated by reference in its entirety) where paired analyses (Fetal A2B5+ vs CD140a+, fetal CD140a+ vs CD140a−) had paired information added to their models. For adult vs fetal DE analysis, age was concatenated with sort marker (CD140a− samples were not included) to define the group variable where sequencing batch was also added to the model to account for technical variability. Genes with an adjusted p-value <0.01 and an absolute log 2-fold change >1 were deemed significant. These data were then further filtered by meaningful abundance, defined as a median TPM (calculated via RSEM) of 1 in at least 1 group (20,663 genes met this criterion prior to DE).

scRNA-Seq Analysis

The fetal brain sample as processed as above for bulk rna-seq up until single cells were sorted via FACS for either CD140a+ or PSA-NCAM−/A2B5+ surface expression. Single cells were then captured on a 10× genomics chromium controller utilizing V2 chemistry and libraries generated according to manufacturer's instructions.

Samples were sequenced on an Illumina HISeq 2500 system. Demultiplexed samples were then aligned and quantified using Cell Ranger to an index generated from GRCh38 and Ensembl 95 gene annotations using only protein coding, lncRNA, or miRNA biotypes. Analysis of scRNA-Seq samples was carried out via Seurat (Butler et al., "Integrating Single-cell Transcriptomic Data Across Different Conditions, Technologies, and Species," Nat Biotechnol 36:411-420 (2018), which is hereby incorporated by reference in its entirety) within R. Both samples were merged and low-quality cells filtered out as defined by having mitochondrial gene expression greater than 15% or having fewer than 500 unique genes. Samples were then normalized utilizing SCTransform taking care to regress out contributions due to total number of UMIs, percent mitochondrial gene content or the difference in S phase and G2M phase scores of each cell. PCA was then calculated, UMAP was run using the first 30 dimensions with n.neighbors=60 and repulsion.strength=0.8. FindNeighbors was then run followed by FindClusters with resolution set to 0.35. Based on expression profiles of each cluster, some similar clusters were merged into broader cell type clusters. Static differential expression of clusters was computed using the MAST test (Finak et al., "MAST: A Flexible Statistical Framework for Assessing Transcriptional Changes and Characterizing Heterogeneity in Single-cell RNA Sequencing Data," Genome Biology 16:278 (2015), which is hereby incorporated by reference in its entirety) where an adjusted p-value of <0.01 and an absolute log 2 fold change of >0.5 was deemed significant. Prediction of active transcription factor regulons was carried out with the SCENIC package in R (Aibar et al., "SCENIC: Single-cell Regulatory Network Inference and Clustering," Nat. Methods 14:1083-1086 (2017), which is hereby incorporated by reference in its entirety) using the hg38 databases located at https://resources.aertslab.org/cistarget/. Genes were included in co-expression analyses if they were expressed in at least 1% of cells.

Ingenuity Pathway Analysis and Network Construction

Differentially expressed genes were fed into Ingenuity Pathway Analysis (Qiagen) to determine significant canonical, functional, and upstream signaling terms. For construction of the IPA network, terms were filtered for adjusted p-values below 0.001. Non-relevant IPA terms were removed along with highly redundant functional terms assessed via jaccard similarity indices using the iGraph package (Csardi, G. N., Tamas "The Igraph Software Package for Complex Network Research," InterJournal Complex Systems 1695 (2006), which is hereby incorporated by reference in its entirety). Modularity was established within Gephi (Bastian et al., "Gephi: An Open Source Software for Exploring and Manipulating Networks," (2009), which is hereby incorporated by reference in its entirety) and the final network was visualized using Cytoscape (Shannon P., "Cytoscape: A Software Environment for Integrated Models of Biomolecular Interaction Networks," Genome Res 13:2498-2504 (2003), which is hereby incorporated by reference in its entirety). Genes and terms of interest were retained for visualization purposes. Modules were broken out from one another and organized using the yFiles organic layout.

Inference of Transcription Factor Activity

Adult and fetal enriched gene lists were fed separately into RcisTarget (Aibar et al., "SCENIC: Single-cell Regulatory Network Inference and Clustering," Nat. Methods 14:1083-1086 (2017), which is hereby incorporated by reference in its entirety) to identify overrepresentation of motifs in windows around the genes' promoters (500 bp up/100 bp down and 10 kb up and 10 kb down). Transcription factors that were associated with significantly enriched motifs (NES>3) were then filtered by their significant differential expression in the input gene list. Within each window and gene list, only appropriate TF-gene interactions (Repressors downregulating genes and activators upregulating genes) were kept. Scanning windows were then merged to produce TF-gene edge lists of predicted fetal/adult repressors/activators. TFs of interest were narrowed to those primarily reported as solely activators or repressors in the literature.

miRNA Microarray Analysis

A2B5+ adult (n=3) and CD140a+ fetal (n=4) cell suspensions were isolated via MACS as noted above and their miRNA isolated using miRNeasy kits according to manufacturer instructions (QIAGEN). Purified miRNA was then prepared and profiled on Affymetrix GeneChip miRNA 3.0 Arrays as instructed by their standard protocol. Raw CEL files were then read into R via the oligo (Carvalho and Irizarry, "A Framework for Oligonucleotide Microarray Preprocessing," Bioinformatics 26:2363-2367 (2010), which is hereby incorporated by reference in its entirety) package and samples were normalized via robust multi-array averaging (RMA). Probes were then filtered for only human miRNAs according to Affymetrix's annotation, and differential expression was carried out in limma (Ritchie et al., "Limma Powers Differential Expression Analyses for RNA-Sequencing and Microarray Studies," Nucleic Acids Res 43: e47 (2015), which is hereby incorporated by reference in its entirety) where significance was established at an adjusted p-value <0.01. Finally, differentially expressed miRNAs were surveyed across five independent miRNA prediction databases using miRNAtap (Pajak M., "miRNAtap: miRNAtap: microRNA Targets-Aggregated Predictions," R Package Version 1.22.0 (2020), which is hereby incorporated by reference in its entirety) with min_src set to 2 and method set to "geom". Transcription factor regulation of miRNAs was carried out via querying the TrasmiR V2.0 database (Tong et al., "TransmiR v2.0: An Updated Transcription Factor-microRNA Regulation Database," Nucleic Acids Res 47: D253-D258 (2019), which is hereby incorporated by reference in its entirety).

Exploratory Analysis and Visualization

PCA of bulk RNA-Seq or microarray samples was computed via prcomp with default settings on variance stabilized values of DESeq2 objects. PCAs were plotted via autoplot in the ggfortify package. Volcano plots were generated using EnhancedVolcano. Graphs were further edited or generated anew using ggplot2 and aligned using patchwork.

Human iPSC-Derived Production of GPCs

Human induced pluripotent stem cells (C27 (Chambers et al., "Highly Efficient Neural Conversion of Human ES and iPS Cells by Dual Inhibition of SMAD Signaling," Nat Biotechnol 27:275-280 (2009), which is hereby incorporated by reference in its entirety)) were differentiated into GPCs using our previously described protocol (Osipovitch et al., "Human ESC-Derived Chimeric Mouse Models of Huntington's Disease Reveal Cell-Intrinsic Defects in Glial Progenitor Cell Differentiation," Cell Stem Cell 24:107-122 e107 (2019); Wang et al., "Human iPSC-Derived Oligodendrocyte Progenitor Cells Can Myelinate and Rescue a Mouse Model of Congenital Hypomyelination," Cell Stem Cell 12:252-264 (2013); and Windrem et al., "Human iPSC Glial Mouse Chimeras Reveal Glial Contributions to Schizophrenia," Cell Stem Cell 21:195-208.e196 (2017), which are hereby incorporated by reference in their entirety). Briefly, cells were first differentiated to neuroepithelial cells, then to pre-GPCs, and finally to GPCs. GPCs were maintained in glial media supplemented with T3, NT3, IGF1, and PDGF-AA.

Lentiviral Overexpression

For overexpression of E2F6, ZNF274, IKZF3, or MAX, we first identified the most abundant protein coding transcript of each of these genes from the adult hGPC dataset. cDNAs for each transcript were cloned downstream of the tetracycline response element promoter in the pTANK-TRE-EGFP-CAG-rtTA3G-WPRE vector. Viral particles pseudotyped with vesicular stomatitis virus G glycoprotein were produced by transient transfection of HEK293FT cells and concentrated by ultracentrifugation, and titrated by QPCR (qPCR Lentivirus Titer Kit, ABM-Applied Biological Materials Inc). iPSC (C27) derived GPC cultures (160-180 days in vitro) were infected at 1.0 MOI in glial media for 24 hours. Cells were washed with HBSS and maintained in glial media supplemented with 1 μg/ml doxycycline (Millipore-Sigma St. Louis, MO) for the remainder of the experiment. Transduced hGPCs were isolated via FACS on DAPI−/EGFP+expression 3, 7, and 10 days following the initial addition of doxycycline. Doxycycline control cells were sorted on DAPI-alone.

Quantitative PCR

RNA from overexpression experiments was extracted using RNeasy micro kits (Qiagen, Germany). First-strand cDNA was synthesized using TaqMan Reverse Transcription Reagents (Applied Biosystems, USA). qPCR reactions were run in triplicate by loading 1 ng of RNA mixed with FastStart Universal SybrGreen Mastermix (Roche Diagnostics, Germany) per reaction and analyzed on a real-time PCR instrument (CFX Connect Real-Time System thermocycler; Bio-Rad). Results were normalized to the expression of 18S from each sample.

Quantification and Statistical Analysis

For qPCR experiments, significant differences in delta CTs for each gene were analyzed in linear models constructed by the interaction of overexpression condition and timepoint with the addition of a cell batch covariate. Post hoc pairwise comparisons were tested via least-squares means tests against the Dox control within timepoints using the Ismeans package (Lenth, R. V., "Least-Squares Means: The R Package Ismeans," Journal of Statistical Software, Foundation for Open Access Statistics 69 (101) (2016), which is hereby incorporated by reference in its entirety). P-values were adjusted for multiple comparisons using the false discovery rate method whereby p-values<0.05 were deemed significant.

Example 1: CD140a Selection Enriches for Human Fetal Glial Progenitors More Efficiently than does A2B5

Figure 1D:
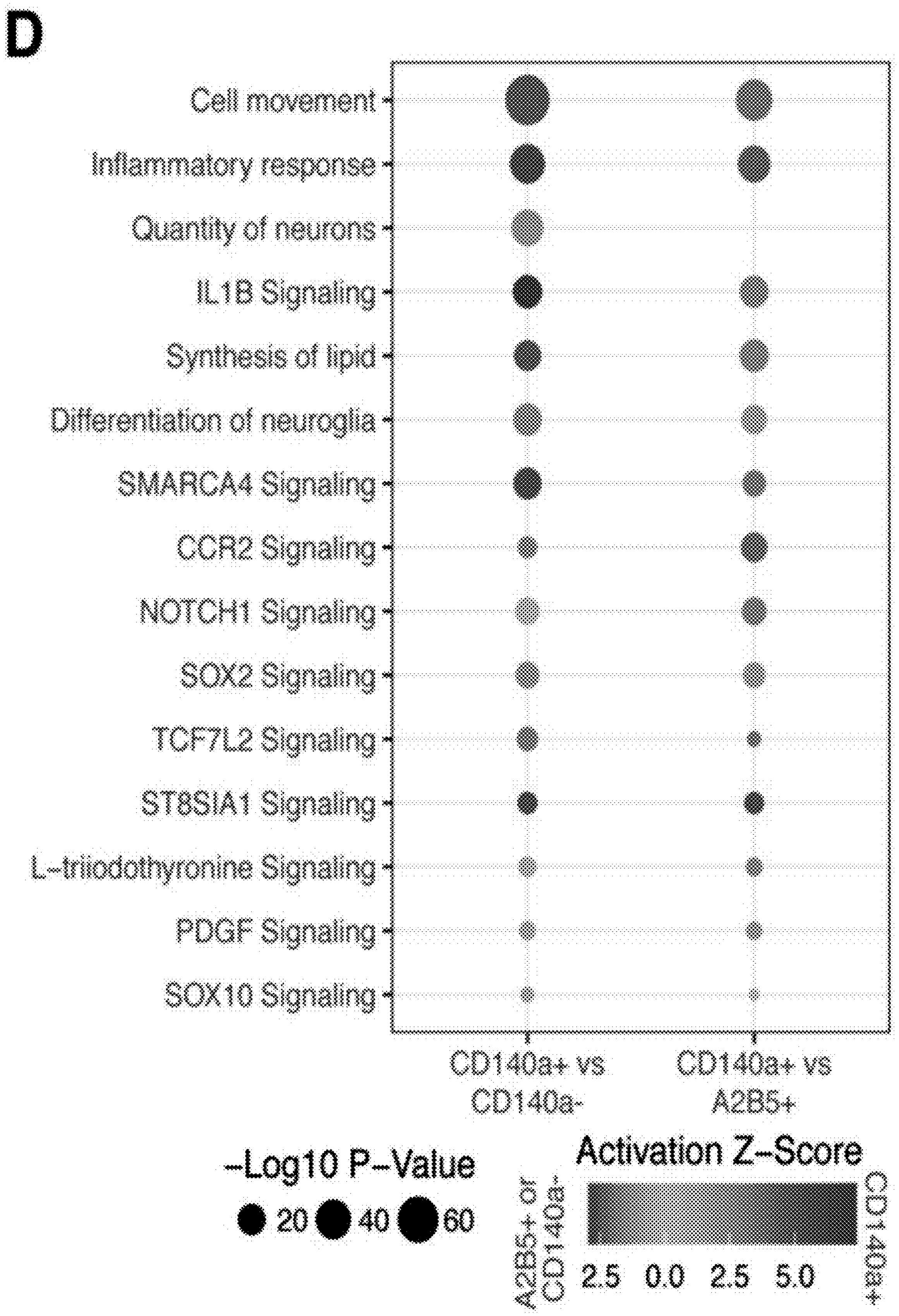
FIG. 1 shows Bulk RNA-Seq Characterization of human fetal GPCs. Panel A. Workflow of bulk and scRNA-Sequencing of CD140a+, CD140a−, and A2B5+/PSA−NCAM−-selected 2nd trimester human fetal brain isolates. Panel B. Principal component analysis of all samples across two batches. Panel C. Venn diagram of CD140a+ vs CD140a− and CD140+ vs A2B5+/PSA−NCAM− differentially-expressed gene sets (p<0.01 and absolute log 2-fold change >1). Panel D. Significant Ingenuity Pathway Analysis terms for both genesets. Size represents −log 10 p-value and color represents activation Z-Score (Blue, CD140a+; Red, A2B5+ or CD140a−). Panel E. Log 2-fold changes of significant genes for both genesets. Missing bars were not significant. Panel F. Heatmap of transformed transcripts per million (TPM) of selected genes in Panel E.
Figures 1E, 1F:
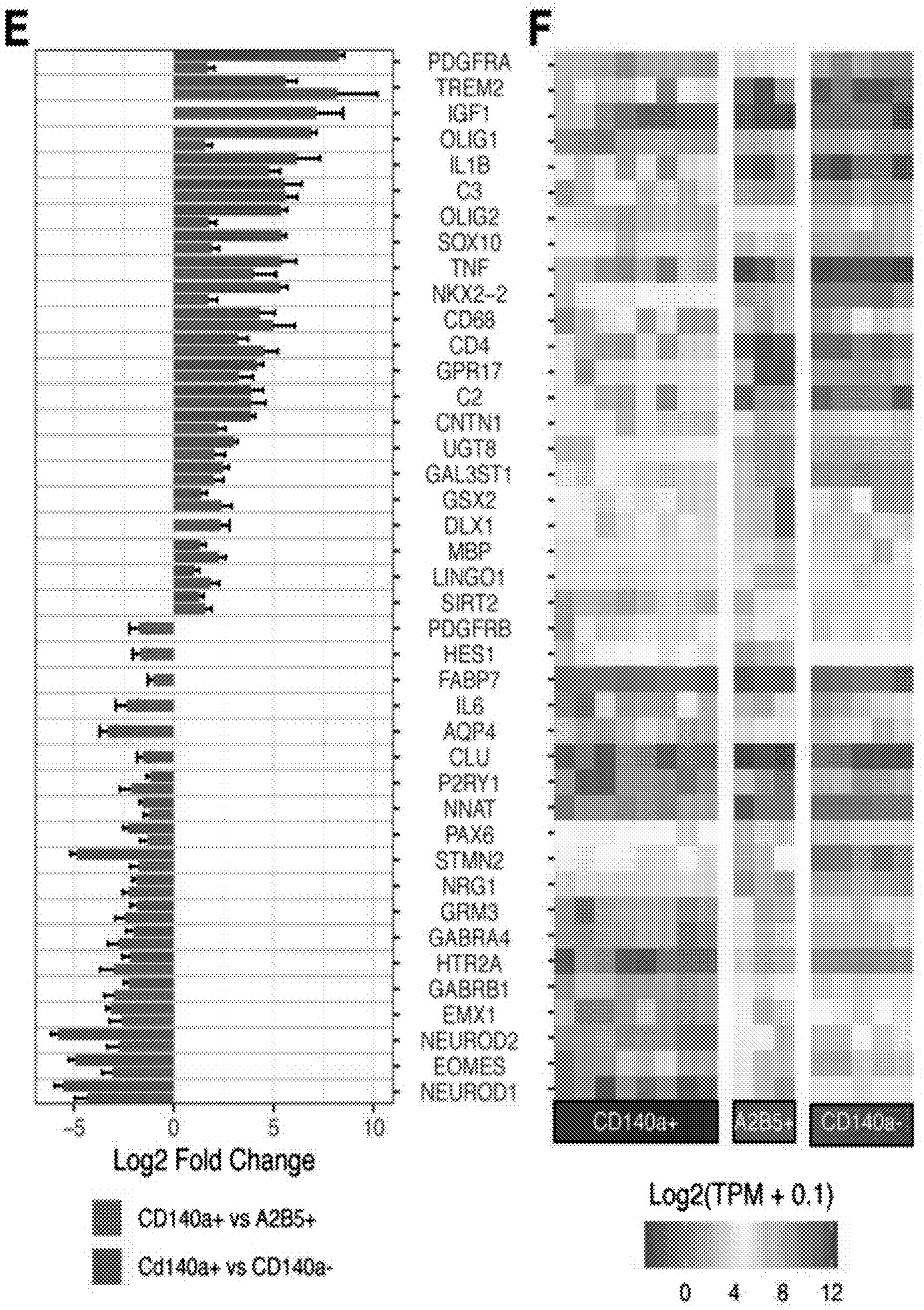

To identify the transcriptional concomitants to GPC aging, bulk and single cell RNA-Seq was first used to characterize hGPCs derived from second trimester fetal human tissue, whether isolated by targeting the CD140a epitope of PDGFRα (Sim et al., "CD140a Identifies a Population of Highly Myelinogenic, Migration-Competent and Efficiently Engrafting Human Oligodendrocyte Progenitor Cells," Nature Biotechnology 29:934-941 (2011a), which is hereby incorporated by reference in its entirety), or the glial gangliosides recognized by monoclonal antibody A2B5 (Dietrich et al., "Characterization of A2B5+ Glial Precursor Cells From Cryopreserved Human Fetal Brain Progenitor Cells," Glia 40:65-77 (2002); Sim et al., "CD140a Identifies a Population of Highly Myelinogenic, Migration-Competent and Efficiently Engrafting Human Oligodendrocyte Progenitor Cells," Nature Biotechnology 29:934-941 (2011a); and Windrem et al., "Fetal and Adult Human Oligodendrocyte Progenitor Cell Isolates Myelinate the Congenitally Dysmyelinated Brain," Nat. Med. 10:93-97 (2004), which are hereby incorporated by reference in their entirety). To that end, two sample-matched experiments were carried out whereby the ventricular/subventricular zones (VZ/SVZ) of 18-22-week gestational age (g.a.) fetal brains were dissociated and sorted via fluorescence activated cell sorting (FACS), for either CD140a+ and A2B5+/PSA-NCAM− (A2B5+) GPCs isolated from the same fetal brain (n=3), or for CD140a+GPCs as well as the CD140a-depleted remainder (n=5; FIG. 1, Panel A). Bulk RNA-Seq libraries were then generated and deeply sequenced for both experiments. Principal component analysis (PCA) showed segregation of the CD140a+ and A2B5+ cells, and further segregation of both from the CD140a-depleted samples (FIG. 1, Panel B). Differential expression in both paired cohorts (p<0.01, absolute log 2 fold change >1) identified 723 genes as differentially-expressed between CD140a+ and A2B5+ GPCs (435 in CD140a, 288 in A2B5, Table S1). In contrast, 2,629 genes distinguished CD140a+ GPCs from CD140a− cells (FIG. 1, Panel C). Differential gene expression directionality was highly consistent when comparing CD140+ to either A2B5+ or CD140-cells, with all but 4 genes being concordant.

Pathway enrichment analysis using Ingenuity Pathway Analysis (IPA) of both of these gene sets identified similar pathways as relatively active in CD140+ GPCs; these pathways included cell movement, oligodendroglial differentiation, lipid synthesis, and downstream PDGF, SOX10, and TCF7L2 signaling (FIG. 1, Panel D). As expected, stronger activation Z-scores were typically observed when comparing CD140a+ GPCs to CD140a− cells rather than to A2B5+ GPCs. Interestingly, CD140a+ cells also differentially expressed a number of pathways related to the immune system, likely due to small amounts of microglial contamination as a result of re-expression of PDGF□R epitopes on the microglial surface. A2B5+ samples additionally displayed upregulated ST8SIA1, the enzyme responsible for A2B5 synthesis (Sim et al., "Fate Determination of Adult Human Glial Progenitor Cells," Neuron Glia Biol 5:45-55 (2009), which is hereby incorporated by reference in its entirety), as well as pro-neural pathways.

Among the genes differentially upregulated in CD140a+ isolates were PDGFRA itself, and a number of early oligodendroglial genes including OLIG1, OLIG2, NKX2-2, SOX10, and GPR17 (FIGS. 1, Panel E-1, Panel F). Furthermore, the CD140a+ fraction also exhibited increased expression of later myelinogenesis-associated genes, including MBP, GAL3ST1, and UGT8. Beyond enrichment of the oligodendroglial lineage, many genes typically associated with microglia were also enriched in the CD140a isolates, including CD68, C2, C3, C4, and TREM2. In contrast, A2B5+ isolates exhibited enrichment of astrocytic (AQ4, CLU) and early neuronal (NEUROD1, NEUROD2, GABRG1, GABRA4, EOMES, HTR2A) genes, suggesting the expression of A2B5 by immature astrocytes and neurons as well as by GPCs and oligodendroglial lineage cells. Overall then, oligodendroglial enrichment was significantly greater in CD140a+GPCs than A2B5-defined GPCs, when each was compared to depleted fractions, suggesting the CD140a isolates as being the more enriched in hGPCs, and thus CD140a as the more appropriate phenotype for head-to-head comparison with adult hGPCs.

Figures 2A, 2B, 2C, 2D:
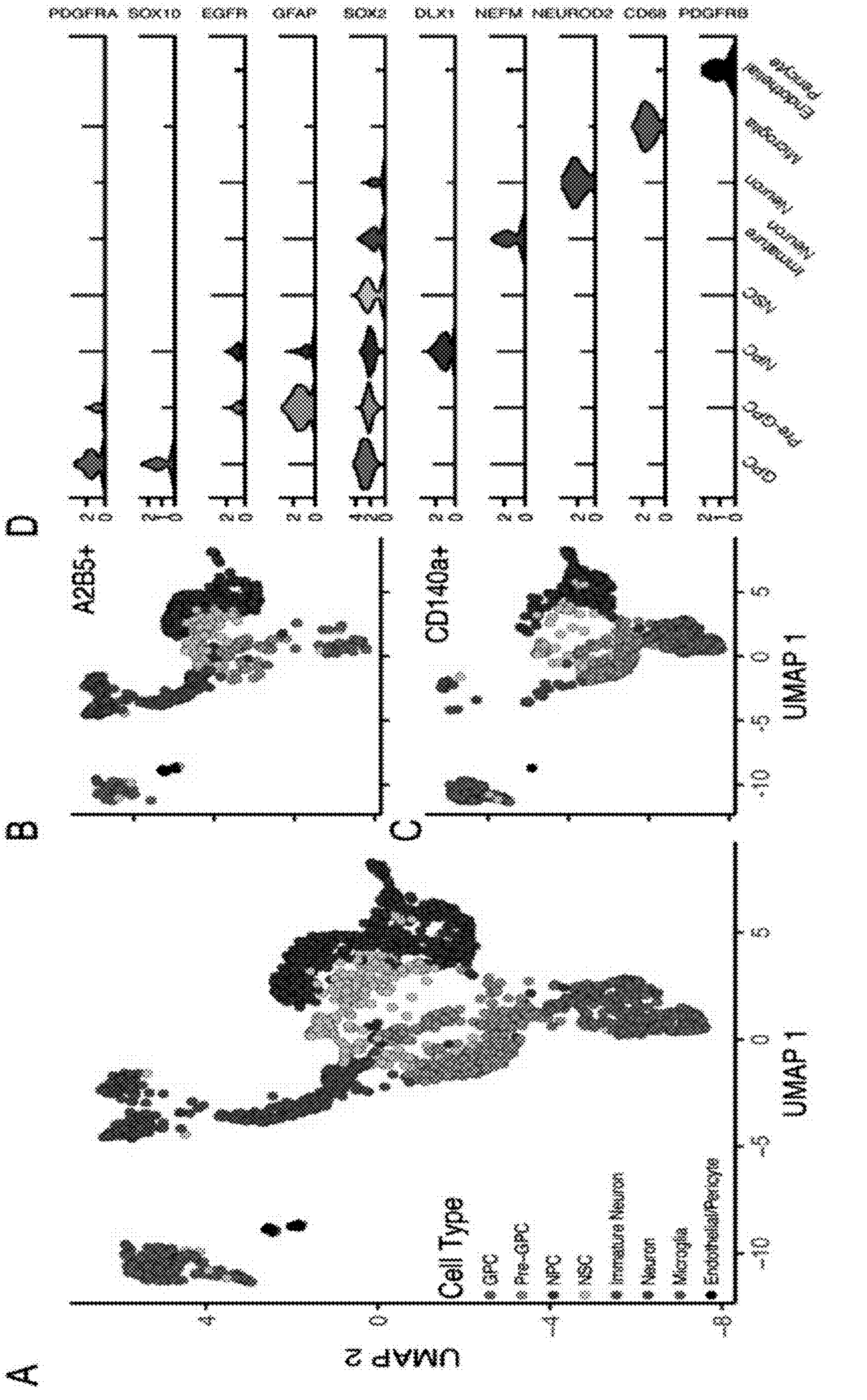
FIG. 2 shows single cell RNA-sequencing of CD140a and A2B5 selected human fetal GPCs. Panel A. UMAP plot of the primary cell types identified during scRNA-Seq analysis of FACS isolated hGPCs derived from 20 week gestational age human fetal VZ/SVZ. Panel B-Panel C. UMAP of only PSA−NCAM−/A2B5+ (B) or CD140a+ (C) human fetal cells. Panel D. Violin plots of cell type-selective marker genes. Panel E. Volcano plot of GPC vs pre-GPC populations. Panel F. Feature plots of select differentially expressed genes between GPCs and pre-GPCs. Panel G. Select significantly-enriched GPC and pre-GPC IPA terms, indicating their-log 10 p-value and activation Z-Score. Panel H. Select feature plots of transcription factors predicted to be significantly activated in fetal hGPCs. Relative transcription factor regulon activation is displayed as calculated using the SCENIC package.

Example 2: Single Cell RNA-Sequencing Reveals Cellular Heterogeneity within Human Fetal GPC Isolates To further delineate the composition of fetal hGPC isolates at single cell resolution, both CD140a+ and A2B5+ hGPCs were isolated from 20-week g.a. fetal VZ/SVZ via FACS, and then the transcriptomes of each were assayed by single cell RNA-Seq (FIG. 1, Panel A, 10× Genomics V2). It was sought to capture >1,000 cells of each; following filtration of low-quality cells (unique genes <500, mitochondrial gene percentage >15%), 1,053 PSA-NCAM−/A2B5+ and 957 CD140a+ high quality cells remained (median 6,845 unique molecular identifiers and 2,336 unique genes per cell). Dimensional reduction via uniform manifold approximation and projection (UMAP), followed by shared nearest neighbor modularity-based clustering of all cells using Seurat (Butler et al., "Integrating Single-cell Transcriptomic Data Across Different Conditions, Technologies, and Species," Nat Biotechnol 36:411-420 (2018), which is hereby incorporated by reference in its entirety), revealed 11 clusters with 8 primary cell types, as defined by their differential enrichment of marker genes. These primary cell types included: GPCs, pre-GPCs, neural progenitor cells (NPCs), immature neurons, neurons, microglia, and a cluster consisting of endothelial cells and pericytes. We found that the CD140a+FACS isolates were more enriched for GPC and pre-GPC populations than were the fetal A2B5+/PSA-NCAM− cells (FIGS. 2, Panel A-2, Panel D). Furthermore, whereas the CD140a− sorted cells were largely limited to GPCs and pre-GPCs, with only scattered microglial contamination, the A2B5+/PSA–NCAM– isolates also included astrocytes and neuronal lineage cells, the latter despite the upfront depletion of neuronal PSA–NCAM. These data supported the more selective and phenotypically-restricted nature of CD140a rather than A2B5-based GPC isolation.

On that basis, the gene expression profiles of the predominant cell populations in the CD140a+ fetal isolates, GPCs and pre-GPCs, was next explored. Differential expression between these two pools yielded 269 (143 upregulated, 126 down-regulated; $p<0.01$, log 2 fold change >0.5; FIG. 2, Panel E). During the pre-GPC to GPC transition, early oligodendroglial lineage genes were rapidly upregulated (OLIG2, SOX10, NKX2-2, PLLP, APOD), whereas those expressed in pre-GPCs effectively disappeared (VIM, HOPX, TAGLN2, TNC). Interestingly, genes involved in the human leukocyte antigen system, including HLA-A, HLA-B, HLA-C and B2M, were all downregulated as the cells transitioned to GPC stage (FIG. 2, Panel F). IPA analysis indicated that pre-GPCs were relatively enriched for terms related to migration, proliferation, and those presaging astrocytic identity (BMP4, AGT, and VEGF signaling), whereas GPCs displayed enrichment for terms associated with acquisition of an oligodendroglial identity (PDGF-AA, FGFR2, CCND1), in addition to activation of the MYC and MYCN pathways (FIG. 2, Panel G). Using single cell co-expression data together with promoter motif enrichment using the SCENIC package (Aibar et al., "SCENIC: Single-cell Regulatory Network Inference and Clustering," Nat Methods 14:1083-1086 (2017), which is hereby incorporated by reference in its entirety), 262 transcription factors that were predicted to be relatively activated in GPCs vs pre-GPCs were next identified (Wilcoxon rank sum test, $p<0.01$). These included SATB1, as well as the early GPC specification factors OLIG2, SOX10, and NKX2-2 (FIG. 2, Panel H).

Example 3: Human Adult and Fetal GPCs are Transcriptionally Distinct

The study next asked how adult hGPCs might differ in their transcription from fetal hGPCs. To this end, A2B5+ hGPCs were isolated from surgically-resected adult human temporal neocortex (19-21 years old, n=3) and their bulk RNA expression assessed, as paired together with four additional fetal CD140a+ samples. It had been previously noted that A2B5 selection is sufficient to isolate GPCs from adult human brain, and is more sensitive than CD140a in that regard, given the maturation-associated down-regulation of PDGFRA expression in adult hGPCs (Sim et al., "Complementary Patterns of Gene Expression by Human Oligodendrocyte Progenitors and their Environment Predict Determinants of Progenitor Maintenance and Differentiation," Ann Neurol 59:763-779 (2006) and Windrem et al., "Fetal and Adult Human Oligodendrocyte Progenitor Cell Isolates Myelinate the Congenitally Dysmyelinated Brain," Nat. Med. 10:93-97 (2004), which are hereby incorporated by reference in their entirety).

Confirming that prior observation, it was found that PDGFRA in A2B5+ adult GPCs was expressed with a median TPM of 0.55, compared to a median TPM of 47.56 for fetal A2B5+ cells. By pairing the sequencing and analysis with fetal CD140a-selected cells, regression of sequencing batch effects was enabled while simultaneously increasing power (FIG. 3, Panel A). Depletion of PSA-NCAM+ cells was not necessary for adult hGPC samples, as the expression of PSA-NCAM ceases in the adult cortex and white matter (Seki et al., "Distribution and Possible Roles of the Highly Polysialylated Neural Cell Adhesion Molecule (NCAM-H) in the Developing and Adult Central Nervous System," Neurosci. Res. 1:265-290 (1993), which is hereby incorporated by reference in its entirety). As a result, PCA of human adult and fetal GPCs illustrated tight clustering of adult GPCs, sharply segregated from both sorted fetal hGPC pools (FIG. 3, Panel B). Differential expression of adult GPCs compared to either A2B5+ or CD140a+ fetal GPC populations yielded 3,142 and 5,282 significant genes, respectively ($p<0.01$; absolute log 2 fold-change >1) (FIG. 3, Panel C). To increase the accuracy of defining differential expression, downstream analyses were carried out on the intersecting 2,720 genes (FIG. 3, Panel D, 1,060 up-regulated and 1,660 down-regulated in adult GPCs, compared to fetal hGPCs). Remarkably, within these two differentially-expressed gene sets, 100% of genes were directionally concordant.

Figures 3D, 3E:
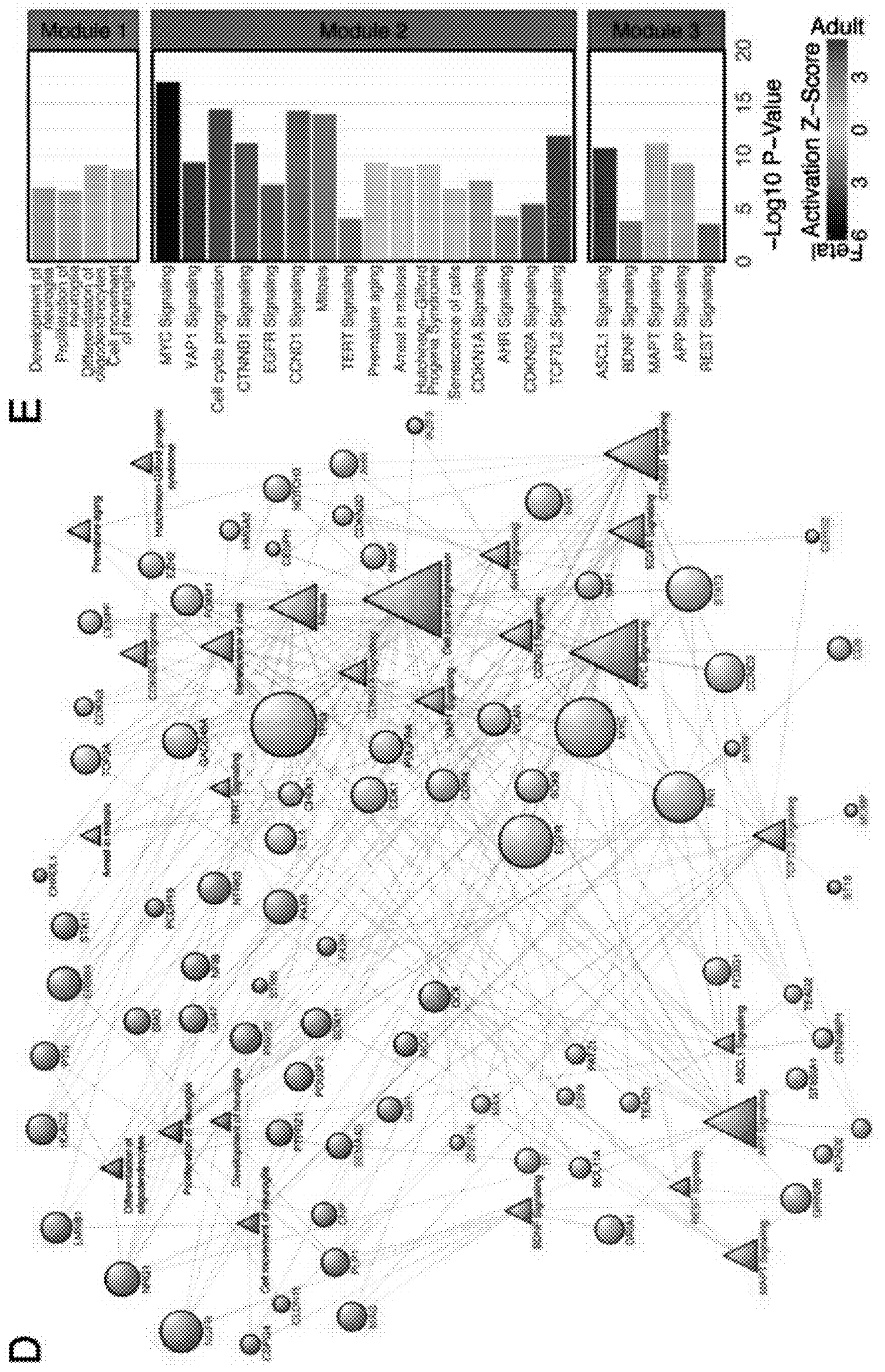
FIG. 3 shows adult human GPCs are transcriptionally and functionally distinct from fetal GPCs. Panel A. Workflow of bulk RNA-Seq analysis of human adult and fetal GPCs. Panel B. Principal component analysis of all samples across three batches. Panel C. Venn Diagram of both Adult vs Fetal differential expression gene sets. Panel D. IPA network of curated terms and genes. Node size is proportionate to node degree. Label color corresponds to enrichment in either adult (red) or fetal (blue) populations. Panel E. Bar plots of significant IPA terms by module. Z-Scores indicate predicted activation in fetal (blue) or adult (red) hGPCs. Panel F. Bar plot of log 2-fold changes and heatmap of network genes' TPM.
Figure 3F:
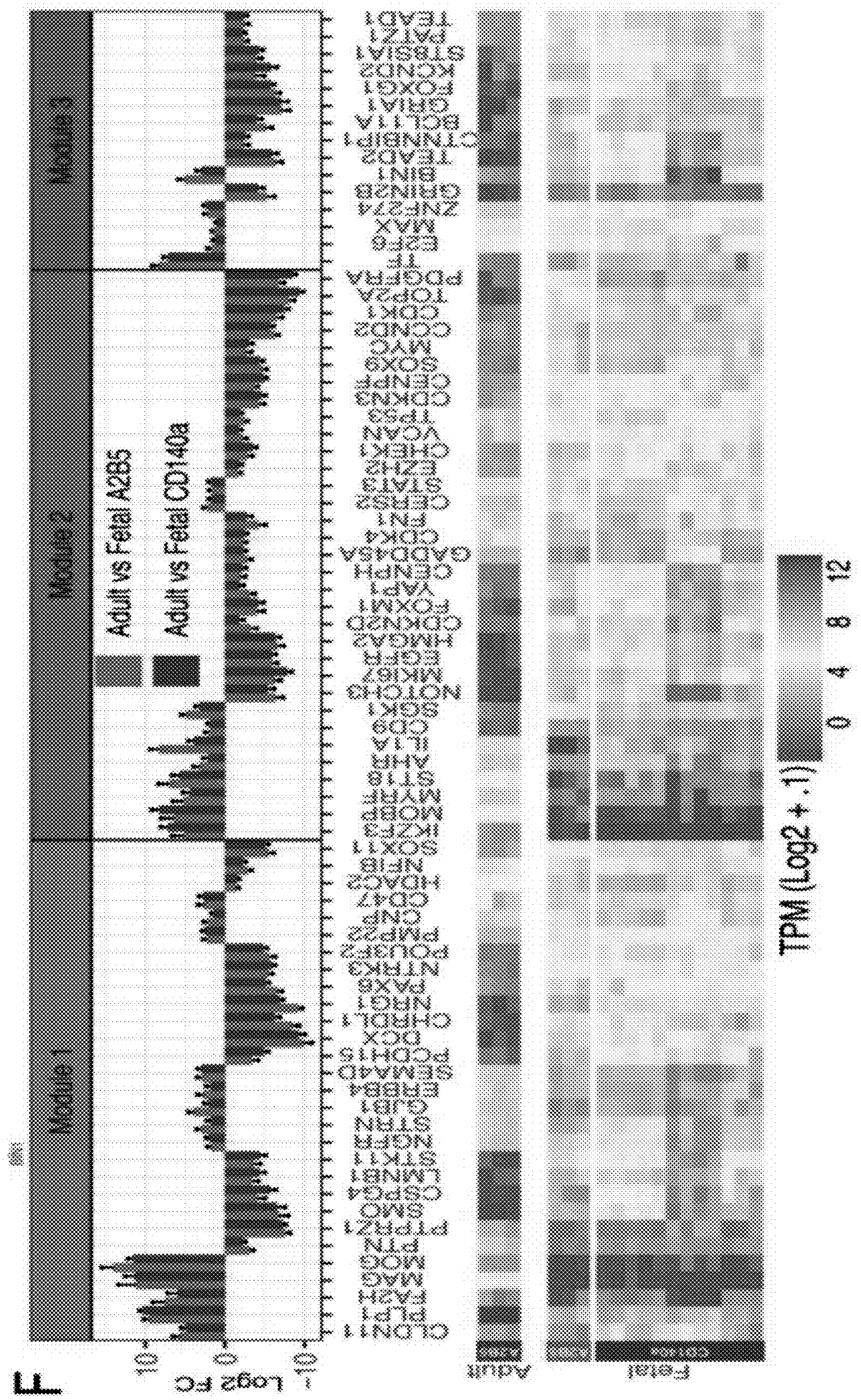

To better understand the differences between adult and fetal GPCs, a gene ontology network of non-redundant significant IPA terms and their contributing differentially-expressed genes was constructed (FIGS. 3, Panel D-3, Panel E). Spin glass community detection of this network (Reichardt et al., "Statistical Mechanics of Community Detection," Phys. Rev. E Stat. Nonlin. Soft Matter Phys. 74:016110 (2006), which is hereby incorporated in its entirety) uncovered three modules (Modules M1-M3) of highly connected functional terms (FIG. 3E) and genes (FIG. 3F, Table S3). M1 included terms and genes linked to glial development, proliferation, and movement. Notably, a number of genes associated with GPC ontogeny were downregulated in adult GPCs; these included CSPG4/NG2, PCDH15, CHRDL1, LMNB1, PTPRZ1, and ST8SIA1 (Huang et al., "Origins and Proliferative States of Human Oligodendrocyte Precursor Cells," Cell 182:594-608 e511 (2020); McClain et al., "Pleiotrophin Suppression of Receptor Protein Tyrosine Phosphatase-β/ζ Maintains the Self-renewal Competence of Fetal Human Oligodendrocyte Progenitor Cells," J Neurosci 32:15066-15075 (2012); Nishiyama et al., "Co-Localization of NG2 Proteoglycan and PDGF α-Receptor on O2A Progenitor Cells in the Developing Rat Brain," Journal of Neuroscience Research 43:299-314 (1996); Sim et al., "Fate Determination of Adult Human Glial Progenitor Cells," Neuron Glia Biol 5:45-55 (2009); and Yattah et al., "Dynamic Lamin B1-Gene Association During Oligodendrocyte Progenitor Differentiation," Neurochem Res 45:606-619 (2020), which are hereby incorporated by reference in their entirety). In contrast, numerous genes whose appearance precedes and continues through oligodendrocyte differentiation and myelination were upregulated in adult GPCs, including MAG, MOG, MYRF, PLP1, CD9, CLDN11, CNP, ERBB4, GJB1, PMP22, and SEMA4D.

Module 2 harbored numerous terms associated with cellular aging and the modulation of proliferation and senescence. Cell cycle progression and mitosis were predicted to be activated in fetal GPCs due to strong enrichment of proliferative factors including MKI67, TOP2A, CENPF, CENPH, CHEK1, EZH2 and numerous cyclins, including CDK1 and CDK4. Furthermore, proliferation-inducing pathways were also inferred to be activated; these included MYC, CCND1, and YAP1 signaling, of which both YAP1 and MYC transcripts were similarly upregulated (Bretones et al., "Myc and Cell Cycle Control," Biochim. Biophys Acta 1849:506-516 (2015); Bunt et al., "Regulation of Cell Cycle Genes and Induction of Senescence by Overexpression of OTX2 in Medulloblastoma Cell Lines," Mol. Cancer Res. 8:1344-1357 (2010); and Xie et al., "YAP/TEAD-Mediated Transcription Controls Cellular Senescence,"

Cancer Res 73:3615-3624 (2013), which are hereby incorporated by reference in their entirety). In that regard, transient overexpression of MYC in aged rodent GPCs has recently been shown to restore their capacity to both proliferate and differentiate (Neumann et al., "Myc Determines the Functional Age State of Oligodendrocyte Progenitor Cells," Nature Aging 1:826-837 (2021), which is hereby incorporated by reference in its entirety). Conversely, adult GPCs exhibited an upregulation of senescence-associated transcripts, including E2F6, MAP3K7, DMTF1/DMP1, OGT, AHR, RUNX1, and RUNX2 (Ferrand et al., "Screening of a Kinase Library Reveals Novel Pro-senescence Kinases and Their Common NF-κB-dependent Transcriptional Program," Aging (Albany NY) 7:986-1003 (2015); Inoue et al., "Disruption of the ARF Transcriptional Activator DMP1 Facilitates Cell Immortalization, Ras Transformation, and Tumorigenesis," Genes Dev 14:1797-1809 (2000); Lee and Zhang, "O-Linked N-Acetylglucosamine Transferase (OGT) Interacts With the Histone Chaperone HIRA Complex and Regulates Nucleosome Assembly and Cellular Senescence," Proceedings of the National Academy of Sciences 113: E3213-E3220 (2016); Wotton et al., "RUNX1 Transformation of Primary Embryonic Fibroblasts is Revealed in the Absence of p53," Oncogene 23:5476-5486 (2004); and Kilbey et al., "Runx2 Disruption Promotes Immortalization and Confers Resistance to Oncogene-induced Senescence in Primary Murine Fibroblasts," Cancer Res 67:11263-11271 (2007), which are hereby incorporated by reference in their entirety). At the same time, adult hGPCs exhibited a down-regulation of fetal transcripts that included LMNB1, PATZ1, BCL11A, HDAC2, FN1, EZH2, and YAP1 and its cofactor TEAD1 (Cho et al., "POZ/BTB and AT-hook-containing Zinc Finger Protein 1 (PATZ1) Inhibits Endothelial Cell Senescence Through a p53 Dependent Pathway," Cell Death Differ 19:703-712 (2012); Fan et al., "EZH2-dependent Suppression of a Cellular Senescence Phenotype in Melanoma Cells by Inhibition of p21/CDKN1A Expression," Mol. Cancer Res. 9:418-429 (2011); Freund et al., "Lamin B1 Loss is a Senescence-associated Biomarker," Mol. Biol. Cell 23:2066-2075 (2012); Luc et al., "Bcl11a Deficiency Leads to Hematopoietic Stem Cell Defects with an Aging-like Phenotype," Cell Rep. 16:3181-3194 (2016); Lukjanenko et al., "Loss of Fibronectin From the Aged Stem Cell Niche Affects the Regenerative Capacity of Skeletal Muscle in Mice," Nat Med 22:897-905 (2016); Sundar et al., "Genetic Ablation of Histone Deacetylase 2 Leads to Lung Cellular Senescence and Lymphoid Follicle Formation in COPD/Emphysema," FASEB Journal: Official Publication of the Federation of American Societies for Experimental Biology 32:4955-4971 (2018); and Xie et al., "YAP/TEAD-Mediated Transcription Controls Cellular Senescence," Cancer Res 73:3615-3624 (2013), which are hereby incorporated by reference in their entirety). As a result, functional terms predicted to be active in adult hGPCs included senescence, the rapid onset of aging observed in Hutchinson-Gilford progeria, and cyclin-dependent kinase inhibitory pathways downstream of CDKN1A/p21 and CDKN2A/p16. Furthermore, AHR and its signaling pathway, which has been implicated in driving senescence via the inhibition of MYC (Yang et al., "The Aryl Hydrocarbon Receptor Constitutively Represses C-Myc Transcription in Human Mammary Tumor Cells," Oncogene 24:7869-7881 (2005), which is hereby incorporated by reference in its entirety), was similarly upregulated in adult GPCs.

Module 3 consisted primarily of developmental and disease linked signaling pathways that have also been associated with aging. This included the predicted activation of ASCL1 and BDNF signaling in fetal hGPCs and MAPT/Tau, APP, and REST signaling in adult GPCs (Ahlin et al., "High Expression of Cyclin D1 is Associated to High Proliferation Rate and Increased Risk of Mortality in Women With ER-positive But Not in ER-negative Breast Cancers," Breast Cancer Res. Treat 164:667-678 (2017); Erickson et al., "Brain-derived Neurotrophic Factor is Associated With Age-related Decline in Hippocampal Volume," J. Neurosci. 30:5368-5375 (2010); and Harris et al., "Coordinated Changes in Cellular Behavior Ensure the Lifelong Maintenance of the Hippocampal Stem Cell Population," Cell Stem Cell (2021), which are hereby incorporated by reference in their entirety). Overall, the transcriptional and functional profiling of adult GPCs revealed a reduction in transcripts associated with proliferative capacity, and a shift toward senescence and more mature phenotype.

Example 4: Inference of Transcription Factor Activity Implicates Adult GPC Transcriptional Repressors Given the significant transcriptional disparity between adult and fetal GPCs, the study next asked whether it could infer which transcription factors direct their identities. To accomplish this, two promoter windows (500 bp up/100 bp down, 10 kb up/10 kb down) of adult or fetal enriched GPC gene sets were first scanned to infer significantly enriched TF motifs (Aibar et al., "SCENIC: Single-cell Regulatory Network Inference and Clustering," Nat. Methods 14:1083-1086 (2017), which is hereby incorporated by reference in its entirety). This identified 48 TFs that were also differentially-expressed in the scanned intersecting dataset. Among these, TFs whose primary means of DNA interaction were exclusively either repressive or stimulatory, were first investigated, while also considering the enrichment of their known cofactors. This analysis yielded 12 potential upstream regulators to explore (FIGS. 4, Panel A-4, Panel C): 4 adult repressors, E2F6, ZNF274, MAX, and IKZF3; 1 adult activator, STAT3; 3 fetal repressors, BCL11A HDAC2, and EZH2; and 4 fetal activators, MYC, HMGA2, NFIB, and TEAD2. Interestingly, of these predicted TFs, 3 groups shared a high concordance of motif similarity within their targeted promoters: 1) E2F6, ZNF274, MAX, and MYC; 2) STAT3 and BCL11A; and 3) EZH2 and HDAC2, suggesting that they may cooperate or compete for DNA binding at shared loci (FIG. 4, Panel A).

Figures 4D, 4E:
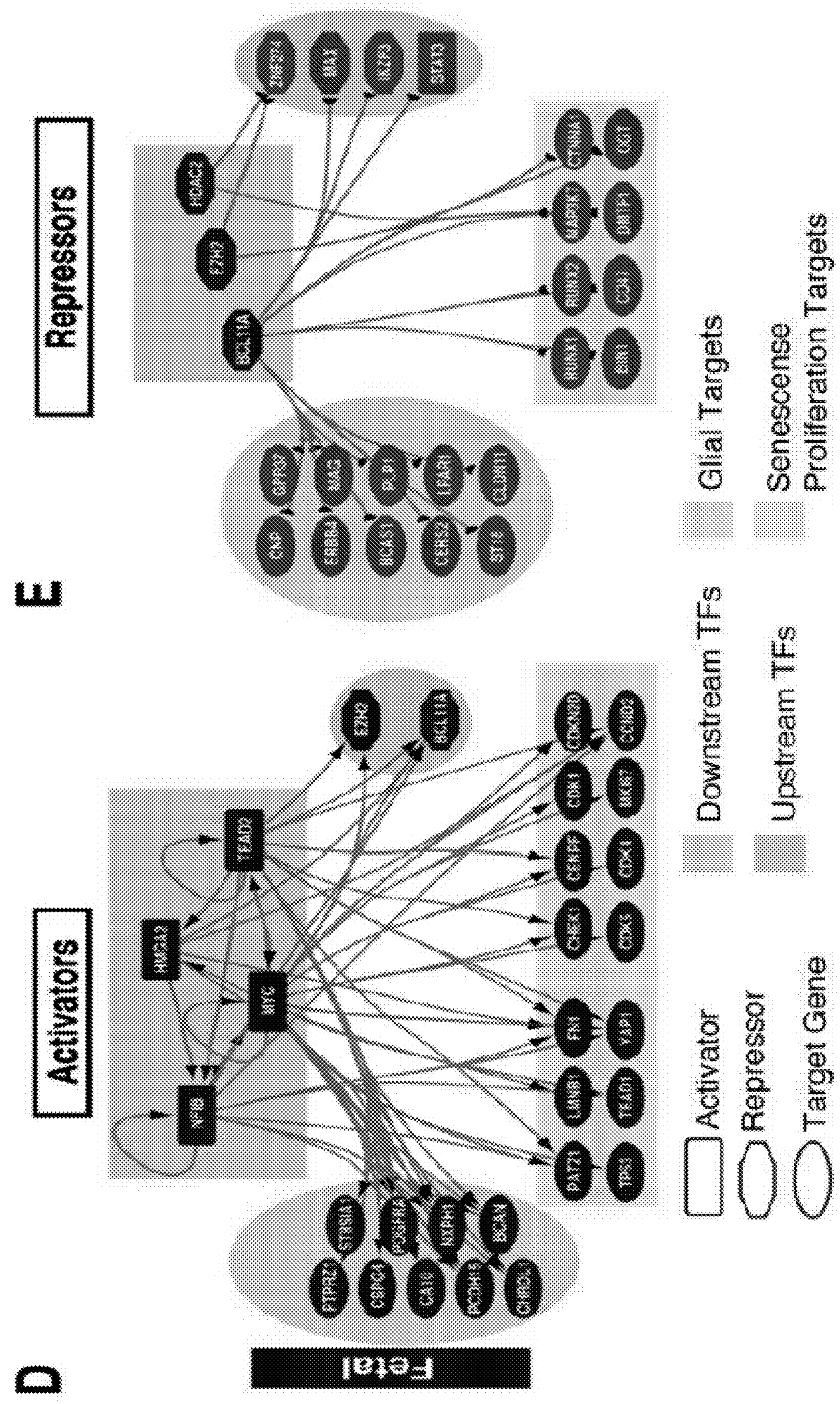
FIG. 4 shows inference of transcription factor activity implicates a set of transcriptional repressors in the establishment of adult hGPC identity. Panel A. Normalized enrichment score plots of significantly enriched transcription factors predicted to be active in fetal and adult GPCs. Each dot is a motif whose size indicates how many genes in which that motif is predicted to be active, and the color represents the window around the promoter at which that motif was found enriched. Panel B. Heatmap of enriched TF TPMs, and C, log-fold changes vs adult GPCs, for both fetal hGPC isolates. Panel D-Panel G. Predicted direct transcription factor activity of curated genes split into D fetal activators; Panel E, fetal repressors; Panel F, adult activators; and Panel G, adult repressors. Color indicates differential expression in either adult (red) or fetal (blue) hGPCs; shape dictates type of node (octagon, repressor; rectangle, activator; oval, other target gene). Boxed and circled genes indicate functionally-related genes contributing to either glial progenitor/oligodendrocyte identity, senescence/proliferation targets, or upstream or downstream TFs that were also deemed activated.
Figures 4F, 4G:
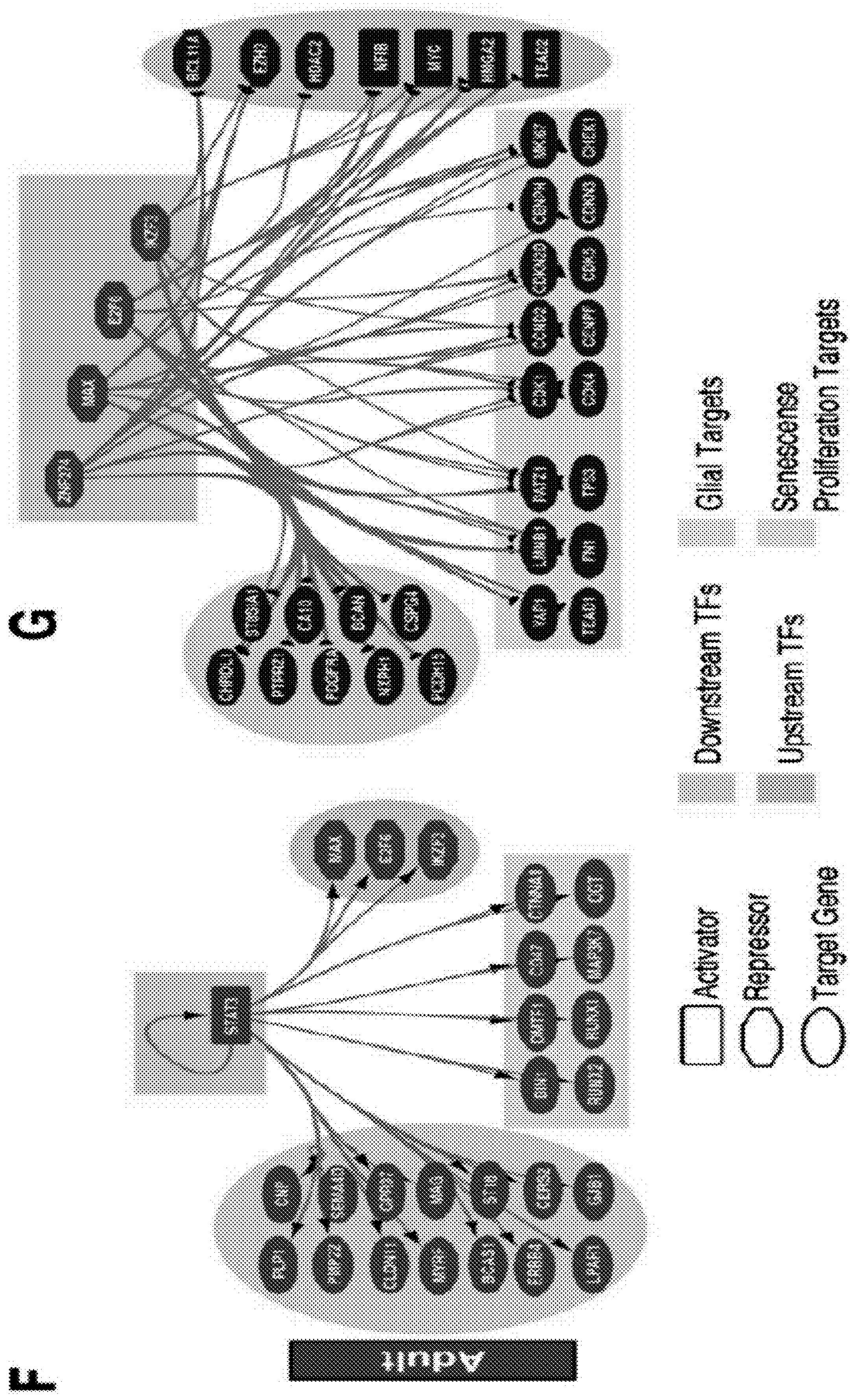

Next, four potential signaling pathways were constructed based on curated transcriptional interactions, to predict those genes targeted by the set of identified TFs (FIGS. 4, Panel D-4, Panel G). Among activators enriched in fetal GPCs (FIG. 4, Panel D), MYC, a proliferative factor (Dang, C. V., "c-Myc Target Genes Involved in Cell Growth, Apoptosis, and Metabolism," Molecular and Cellular Biology 19:1 (1999), which is hereby incorporated by reference in its entirety), NFIB, a key determinant of gliogenesis (Deneen et al., "The Transcription Factor NFIA Controls the Onset of Gliogenesis in the Developing Spinal Cord," Neuron 52:953-968 (2006), which is hereby incorporated by reference in its entirety), TEAD2, a YAP/TAZ effector, and HMGA2, another proliferative factor, were each predicted to activate cohorts of progenitor stage genes, including both mitogenesis-associated transcripts and those demonstrated to inhibit the onset of senescence (Dang, C. V., "c-Myc Target Genes Involved in Cell Growth, Apoptosis, and Metabolism," Molecular and Cellular Biology 19:1 (1999); Deneen et al., "The Transcription Factor NFIA Controls the Onset of Gliogenesis in the Developing Spinal Cord," Neuron 52:953-968 (2006); Diepenbruck et al., "Tead2 Expression Levels Control the Subcellular Distribution of Yap and Taz, Zyxin Expression and Epithelial-mesenchymal Transition," Journal of Cell Science 127:1523-1536 (2014); and Yu et al., "HMGA2 Regulates the in Vitro Aging and Proliferation of Human Umbilical Cord Blood-Derived Stromal Cells Through the mTOR/p70S6K Signaling Pathway," Stem Cell Res 10:156-165 (2013), which are hereby incorporated by reference in their entirety). Direct positive regulation was also predicted between these four fetal activators, with NFIB being driven by HMGA2 and TEAD2, MYC being driven by TEAD2 and NFIB, HMGA2 being driven by MYC and TEAD2, and TEAD2 being reciprocally driven by MYC (FIG. 4, Panel D). In contrast to these fetal activators, fetal stage repressors, including the C2H2 type zinc finger BCL11A, the polycomb repressive complex subunit EZH2, and histone deacetylase HDAC2, were each predicted to repress more mature oligodendrocytic gene expression at this stage (FIG. 4, Panel E) (Laherty et al., "Histone Deacetylases Associated With the mSin3 Corepressor Mediate Mad Transcriptional Repression," Cell 89:349-356 (1997); Laible et al., "Mammalian Homologues of the Polycomb-group Gene Enhancer of Zeste Mediate Gene Silencing in Drosophila Heterochromatin and at *S. cerevisiae* Telomeres," EMBO J 16:3219-3232 (1997); and Nakamura et al., "Evi9 Encodes a Novel Zinc Finger Protein that Physically Interacts with BCL6, a known Human B-Cell Proto-Oncogene Product," Mol Cell Biol 20:3178-3186 (2000), which are hereby incorporated by reference in their entirety). Furthermore, all three of these TFs were predicted to inhibit targets implicated in senescence. As such, these factors appear to directly orchestrate downstream transcriptional events leading to maintenance of the cycling progenitor state.

Next, these predicted adult GPC signaling networks were assessed for a potential mechanism responsible for their age-related gene expression changes. STAT3 was predicted to shift GPC identity towards glial maturation via the upregulation of a large cohort of early differentiation- and myelination-associated oligodendrocytic genes (FIG. 4, Panel F). In addition, STAT3 was also inferred to activate a set of senescence-associated genes including BIN1, RUNX1, RUNX2, DMTF1, CD47, MAP3K7, CTNNA1, and OGT. At the same time, repression in adult GPCs was predicted to be effected through the Ikaros family zinc finger IKZF3/Aiolos, the KRAB (kruppel associated box) zinc finger ZNF274, the MYC-associated factor MAX, and cell cycle regulator E2F6 (FIG. 4, Panel G) (Blackwood and Eisenman, "Max: A Helix-loop-helix Zipper Protein That Forms a Sequence-specific DNA-binding Complex With Myc," Science 251:1211-1217 (1991); Frietze et al., "ZNF274 Recruits the Histone Methyltransferase SETDB1 to the 3' Ends of ZNF Genes," PLOS One 5: e15082 (2010); Ma et al., "Ikaros and Aiolos Inhibit Pre-B-cell Proliferation by Directly Suppressing c-Myc Expression," Mol Cell Biol 30:4149-4158 (2010b); and Ogawa et al., "A Complex with Chromatin Modifiers that Occupies E2F- and Myc-Responsive Genes in G0 Cells," Science 296:1132-1136 (2002), which are hereby incorporated by reference in their entirety). Targeting by this set of transcription factors predicted repression of those gene sets contributing to the fetal GPC signature, and this was indeed observed in the down-regulation of the early progenitor genes PDGFRA and CSPG4, as well as of the cell cyclicity genes CDK1, CDK4, and MKI67. Repression of YAP1, LMNB1, and TEAD1, whose expression slows or prevents the onset of senescence, was also predicted. Interestingly, this set of four adult repressors predicted the down-regulated expression of each of the fetal enriched activators NFIB, MYC, TEAD2, and HMGA2, in addition to the fetal enriched repressors BCL11A, EZH2, and HDAC2.

Figures 5A, 5B:
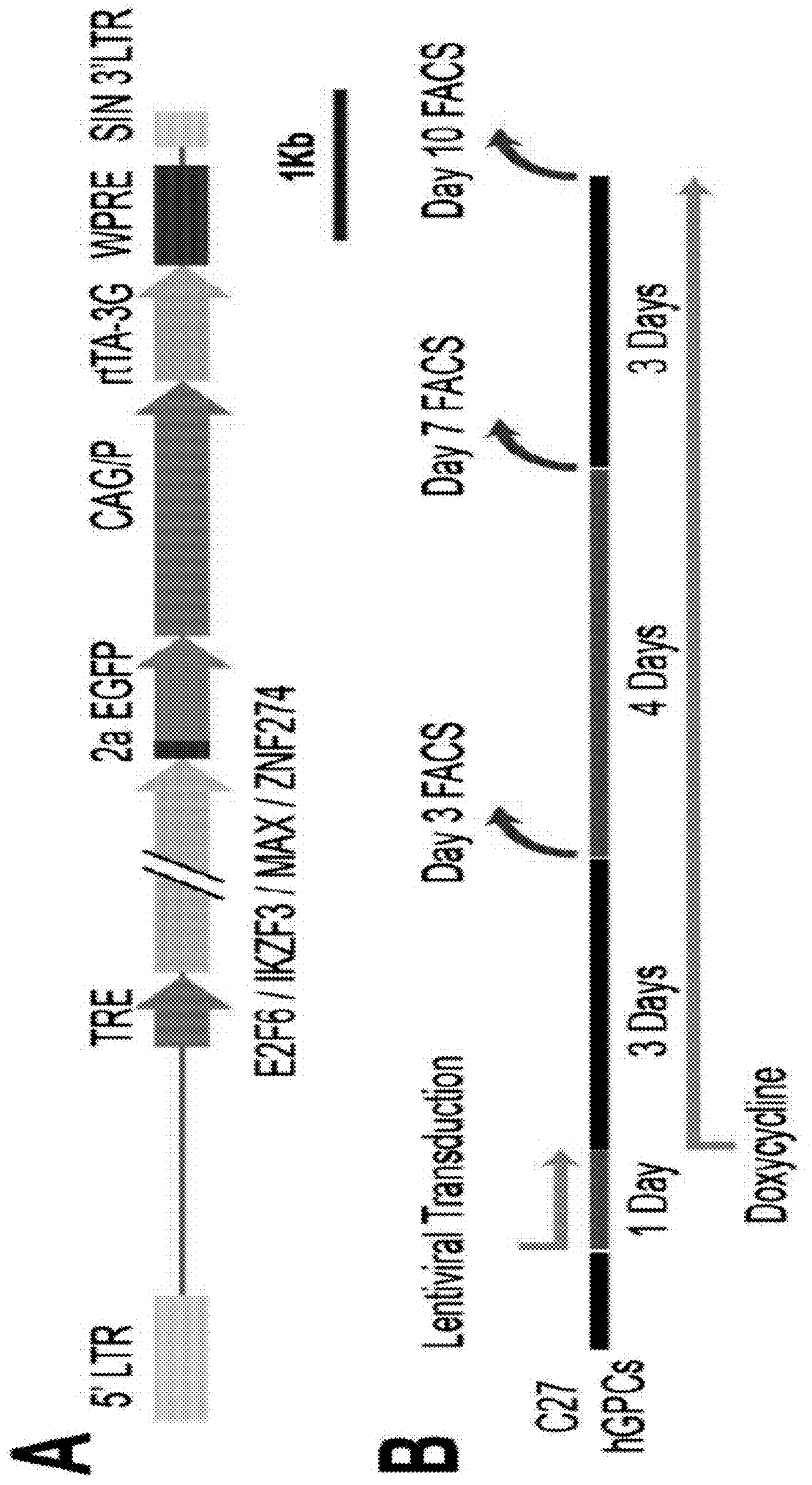
FIG. 5 shows induction of an aged GPC transcriptome via adult hGPC-enriched repressors. Panel A. Schematic outlining the structure of four distinct doxycycline (Dox)-inducible EGFP lentiviral expression vectors, each encoding one of the transcriptional repressors: E2F6, IKZF3, MAX, or ZNF274. Panel B. Induced pluripotent stem cell (iPSC)-derived hGPC cultures (line C27 (Chambers et al., Nature biotechnology, 27, 275-280, 2009; Wang et al., Cell Stem Cell 12, 252-264, 2013)) were transduced with a single lentivirus or vehicle for one day, and then treated with Dox for the remainder of the experiment. At 3, 7, and 10 days following initiation of Dox-induced transgene expression, hGPCs were isolated via FACS for qPCR. Panel C. qPCRs of Dox-treated cells showing expression of each transcription factor, vs matched timepoint controls. Panel D. qPCR fold-change heatmap of select aging related genes. Within timepoint comparisons to controls were calculated via post hoc least-squares means tests of linear models following regression of a cell batch effect. FDR adjusted p-values: *<0.05, <0.01, *<0.001.
Figures 5C, 5D:
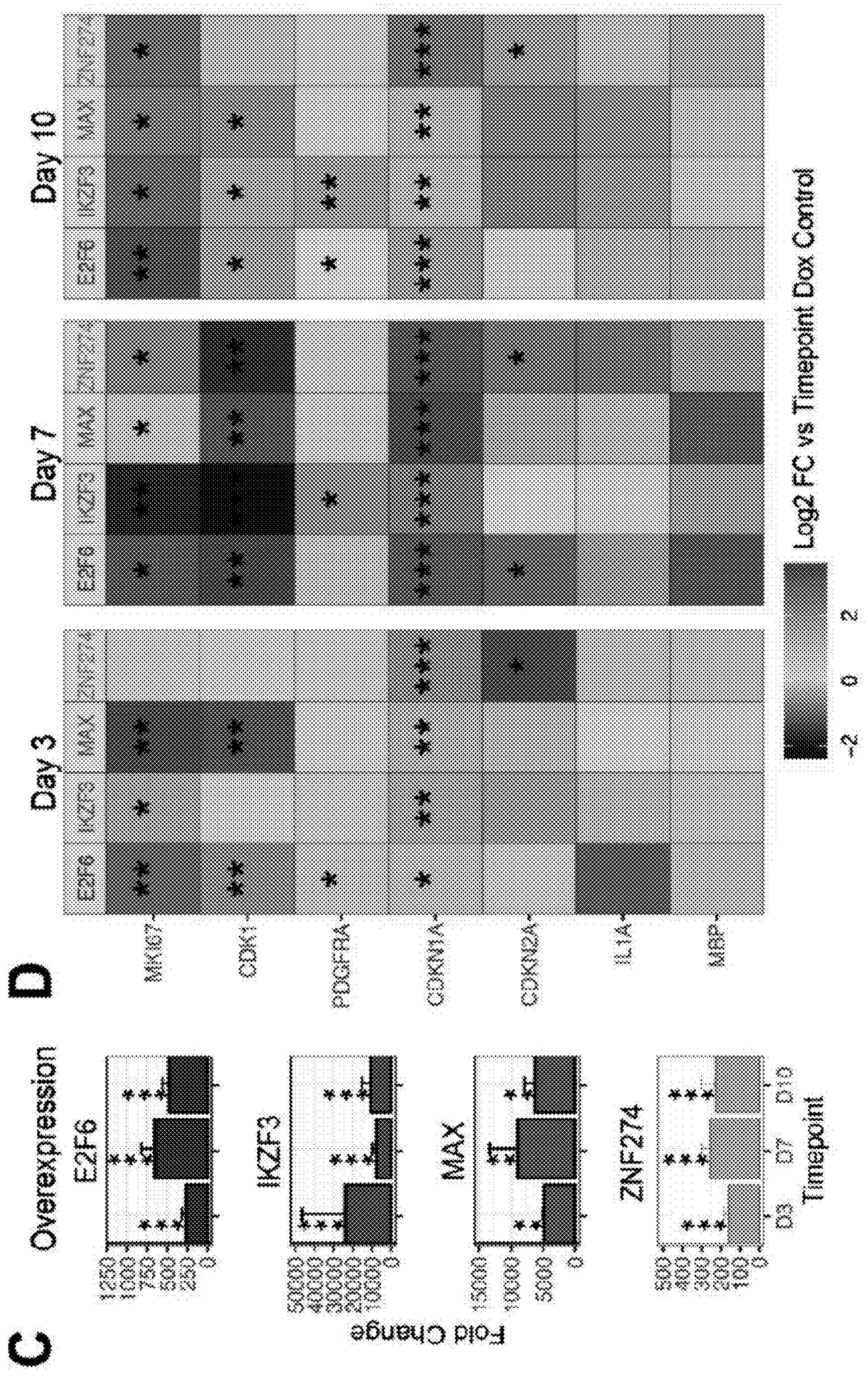

Example 5: Expression of Adult-Enriched Repressors Induces Age-Associated Transcriptional Changes in GPCs It was next asked whether the four adult-enriched transcriptional repressors identified in FIG. 4, Panel G, E2F6, IKZF3, MAX, and ZNF274, were individually sufficient to induce aspects of the age-associated changes in gene expression by otherwise young GPCs. To accomplish this, doxycycline (Dox) inducible overexpression lentiviruses were designed for each transcription factor (FIG. 5, Panel A). Briefly, which protein-coding isoform was most abundant in adult GPCs for each repressor was first identified, so as to best mimic endogenous age-associated upregulation; these candidates were E2F6-202, IKZF3-217, MAX-201, and ZNF274-201. These cDNAs were cloned downstream of a tetracycline response element promoter, and upstream of a T2A self-cleaving EGFP reporter (FIG. 5, Panel A). Human induced pluripotent stem cell (iPSC)-derived hGPC cultures, prepared from the C27 line as previously described (Wang et al., "Human iPSC-Derived Oligodendrocyte Progenitor Cells Can Myelinate and Rescue a Mouse Model of Congenital Hypomyelination," Cell Stem Cell 12:252-264 (2013), which is hereby incorporated by reference in its entirety), were then infected for 24 hours, and then treated with Dox to induce transgene overexpression. C27 iPSC-derived GPCs were chosen as their transcriptome resembles that of fetal, and they are similarly capable of engrafting and myelinating dysmyelinated mice upon transplantation (Wang et al., "Human iPSC-Derived Oligodendrocyte Progenitor Cells Can Myelinate and Rescue a Mouse Model of Congenital Hypomyelination," Cell Stem Cell 12:252-264 (2013) and Windrem et al., "Human iPSC Glial Mouse Chimeras Reveal Glial Contributions to Schizophrenia," Cell Stem Cell 21:195-208.e196 (2017), which are hereby incorporated by reference in their entirety). Over-expressing cells were selected via FACS for EGFP expression, at 3, 7, and 10 days following Dox addition (FIG. 5, Panel B, n=3-5). Uninfected cultures given Dox were used as controls.

RNA was extracted and aging-associated genes of interest were analyzed by qPCR. Significant induction of each adult-enriched repressor was observed at each timepoint following Dox supplementation (FIG. 5, Panel C). MKI67 and CDK1, genes whose upregulation are associated with active cell division, were significantly repressed at two or more timepoints in each over-expression paradigm (FIG. 5, Panel D). This was consistent with their diminished expression in adult GPCs (FIG. 3, Panel F), and suggested their direct repression by E2F6, MAX, and ZNF274 (MKI67), or by all four (CDK1). The GPC stage marker PDGFRA, the cognate receptor for PDGF-AA, was also significantly repressed at two timepoints in the IKZF3-transduced GPCs, as well as in the E2F6-transduced GPCs at day 3, consistent with its repression in normal adult GPCs. Interestingly, the senescence-associated cyclin-dependent kinase inhibitor CDKN1A/p21 was upregulated in response to each of the tested repressors at all timepoints, while CDKN2A/p16 was similarly upregulated in at all timepoints in ZNF274-transduced hGPCs, as well as in the E2F6-over-expressing GPCs at day 7 (FIG. 5, Panel D). In addition, MBP and ILIA, both of which are strongly upregulated in adult hGPCs relative to fetal, both exhibited sharp trends towards upregulated expression in response to repressor transduction, although timepoint-associated variability prevented their increments from achieving statistical significance. Together, these data supported our prediction that forced, premature expression of the adult-enriched GPC repressors, E2F6, IKZF3, MAX, and ZNF274, are individually sufficient to induce multiple features of the aged GPC transcriptome in young, iPSC-derived GPCs.

Figure 6D:
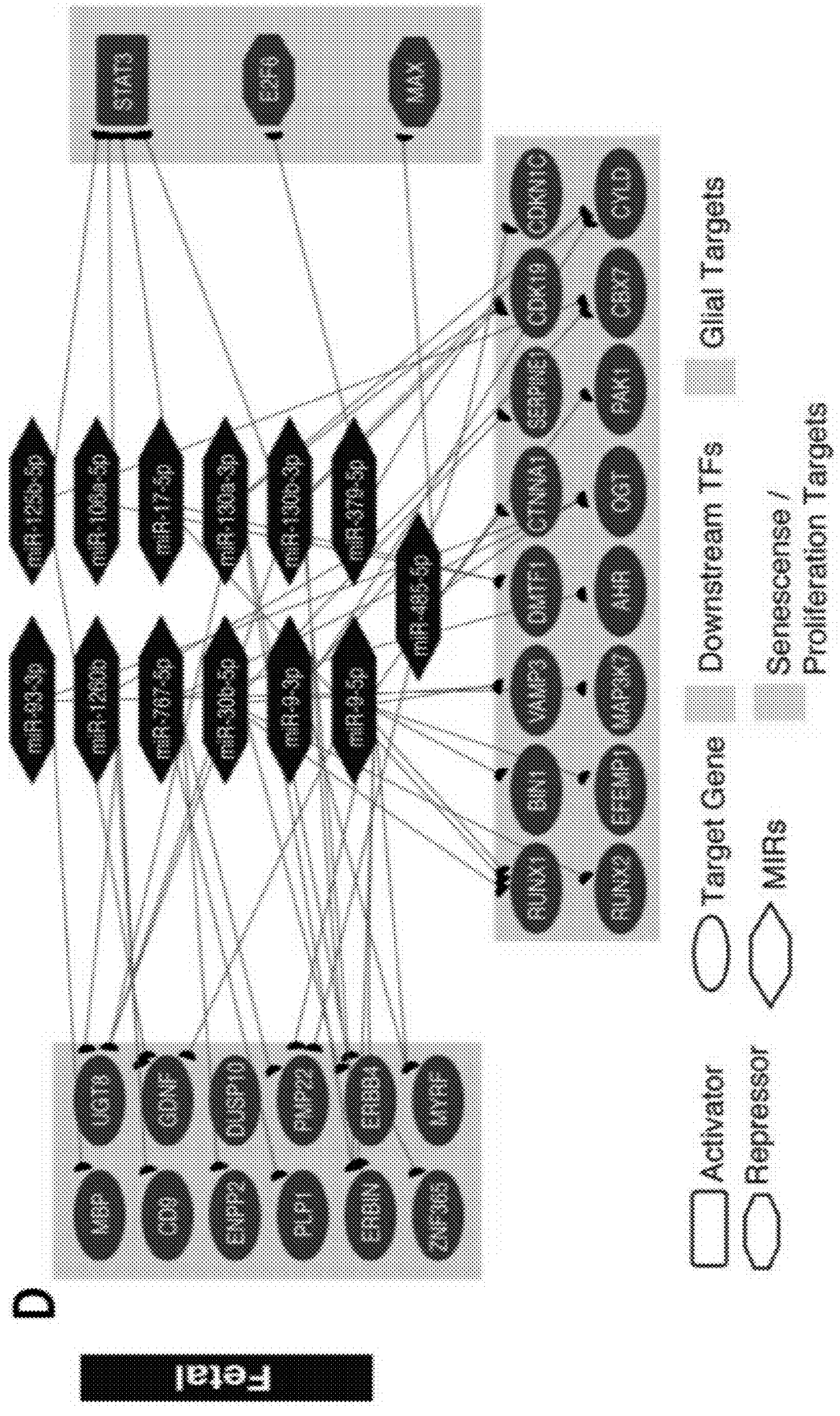
FIG. 6 shows miRNAs drive adult GPC transcriptional divergence in parallel to transcription factor activity. Panel A. Principal component analysis of miRNA microarray samples from human A2B5+ adult and CD140a+ fetal GPCs. Panel B. Log 2 fold change bar plots and heatmap of differentially expressed miRNAs. Panel C. Characterization bubble plot of enrichment of miRNAs, versus the average log 2 FC of its predicted gene targets. Panel D-Panel E. Curated signaling networks of Panel D, fetal (top) and Panel E, adult (bottom) enriched miRNAs and their predicted targets.
Figure 6E:
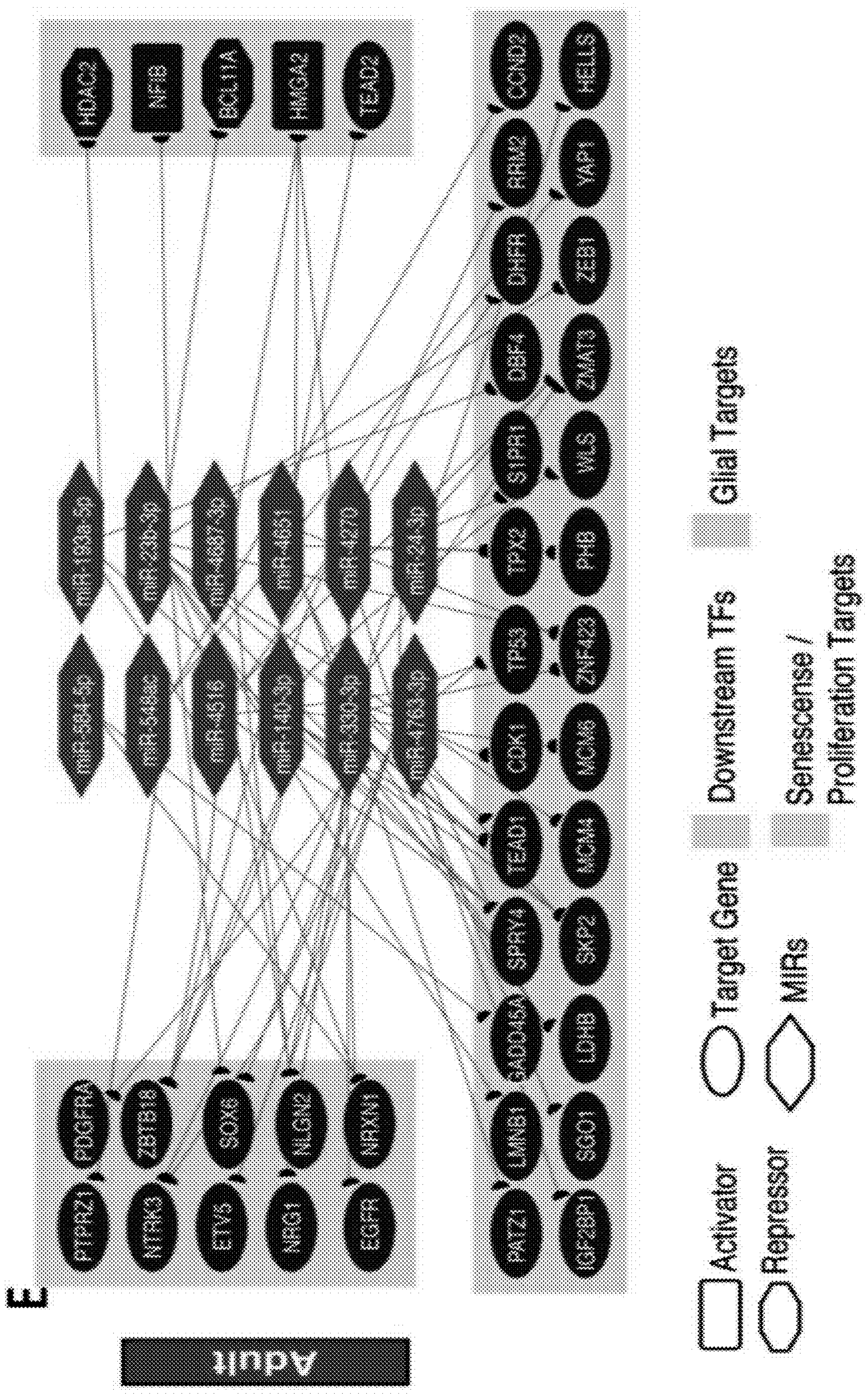
Figures 7A, 7B:
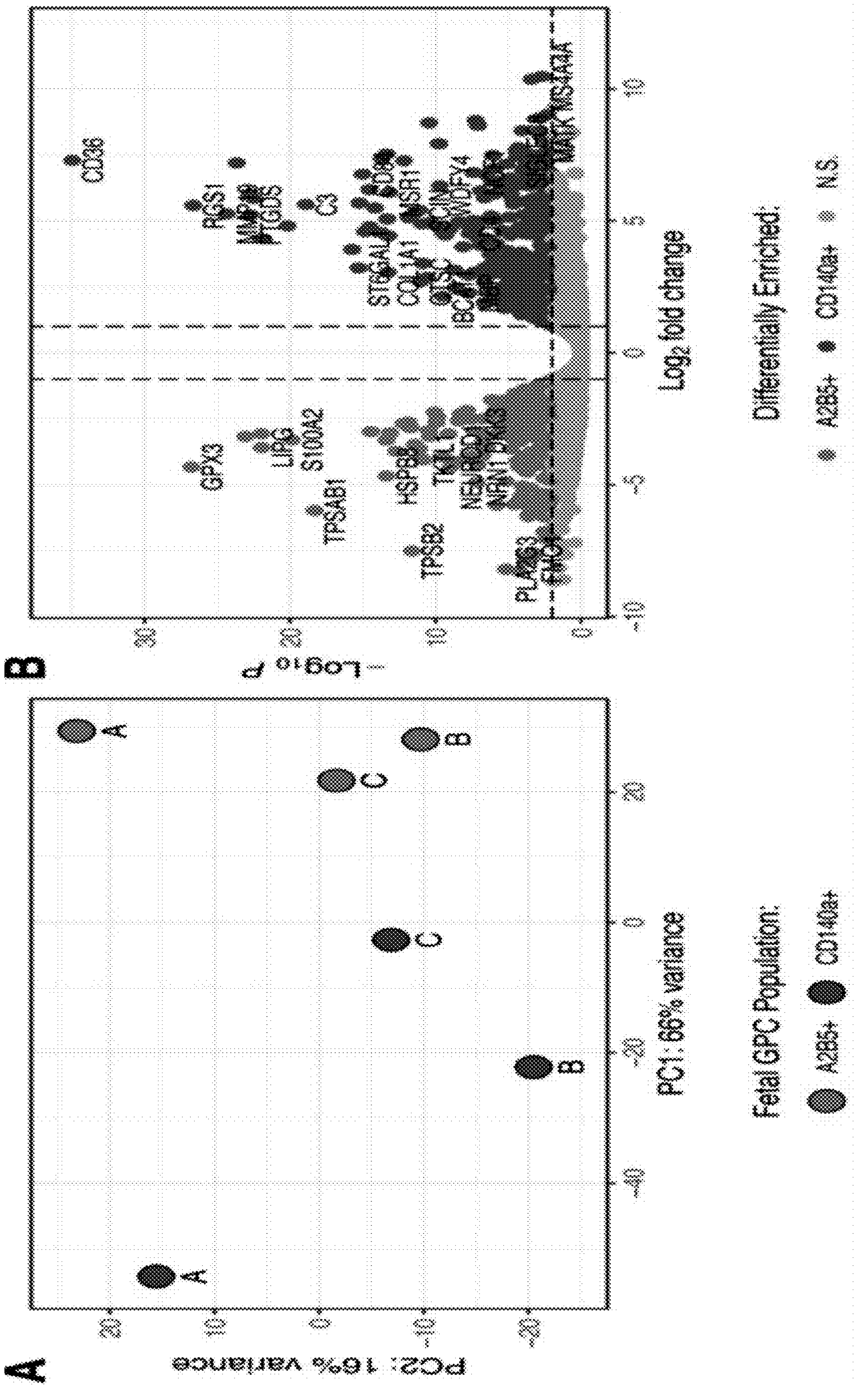
FIG. 7, which is related to FIG. 1, shows enrichment of human fetal GPCs via CD140a+ or A2B5+/PSA−NCAM− selection: Panel A. Principal component analysis of CD140a+ and A2B5+ fetal GPCs. Panel B. Volcano plots indicating significant A2B5 (Green) and CD140a (Blue) enriched genes. Panel C. Principal component analysis of CD140a+ and CD140a− fetal cells. Panel D. Volcano plots indicating significant CD140a− (Magenta) and CD140a (Blue) enriched genes. Panel E. Upset plot of significant up and downregulated genes in both genesets.
Figures 7C, 7D:
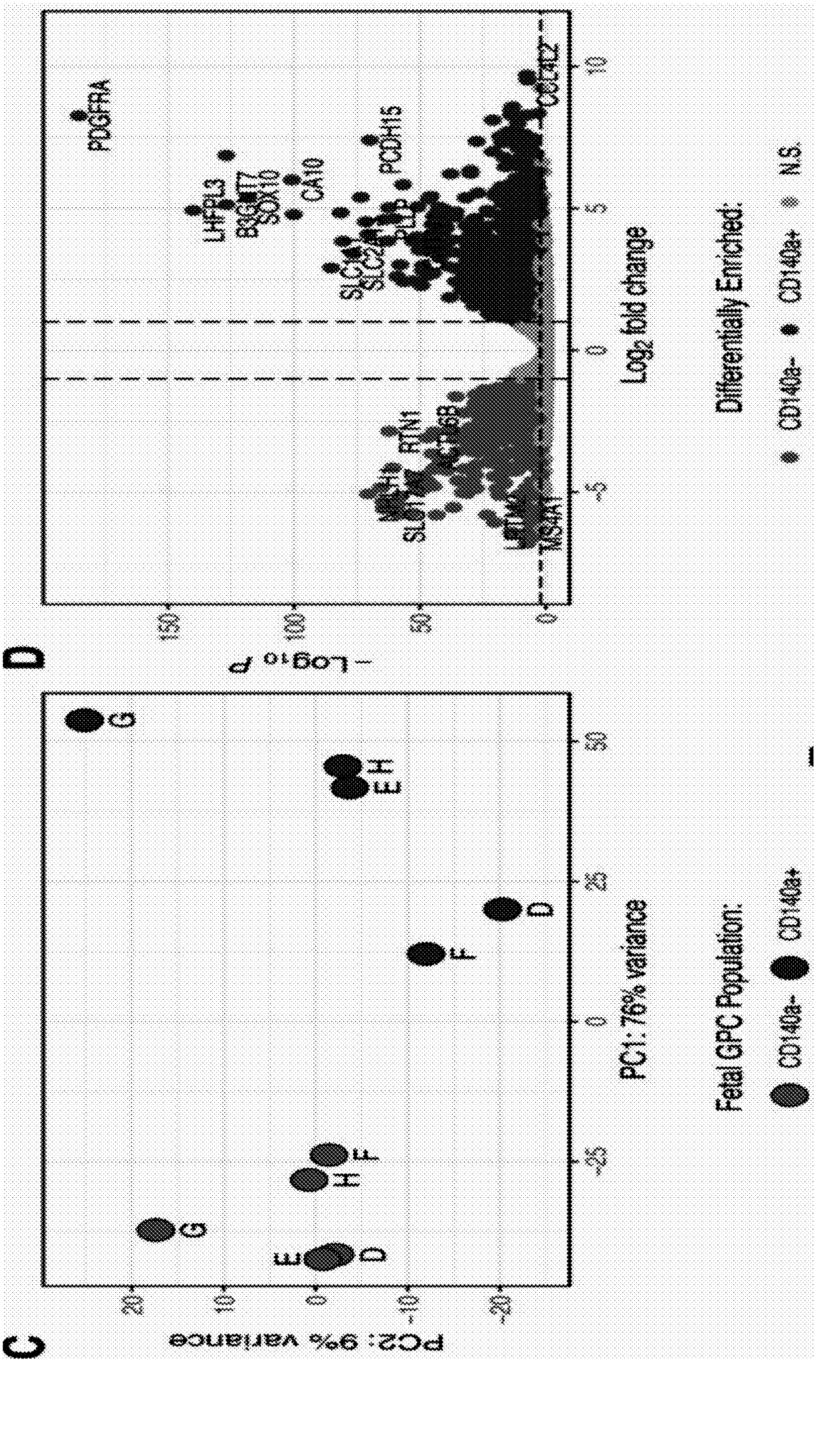
Figure 7E:
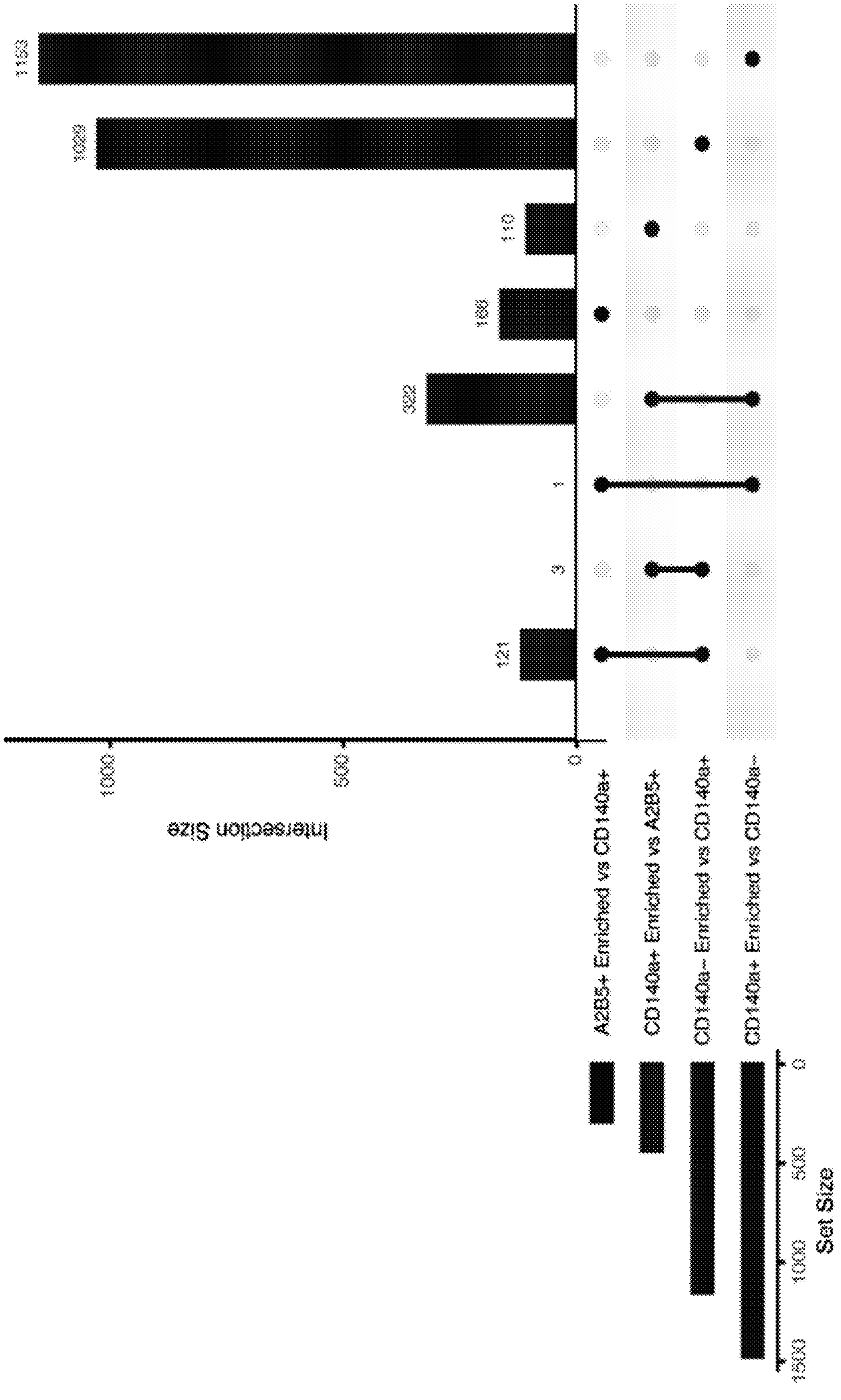
Figure 10:
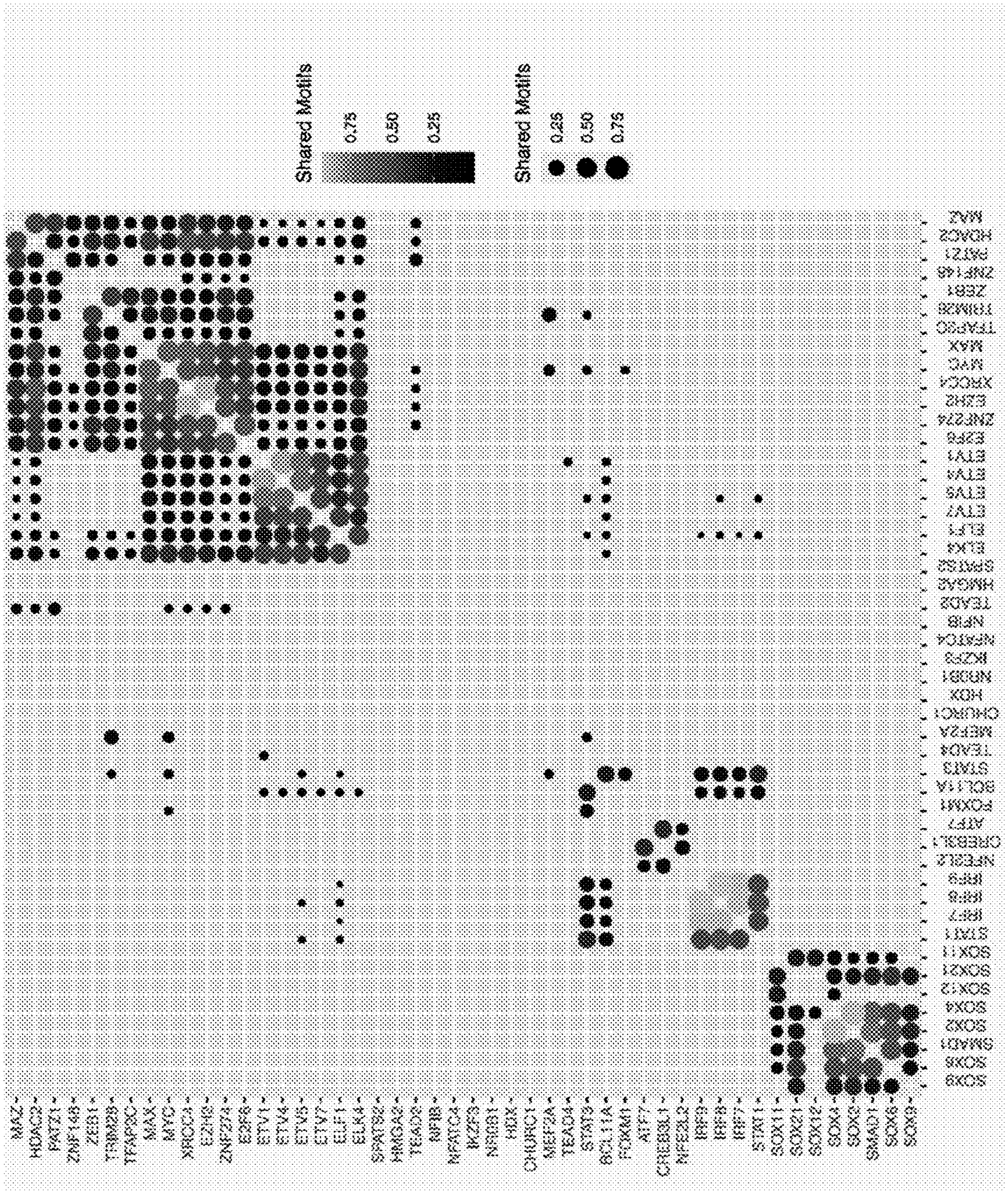
FIG. 10, which is related to FIG. 4, shows shared motifs of active transcription factors in fetal or adult hGPCs: matrix of all predicted active transcription factors in fetal and adult GPCs. Size and color indicate degree of motifs that are shared between transcription factors.
Figure 11:
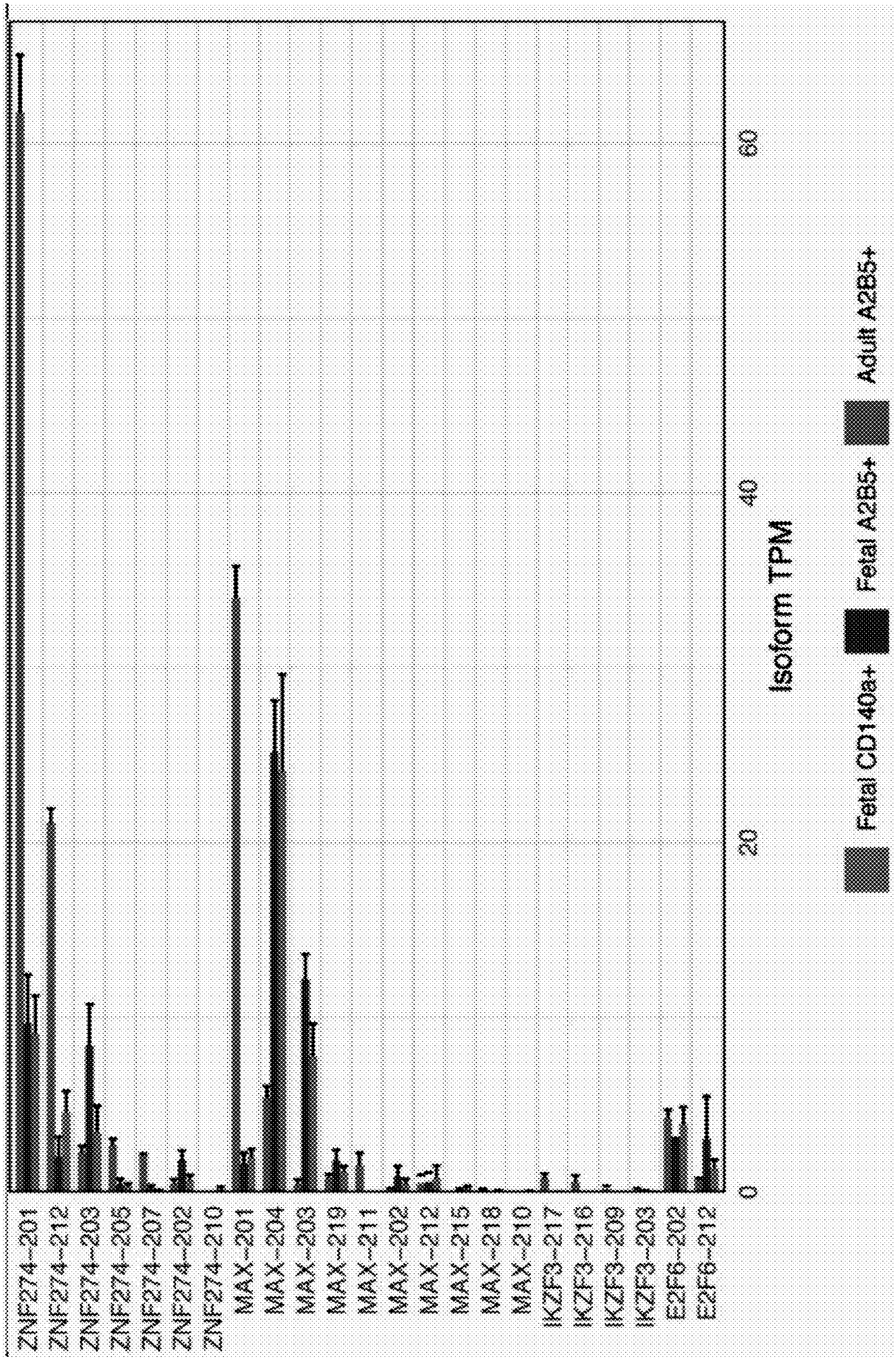
FIG. 11, which is related to FIG. 5, shows adult repressor isoform expression. Bar plots of transcripts per million (TPMs) of all protein coding adult repressor isoforms in each GPC group.
Figure 12:
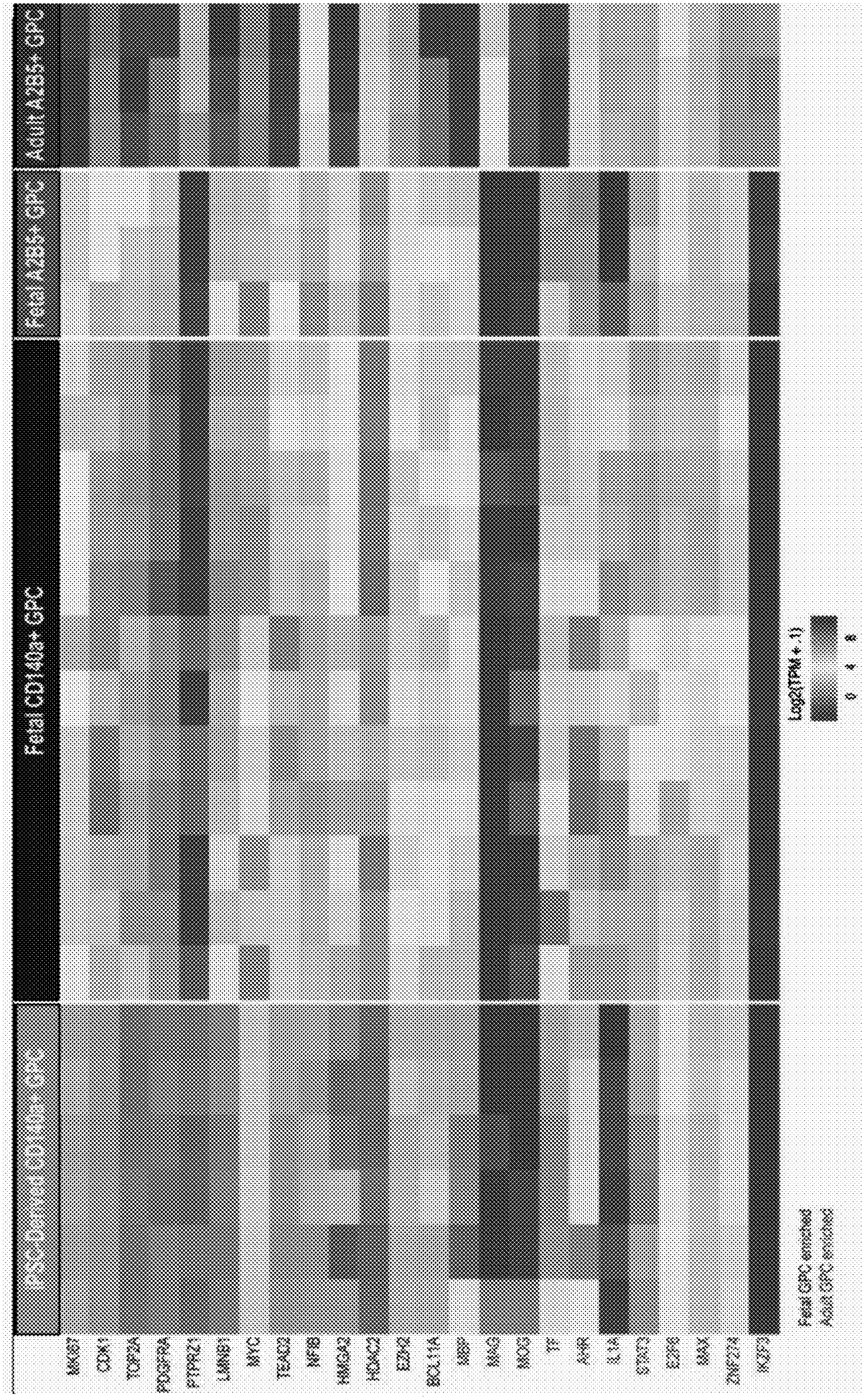
FIG. 12, which is related to FIG. 5, shows bulk RNA-Seq of iPSC-derived hGPCs reveals concordant abundance of age-associated genes. iPSC-derived hGPCs (C27) were isolated via CD140a+FACS and assayed via bulk RNA-sequencing. Abundance of relevant glial age-associated genes, including those in our active transcription factor cohort, are displayed alongside fetal and adult hGPC data.
Figure 13A:
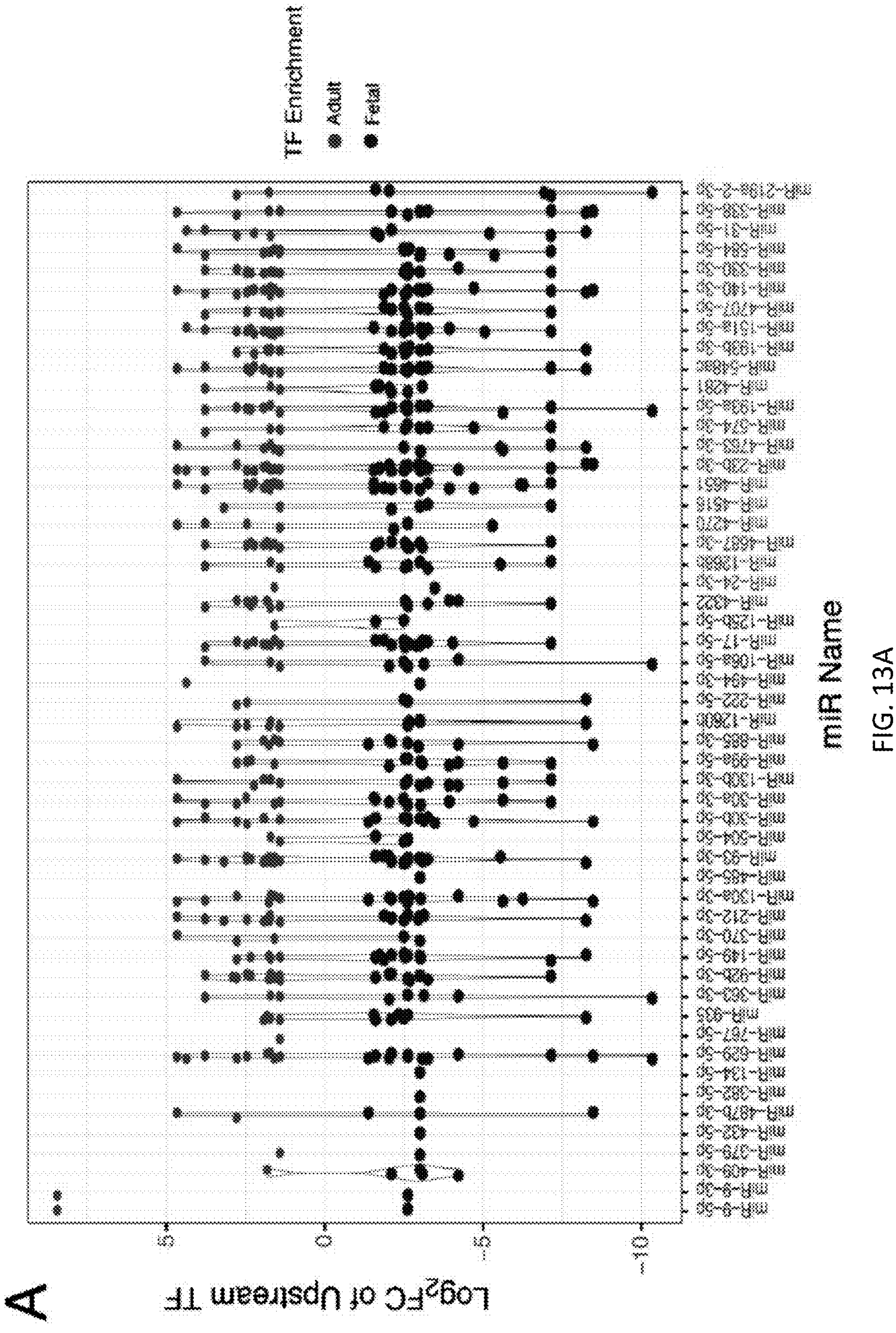
FIG. 13, which is related to FIG. 6, shows transcription factor regulation of miRNAs provides post-transcriptional modulation of glial aging gene expression: Panel (A) Log 2 FC violin plots of significant adult vs fetal GPC transcription factors predicted to be upstream of differentially expressed adult vs fetal GPC miRNAs. Panel (B) Network of identified transcription factors from FIG. 2 and their predicted regulation of differentially expressed adult vs fetal hGPC miRNAs.
Figure 13B:
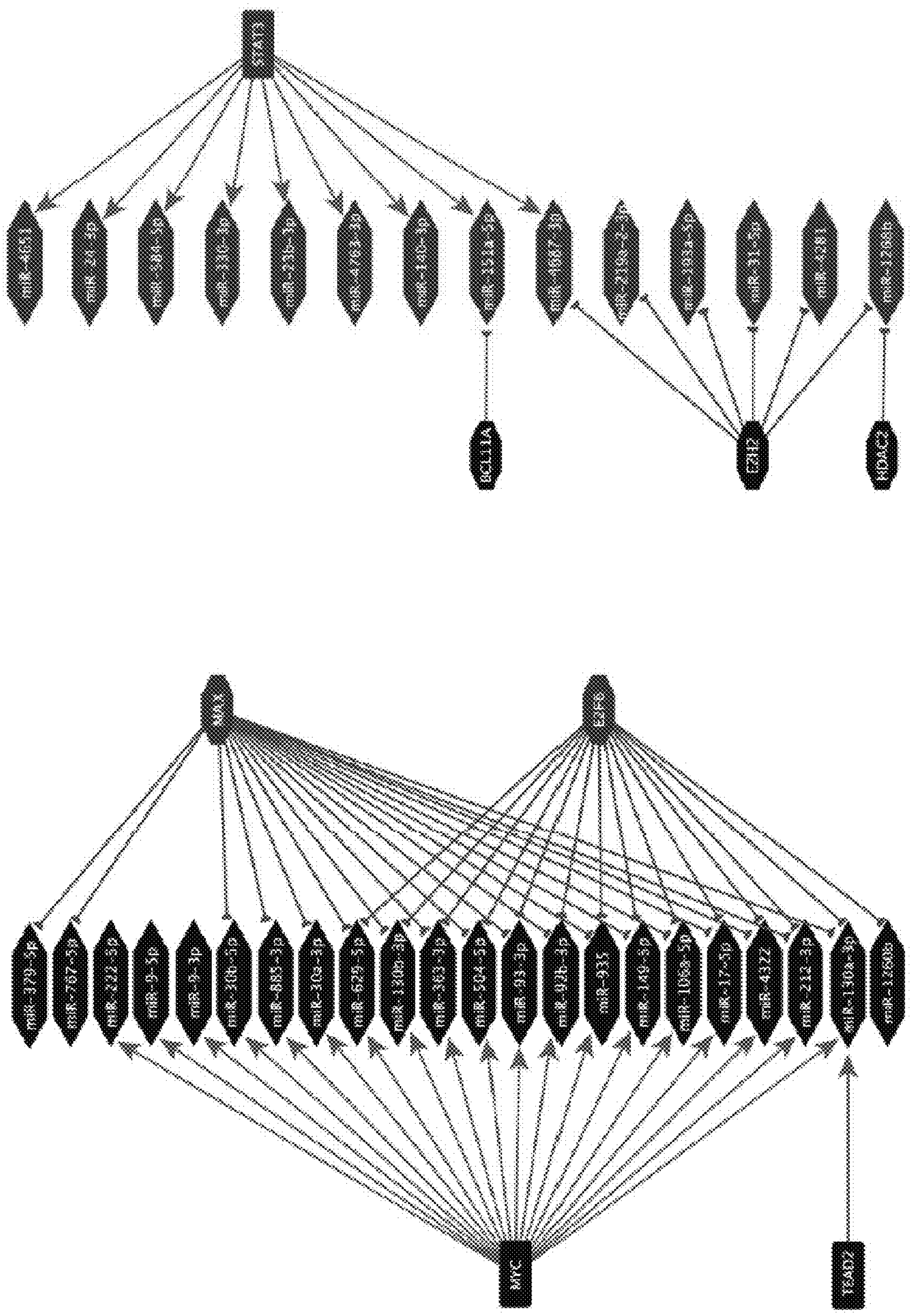

Example 6: The miRNA Expression Pattern of Fetal hGPCs Predicts their Suppression of Senescence To identify potential post-transcriptional regulators of gene expression, we assessed differences in miRNA expression between adult and fetal GPCs (n=4) utilizing Affymetrix GeneChip miRNA 3.0 arrays. PCA displayed segregation of both GPC populations as defined by their miRNA expression profiles (FIG. 6, Panel A). Differential expression between both ages (adjusted p-value <0.01) yielded 56 genes (23 enriched in adult GPCs, 33 enriched in fetal GPCs, FIG. 6, Panel B-C). Notably among these differentially expressed miRNAs were the adult oligodendrocyte regulators miR-219a-3p and miR-338-5p (Dugas, J. C., Cuellar, T. L., Scholze, A., Ason, B., Ibrahim, A., Emery, B., Zamanian, J. L., Foo, L. C., McManus, M. T., and Barres, B. A. (2010). Dicer1 and miR-219 Are required for normal oligodendrocyte differentiation and myelination. Neuron 65, 597-611) in addition to fetal progenitor stage miRNAs miR-9-3p, miR-9-5p (Lau, P., Verrier, J. D., Nielsen, J. A., Johnson, K. R., Notterpek, L., and Hudson, L. D. (2008). Identification of dynamically regulated microRNA and mRNA networks in developing oligodendrocytes. J Neurosci 28, 11720-11730), and miR-17-5p (Budde, H., Schmitt, S., Fitzner, D., Opitz, L., Salinas-Riester, G., and Simons, M. (2010). Control of oligodendroglial cell number by the miR-17-92 cluster. Development 137, 2127).

The study next utilized this cohort of miRNAs to predict genes whose expression might be expected to be repressed via miRNA upregulation, separately analyzing both the adult and fetal GPC pools. To accomplish this, miRNAtap were used to query five miRNA gene target databases: DIANA (Maragkakis, M., Vergoulis, T., Alexiou, P., Reczko, M., Plomaritou, K., Gousis, M., Kourtis, K., Koziris, N., Dalamagas, T., and Hatzigeorgiou, A. G. (2011). DIANA-microT Web server upgrade supports Fly and Worm miRNA target prediction and bibliographic miRNA to disease association. Nucleic Acids Res 39, W145-148), Miranda (Enright, A. J., John, B., Gaul, U., Tuschl, T., Sander, C., and Marks, D. S. (2003). MicroRNA targets in Drosophila. Genome biology 5, R1), PicTar (Lall, S., Grun, D., Krek, A., Chen, K., Wang, Y. L., Dewey, C. N., Sood, P., Colombo, T., Bray, N., Macmenamin, P., et al. (2006). A genome-wide map of conserved microRNA targets in *C. elegans*. Current biology: CB 16, 460-471), TargetScan (Friedman, R. C., Farh, K. K., Burge, C. B., and Bartel, D. P. (2009). Most mammalian mRNAs are conserved targets of microRNAs. Genome Res 19, 92-105), and miRDB (Wong, N., and Wang, X. (2015). miRDB: an online resource for microRNA target prediction and functional annotations. Nucleic Acids Res 43, D146-152).

To maximize precision, genes were only considered a target if they appeared in at least two databases. Among fetal-enriched miRNAs, this approach predicted an average of 36.3 (SD=24.5) repressed genes per miRNA. In contrast, among adult hGPC-enriched miRNAs, an average of 46.4 (SD=37.8) genes were predicted as targets per miRNA (FIG. 6, Panel C). Altogether, this identified the potential repression of 48.8% of adult GPC-enriched genes via fetal miRNAs, and repression of 39.9% of fetal GPC-enriched genes by adult miRNAs.

To assess the functional importance of these miRNA-dependent post-transcriptional regulatory mechanisms, the study curated fetal and adult networks according to miRNA targeting of functionally-relevant, differentially expressed genes (FIG. 6, Panel D-E). The proposed upstream adult transcriptional regulators STAT3, E2F6, and MAX were predicted to be inhibited via 7 miRNAs in fetal GPCs (FIG. 24, Panel D); these included the already-validated repression of STAT3 in other cell types by miR-126b-5p, miR-106a-5p, miR-17-5p, miR-130a-3p, and miR-130b-3p (Du, W., Pan, Z., Chen, X., Wang, L., Zhang, Y., Li, S., Liang, H., Xu, C., Zhang, Y., Wu, Y., et al. (2014a). By Targeting Stat3 microRNA-17-5p Promotes Cardiomyocyte Apoptosis in Response to Ischemia Followed by Reperfusion. Cellular Physiology and Biochemistry 34, 955-965). In parallel, a number of early and mature oligodendrocytic genes were concurrently targeted for inhibition, all consistent with maintenance of the progenitor state; these included MBP, UGT8, CD9, PLP1, MYRF, and PMP22 (Goldman, S. A., and Kuypers, N.J. (2015). How to make an oligodendrocyte. Development 142, 3983-3995). Importantly, a cohort of genes linked to either the induction of senescence or inhibition of proliferation, or both, were also predicted to be actively repressed in fetal GPCs. These included RUNX1, RUNX2, BIN1, DMTF1/DMP1, CTNNA1, SERPINE1, CDKNIC, PAK1, IFI16, EFEMP1, MAP3K7, AHR, OGT, CBX7, and CYLD (Eckers, A., Jakob, S., Heiss, C., Haarmann-Stemmann, T., Goy, C., Brinkmann, V., Cortese-Krott, M. M., Sansone, R., Esser, C., Ale-Agha, N., et al. (2016). The aryl hydrocarbon receptor promotes aging phenotypes across species. Sci Rep 6, 19618). Inhibition of senescence or activation of proliferation have also been noted by several of the miRNAs identified here, including miR-17-5p, miR-93-3p, miR-1260b, miR-106a-5p, miR-767-5p, miR-130a-3p, miR-9-3p, miR-9-5p, and miR-130b-3p (Borgdorff, V., Lleonart, M. E., Bishop, C. L., Fessart, D., Bergin, A. H., Overhoff, M. G., and Beach, D. H. (2010). Multiple microRNAs rescue from Ras-induced senescence by inhibiting p21 (Waf1/Cip1). Oncogene 29, 2262-2271). Together, these data provide a complementary mechanism by which fetal hGPCs may maintain their characteristic progenitor transcriptional state and signature.

Example 7: Adult miRNA Signaling May Repress the Proliferative Progenitor State and Augur Senescence The study next inspected the potential miRNA regulatory network within adult hGPCs (FIG. 6, Panel E). This implicated five miRNAs controlling five identified active fetal transcriptional regulators including HDAC2, NFIB, BCLL1A, TEAD2, and HMGA2, whose silencing via miR-4651 has previously been shown to inhibit proliferation (Han, X., Yang, R., Yang, H., Cao, Y., Han, N., Zhang, C., Shi, R., Zhang, Z, Fan, Z. (2020). miR-4651 inhibits proliferation of gingival mesenchymal stem cells by inhibiting HMGA2 under nifedipine treatment. Int J Oral Sci 12, 10). This cohort of miRNAs were predicted to operate in parallel to adult transcriptional repressors in inhibiting expression of genes involved in maintaining the GPC progenitor state including PDGFRA, PTPRZ1, ZBTB18, SOX6, EGFR, and NRXN1. Furthermore, the adult miRNA environment was predicted to repress numerous genes known to induce a proliferative state or to delay senescence, including LMNB1 (Freund, A., Laberge, R. M., Demaria, M., and Campisi, J. (2012). Lamin B1 loss is a senescence-associated biomarker. Mol Biol Cell 23, 2066-2075), PATZ1 (Cho, J. H., Kim, M. J., Kim, K. J., and Kim, J. R. (2012). POZ/BTB and AT-hook-containing zinc finger protein 1 (PATZ1) inhibits endothelial cell senescence through a p53 dependent pathway. Cell Death Differ 19, 703-712), GADD45A (Hollander, M. C., Sheikh, M. S., Bulavin, D. V., Lundgren, K., Augeri-Henmueller, L., Shehee, R., Molinaro, T. A., Kim, K. E., Tolosa, E., Ashwell, J. D., et al. (1999). Genomic instability in Gadd45a-deficient mice. Nat Genet 23, 176-184), YAP1 and TEAD1 (Xie, Q., Chen, J., Feng, H., Peng, S., Adams, U., Bai, Y., Huang, L., Li, J., Huang, J., Meng, S., et al. (2013). YAP/TEAD-mediated transcription controls cellular senescence. Cancer Res 73, 3615-3624.), CDK1 (Diril, M. K., Ratnacaram, C. K., Padmakumar, V. C., Du, T., Wasser, M., Coppola, V., Tessarollo, L., and Kaldis, P. (2012). Cyclin-dependent kinase 1 (Cdk1) is essential for cell division and suppression of DNA re-replication but not for liver regeneration. Proc Natl Acad Sci USA 109, 3826-3831), TPX2 (Rohrberg, J., Van de Mark, D., Amouzgar, M., Lee, J. V., Taileb, M., Corella, A., Kilinc, S., Williams, J., Jokisch, M. L., Camarda, R., et al. (2020). MYC Dysregulates Mitosis, Revealing Cancer Vulnerabilities. Cell Rep 30, 3368-3382), SIPR1 (Liu, Y., Zhi, Y., Song, H., Zong, M., Yi, J., Mao, G., Chen, L., and Huang, G. (2019). SIPR1 promotes proliferation and inhibits apoptosis of esophageal squamous cell carcinoma through activating STAT3 pathway. Journal of Experimental & Clinical Cancer Research 38, 369), RRM2 (Aird, K. M., Zhang, G., Li, H., Tu, Z., Bitler, B. G., Garipov, A., Wu, H., Wei, Z., Wagner, S. N., Herlyn, M., et al. (2013). Suppression of nucleotide metabolism underlies the establishment and maintenance of oncogene-induced senescence. Cell Rep 3, 1252-1265), CCND2 (Bunt, J., de Haas, T. G., Hasselt, N. E., Zwijnenburg, D. A., Koster, J., Versteeg, R., and Kool, M. (2010). Regulation of cell cycle genes and induction of senescence by overexpression of OTX2 in medulloblastoma cell lines. Mol Cancer Res 8, 1344-1357), SGO1 (Murakami-Tonami, Y., Ikeda, H., Yamagishi, R., Inayoshi, M., Inagaki, S., Kishida, S., Komata, Y., Jan, K., Takeuchi, I., Kondo, Y., et al. (2016). SGO1 is involved in the DNA damage response in MYCN-amplified neuroblastoma cells. Scientific Reports 6, 31615), MCM4 and MCM6 (Mason, D. X., Jackson, T. J., and Lin, A. W. (2004). Molecular signature of oncogenic ras-induced senescence. Oncogene 23, 9238-9246.), ZNF423 (Hernandez-Segura, A., de Jong, T. V., Melov, S., Guryev, V., Campisi, J., and Demaria, M. (2017). Unmasking Transcriptional Heterogeneity in Senescent Cells. Current biology: CB 27, 2652-2660), PHB (Piper, P. W., Jones, G. W., Bringloe, D., Harris, N., MacLean, M., and Mollapour, M. (2002). The shortened replicative life span of prohibitin mutants of yeast appears to be due to defective mitochondrial segregation in old mother cells. Aging cell 1, 149-157), WLS (Poudel, S. B., So, H. S., Sim, H. J., Cho, J. S., Cho, E. S., Jeon, Y. M., Kook, S. H., and Lee, J. C. (2020). Osteoblastic Wntless deletion differentially regulates the fate and functions of bone marrow-derived stem cells in relation to age. Stem Cells.), and ZMAT3 (Kim, B. C., Lee, H. C., Lee, J. J., Choi, C. M., Kim, D. K., Lee, J. C., Ko, Y. G., and Lee, J. S. (2012). Wig1 prevents cellular senescence by regulating p21 mRNA decay through control of RISC recruitment. EMBO J 31, 4289-4303). More directly, induction of senescence or inhibition of proliferation has been linked to the upregulation of miR-584-5p (Li, Q., Li, Z., Wei, S., Wang, W., Chen, Z., Zhang, L., Chen, L., Li, B., Sun, G., Xu, J., et al. (2017). Overexpression of miR-584-5p inhibits proliferation and induces apoptosis by targeting WW domain-containing E3 ubiquitin protein ligase 1 in gastric cancer. J Exp Clin Cancer Res 36, 59), miR-193a-5p (Chen, J., Gao, S., Wang, C., Wang, Z., Zhang, H., Huang, K., Zhou, B., Li, H., Yu, Z., Wu, J., et al. (2016). Pathologically decreased expression of miR-193a contributes to metastasis by targeting WT1-E-cadherin axis in non-small cell lung cancers. J Exp Clin Cancer Res 35, 173), miR-548ac (Song, F., Yang, Y., and Liu, J. (2020). MicroRNA-548ac induces apoptosis in laryngeal squamous cell carcinoma cells by targeting transmembrane protein 158. Oncol Lett 20, 69), miR-23b-3p (Campos-Viguri, G. E., Peralta-Zaragoza, O., Jimenez-Wences, H., Longinos-Gonzalez, A. E., Castanon-Sanchez, C. A., Ramirez-Carrillo, M., Camarillo, C. L., Castaneda-Saucedo, E., Jimenez-Lopez, M. A., Martinez-Carrillo, D. N., et al. (2020). MiR-23b-3p reduces the proliferation, migration and invasion of cervical cancer cell lines via the reduction of c-Met expression. Sci Rep 10, 3256), miR-140-3p (Wang, M., Wang, X., and Liu, W. (2020a). MicroRNA-130a-3p promotes the proliferation and inhibits the apoptosis of cervical cancer cells via negative regulation of RUNX3. Mol Med Rep 22, 2990-3000), and miR-330-3p (Wang, Y., Chen, J., Wang, X., and Wang, K. (2020b). miR-140-3p inhibits bladder cancer cell proliferation and invasion by targeting FOXQ1. Aging 12, 20366-20379). Taken together, these data implicate these miRs as active participants in maintenance of the progenitor state in fetal hGPCs, and their modulation as a likely mechanism by which adult hGPCs assume their signatory gene expression profile.

Example 8: Transcription Factor Regulation of miRNAs Establishes and Consolidates GPC Identity The study next sought to predict the upstream regulation of differentially expressed miRNAs in fetal and adult GPCs by querying the TransmiR transcription factor miRNA regulation database (Tong, et al. (2019). TransmiR v2.0: an updated transcription factor-microRNA regulation database. Nucleic Acids Res 47, D253-D258). This approach predicted regulation of 54 of 56 of age-specific GPC miRNAs via 66 transcription factors that were similarly determined to be significantly differentially expressed between fetal and adult GPCs. Interestingly, the top four predicted miRNA-regulating TFs were all MYC-associated factors including MAX, MYC itself, E2F6, and the fetal enriched MYC associated zinc finger protein, MAZ, targeting 36, 33, 30, and 28 unique differentially expressed miRNAs respectively.

Inspection of proposed relationships in the context of the 12 TF candidates indicated a large number of fetal hGPC-enriched miRNAs that were predicted to be targeted by both fetal activators and adult repressors, whereas those miRNAs enriched in adult GPCs were more uniquely targeted. MYC was predicted to drive the expression of numerous miRNAs in fetal GPCs, many of which were predicted to be repressed in adulthood via E2F6, MAX or both. miR-130a-3p in particular was predicted to be targeted by MYC, MAX, and E2F6, in addition to activation via TEAD2. Notably among validated TF-miRNA interactions in other cell types, the upregulation of the rejuvenating miR-17-5p by MYC, and its repression by MAX (Du, et al. (2014b). miR-17 extends mouse lifespan by inhibiting senescence signaling mediated by MKP7. Cell Death Dis 5, e1355), has been reported.

Similarly, the parallel activation of the proliferative miR-130-3p by MYC or TEAD2 and YAP1 (Shen, et al. (2015). A miR-130a– YAP positive feedback loop promotes organ size and tumorigenesis. Cell Res 25, 997-1012), has been reported, as has the activation of both arms of miR-9 by MYC (Ma, L., et al. (2010a). miR-9, a MYC/MYCN-activated microRNA, regulates E-cadherin and cancer metastasis. Nat Cell Biol 12, 247-256), which decreases with oligodendrocytic maturity (Lau, P., et al. (2008). Identification of dynamically regulated microRNA and mRNA networks in developing oligodendrocytes. J Neurosci 28, 11720-11730).

In adult GPCs, enriched miRNAs predicted to be regulated by our significantly enriched TF cohort were more likely to be only targeted by an adult activator of fetal repressor with only miR-151a-5p and miR-4687-3p, a predicted inhibitor of HMGA2, being targeted in opposition by STAT3 versus BCL11A and EZH2 respectively. Beyond this, miR-1268b was predicted to be inhibited by both EZH2 and HDAC2 in parallel. Notably, key oligodendrocytic microRNA, miR-219a-2-3p was predicted to remain inhibited in fetal GPCs via EZH2, whereas STAT3 likely drives the expression of 7 other miRs independently. Interestingly, STAT3, whose increased activity has been linked to senescence (Kojima, et al. (2013). IL-6-STAT3 signaling and premature senescence. JAKSTAT 2, e25763), was also predicted to drive the expression of a cohort of miRNAs independently associated with the induction of senescence, including miR-584-5p, miR-330-3p, miR-23b-3p, and miR-140-3p.

Through integration of transcriptional and miRNA profiling, pathway enrichment analyses, and target predictions, we propose a model of human GPC aging whereby fetal hGPCs maintain progenitor gene expression, activate proliferative programs, and prevent senescence, while repressing oligodendrocytic and senescent gene programs both transcriptionally, and post-transcriptionally via microRNA. With adult maturation and the passage of time as well as of population doublings, hGPCs begin to upregulate repressors of these fetal progenitor-linked networks, while also activating programs to further a progressively more differentiated and ultimately senescent phenotype.

Example 9: Expression of BCL11A in the Brain of Chimeric Animal Model Results in Proliferation of BCL11A Expressing GPCs in the Host By analyzing RNA sequencing data from fetal and adult human glial progenitor cells (GPCs) sorted from fresh tissue samples, the study identified several transcription factors as central in gene regulatory networks that distinguish f "young" vs "old" GPCs. Among these, the transcriptional repressor BCL11A (B cell CLL/lymphoma 11A) was one of the most prominently differentially expressed genes, high in fetal hGPCs and low in adult cells, suggesting its role in preserving the fetal hGPC phenotype. BCL11A had never been known to play such a role in the central nervous system, or in the regulation of glial progenitor cell expansion, fate or aging.

To investigate then whether BCL11A could re-initiate or accelerate self-renewal in aged GPCs, the study generated a lentivirus to express BCL11A and GFP driven by the CBh promoter (hereby referred to as CBh-BCL11A), as well as a green fluorescent protein (GFP)-only control virus (CBh-GFP) (FIG. 14*a*). GPCs were generated from the human C27 iPSC line, tagged with a red fluorescent-expressing transgene (RFP) (FIG. 14*b*), then engrafted into the corpus callosum (CC) of Rag1 immunodeficient mice on postnatal day 1, as previously described (P1, 300k cells/animal) (Windrem at al. J. Neurosci 34, 16153-16161 (2014), Windrem et al., Cell Stem Cell 21, 195-208.e6 (2017)). Chimerized mice were allowed to age for 2 years following engraftment, at which point they received stereotactic injection of CBh-BCL11A in the left hemisphere, and CBh-GFP control virus in the right hemisphere. Virus was deposited in the striatum, corpus callosum, and cortex. At either 3 or 6 weeks post-injection, mice were either dissected for single-cell analysis, or perfused with 4% PFA for sectioning and immunohistochemistry (FIG. 14*c*).

The study confirmed overexpression of BCL11A via both RNA expression in vitro (FIG. 14*d*), and protein staining in vivo (FIG. 14*e*). Three weeks post-infection, the study observed an expansion of the GPC population in the CBh-BCL11A-treated hemisphere, as compared to the control side of the brain (FIG. 15*a*). The study found a robust increase in the presence of RFP-tagged human cells and OLIG2+ cells of the GPC lineage (FIG. 15*b*, quantified in 15c), as well as an increase in resident mouse GPCs, identified by the mouse NG2 antigen (FIG. 15*d*, quantified in 15e). This effect was still present at 6 weeks post-infection (FIG. 16*a*), with more RFP+ and OLIG2+ cells detected on the CBh-BCL11A-infected hemisphere than in the CBh-GFP-treated controls (FIG. 16*b*). At that 6 week timepoint, donor cell dispersal was both broad and relatively uniform; no tumors or heterotopias were found. These observations indicated that BCL11A transduction activated both aged resident human and mouse GPCs alike, to re-initiate mitotic expansion and migratory colonization of their host brains. Furthermore, the (red) membrane-tagging of the BCL11A-mobilized human donor cells allowed the morphologies of a large fraction of those in the white matter to be defined as myelinating oligodendrocytes, suggesting at least partial reversal of the typical age-associated loss of myelin in these aged mice.

Herein incorporated by reference is the sequence listing filed with the USPTO as 1134-086US_Sequence.xml which was created on Oct. 17, 2022, and the size is 22,306 bytes.

While various embodiments have been described above, it should be understood that such disclosures have been presented by way of example only and are not limiting. Thus, the breadth and scope of the subject compositions and methods should not be limited by any of the above-described exemplary embodiments, but should be defined only in accordance with the following claims and their equivalents.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A method of repressing a senescence-associated gene expression signature in a population of adult glial progenitor cells, said method comprising:

administering, to the population of adult glial progenitor cells, an agent that suppresses one or more transcription factors selected from zinc finger protein 274 (ZNF274) and E2F transcription factor 6 (E2F6), wherein the agent comprises one or more nucleic acid molecules that comprise a first nucleic acid sequence encoding a Cas protein and a second nucleic acid sequence encoding a guide RNA, wherein the guide RNA is complementary to an E2F6 gene of Accession No: NM 001278277.2 or is complementary to a ZNF274 gene of Accession No: XR 001753588.2, wherein the guide RNA is 5 to 100 nucleic acid residues in length; and wherein the senescence-associated gene expression signature comprises CDKN1A/p21.

2. The method of claim 1, wherein the first nucleic acid sequence and the second nucleic acid sequence are located on the same nucleic acid molecule.

3. The method of claim 1, wherein the Cas protein is a nuclease dead Cas protein.

4. The method of claim 1, wherein the one or more nucleic acid molecules are encoded by a non-viral expression vector.

5. The method of claim 1, wherein the one or more nucleic acid molecules are encoded by a viral expression vector.

6. The method of claim 5, wherein the viral expression vector is a lentiviral vector.

7. The method of claim 5, wherein the viral expression vector is an AAV vector.

8. The method of claim 1, wherein the first nucleic acid sequence encoding a Cas protein and the second nucleic acid sequence encoding a guide RNA are operably linked to a regulatory element.

9. The method of claim 8, wherein the regulatory element is a glial cell-specific promoter.

10. The method of claim 8, wherein the regulatory element is an inducible promoter.

11. The method of claim 10, wherein the inducible promoter is a tet-on or tet-off promoter.

12. A method of suppressing expression of either CDKN1A/p21 or CDKN2A/p16, or both in a population of adult glial progenitor cells, said method comprising:

administering, to the population of adult glial progenitor cells, an agent that suppresses one or more transcription factors, wherein the one or more transcription factors are selected from zinc finger protein 274 (ZNF274) and E2F transcription factor 6 (E2F6), wherein the agent comprises one or more nucleic acid molecules that comprise a first nucleic acid sequence encoding a Cas protein and a second nucleic acid sequence encoding a guide RNA comprising a nucleotide sequence that is complementary to a portion of a gene encoding one or more of the transcription factors; and wherein the nucleotide sequence of the guide RNA is complementary to an E2F6 gene of Accession No: NM 001278277.2 or is complementary to a ZNF274 gene of Accession No: XR 001753588.2, wherein the guide RNA is 5 to 100 nucleic acid residues in length.

* * * * *